(12) United States Patent
Barf et al.

(10) Patent No.: US 10,239,883 B2
(45) Date of Patent: Mar. 26, 2019

(54) 4-IMIDAZOPYRIDAZIN-1-YL-BENZAMIDES AS BTK INHIBITORS

(71) Applicant: Merck Sharp & Dohme B.V., Haarlem (NL)

(72) Inventors: Tjeerd A. Barf, Ravenstein (NL); Christiaan Gerardus Johannes Maria Jans, Cuijk (NL); Adrianus Petrus Antonius de Man, Hurwenen (NL); Arthur A. Oubrie, Wijchen (NL); Hans C. A. Raaijmakers, Eindhoven (NL); Johannes Bernardus Maria Rewinkel, Berghem (NL); Jan Gerard Sterrenburg, Renkum (NL); Jacobus C. H. M. Wijkmans, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

(21) Appl. No.: 15/668,385

(22) Filed: Aug. 3, 2017

(65) Prior Publication Data

US 2018/0179212 A1 Jun. 28, 2018

Related U.S. Application Data

(60) Continuation of application No. 15/019,543, filed on Feb. 9, 2016, now Pat. No. 9,758,524, which is a division of application No. 14/233,418, filed as application No. PCT/EP2012/063552 on Jul. 11, 2012, now Pat. No. 9,290,504.

(60) Provisional application No. 61/509,397, filed on Jul. 19, 2011.

(30) Foreign Application Priority Data

Jul. 19, 2011 (EP) ..................................... 11174578

(51) Int. Cl.
| | | |
|---|---|---|
| *C07D 487/04* | (2006.01) | |
| *A61K 31/4985* | (2006.01) | |
| *C07D 519/00* | (2006.01) | |
| *A61K 31/501* | (2006.01) | |
| *A61K 31/506* | (2006.01) | |
| *A61K 31/55* | (2006.01) | |
| *A61K 31/5377* | (2006.01) | |

(52) U.S. Cl.
CPC ........ *C07D 487/04* (2013.01); *A61K 31/4985* (2013.01); *A61K 31/501* (2013.01); *A61K 31/506* (2013.01); *A61K 31/5377* (2013.01); *A61K 31/55* (2013.01); *C07D 519/00* (2013.01); *Y02A 50/411* (2018.01)

(58) Field of Classification Search
CPC .......................... C07D 487/04; A61K 31/4985
See application file for complete search history.

(56) References Cited

U.S. PATENT DOCUMENTS

| 7,825,118 B2 | 11/2010 | Honigberg et al. | |
|---|---|---|---|
| 7,960,396 B2 | 6/2011 | Honigberg et al. | |
| 8,377,946 B1 | 2/2013 | Chen et al. | |
| 8,658,794 B2 | 2/2014 | de Man et al. | |
| 9,290,504 B2 * | 3/2016 | Barf .................... | C07D 487/04 |
| 9,718,828 B2 * | 8/2017 | De Man ............... | C07D 487/04 |
| 9,758,524 B2 * | 9/2017 | Barf .................... | C07D 487/04 |

(Continued)

FOREIGN PATENT DOCUMENTS

| EP | 2548877 A1 | 1/2013 |
|---|---|---|
| WO | WO-2000017203 A1 | 3/2000 |

(Continued)

OTHER PUBLICATIONS

Berge et al., "Pharmaceutical salts," 66(1) J. Pharm. Sci. 1-19 (1977).
Bingham et al., "Over one hundred solvates of sulfathiazole," Chem. Commun. 603-04 (2001).
Caira et al., "Preparation and Crystal Characterization of a Polymorph, a Monohydrate, and an Ethyl Acetate Solvate of the Antifungal Fluconazole," 93(3) J. Pharma. Sci. 601-11 (2004).

(Continued)

*Primary Examiner* — Golam M Shameem
(74) *Attorney, Agent, or Firm* — Covington & Burling LLP; Melody Wu; Jennifer L. Robbins

(57) ABSTRACT

The present invention relates to 6-5 membered fused pyridine ring compounds according to Formula (I)

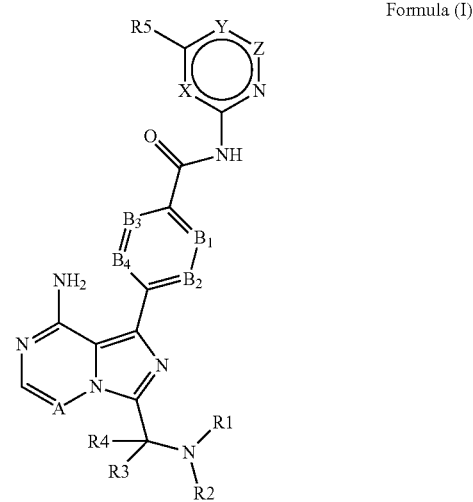

Formula (I)

or a pharmaceutically acceptable salt thereof or to pharmaceutical compositions comprising these compounds and to their use in therapy. In particular, the present invention relates to the use of 6-5 membered fused pyridine ring compounds according to Formula (I) in the treatment of Bruton's Tyrosine Kinase (Btk) mediated disorders.

14 Claims, No Drawings

(56) References Cited

U.S. PATENT DOCUMENTS

| | | | |
|---|---|---|---|
| 9,790,226 | B2* | 10/2017 | Barf .................... C07D 487/04 |
| 2006/0084654 | A1 | 4/2006 | Beck et al. |
| 2008/0076921 | A1 | 3/2008 | Honigberg et al. |
| 2011/0257203 | A1 | 10/2011 | Honigberg et al. |
| 2012/0053189 | A1 | 3/2012 | Loury |
| 2012/0095026 | A1 | 4/2012 | Honigberg et al. |
| 2012/0129821 | A1 | 5/2012 | Honigberg et al. |
| 2012/0135944 | A1 | 5/2012 | Honigberg et al. |
| 2012/0165328 | A1 | 6/2012 | Honigberg et al. |
| 2013/0018032 | A1 | 1/2013 | Chen et al. |
| 2013/0079327 | A1 | 3/2013 | Yamamoto et al. |
| 2014/0073593 | A1 | 3/2014 | Conklin et al. |
| 2014/0206681 | A1 | 7/2014 | Kim et al. |
| 2014/0212425 | A1 | 7/2014 | Chang et al. |

FOREIGN PATENT DOCUMENTS

| | | | |
|---|---|---|---|
| WO | WO-2001019828 | A2 | 3/2001 |
| WO | WO-2002080926 | A1 | 10/2002 |
| WO | WO-2003065995 | A2 | 8/2003 |
| WO | WO-2005014599 | A1 | 2/2005 |
| WO | WO-2005037836 | A2 | 4/2005 |
| WO | WO-2005097800 | A1 | 10/2005 |
| WO | WO-2007061737 | A2 | 5/2007 |
| WO | WO-2007064883 | A2 | 6/2007 |
| WO | WO-2007064993 | A2 | 6/2007 |
| WO | WO-2007106503 | A2 | 9/2007 |
| WO | WO-2008121742 | A2 | 10/2008 |
| WO | WO-2009076170 | A2 | 6/2009 |
| WO | WO-2010126960 | A1 | 11/2010 |
| WO | WO-2011095556 | A1 | 8/2011 |
| WO | WO-2011119663 | A1 | 9/2011 |
| WO | WO-2011152351 | A1 | 12/2011 |
| WO | WO-2011153514 | A2 | 12/2011 |
| WO | WO-2012158843 | A2 | 11/2012 |
| WO | WO-2013003629 | A2 | 1/2013 |
| WO | WO-2013010380 | A1 | 1/2013 |
| WO | WO-2013010868 | A1 | 1/2013 |
| WO | WO-2013010869 | A1 | 1/2013 |
| WO | WO-2013059738 | A2 | 4/2013 |
| WO | WO-2014143807 | A2 | 9/2014 |
| WO | WO-2014159745 | A1 | 10/2014 |
| WO | WO-2014168975 | A1 | 10/2014 |
| WO | WO-2015018522 | A1 | 2/2015 |

OTHER PUBLICATIONS

Davis et al., "Chronic active B-cell-receptor signalling in diffuse large B-cell lymphoma," 463 Nature 88-92 (2010).

Dhar et al., "Synthesis and SAR of p38α MAP kinase inhibitors based on heterobicyclic scaffolds," 17 Bioorg. & Med. Chem. Lett. 5019-24 (2007).

Gaudet et al., "A Homogeneous Fluorescence Polarization Assay Adaptable for a Range of Protein Serine/Threonine and Tyrosine Kinases," 8(2) J. Biomol. Screening 164-75 (2003).

Gennaro (ed.), *Remington: The Science and Practice of Pharmacy*, 20th edition (2000).

Gilfillan et al., "The tyrosine kinase network regulating mast cell activation," 288 Immun. Rev. 149-69 (2009).

Gould, "Salt selection for basic drugs," 33 Int'l J. Pharmaceutics 201-217 (1986).

Greene & Wuts, *Protective Groups in Organic Synthesis*, 2d Edition (1991).

Harder et al., "Gain- and Loss-of-Function Lyn Mutant Mice Define a Critical Inhibitory Role for Lyn in the Myeloid Lineage," 15 Immunity 603-15 (2001).

Hartz et al., "Synthesis and Evaluation of Imidazo[1,5-a]pyrazines as Corticotropin Releasing Hormone Receptor Ligands," 12 Bioorg. & Med. Chem. Lett. 291-94 (2002).

Higuchi et al. (eds.), *Pro-drugs as Novel Delivery Systems*, 14 A.C.S. Symposium Series (1975).

Ji et al., "A novel, potent, and selective insulin-like growth factor-I receptor kinase inhibitor blocks insulin-like growth factor-I receptor signaling in vitro and inhibits insulin-like growth factor-I receptor-dependent tumor growth in vivo," 6(8) Mol. Cancer Ther. 2158-67 (2007).

King et al., "Nucleofugality effects in the pyridine promoted formation of esters from 2-substituted ethanesulfonyl chlorides," 66 Can. J. Chem. 1109-16 (1988).

Klinghoffer et al., "Src family kinases are required for integrin but not PDGFR signal transduction," 18(9) EMBO J. 2459-71 (1999).

Lim et al., "Anti-CD20 monoclonal antibodies: historical and future perspectives," 95(1) Haematologica 135-43 (2010).

Lowell et al., "Deficiency of the Hck and Src Tyrosine Kinases Results in Extreme Levels of Extramedullary Hematopoiesis," 87(5) Blood 1780-92 (1996).

Mitchell et al., Synthesis of C-nucleoside isosteres of 9-(2-hydroxyethoxymethyl)guanine (acyclovir), 21(3) J. Heterocyclic Chem. 697-99 (1984).

Mukaiyama et al., "Synthesis and c-Src inhibitory activity of imidazo[1,5-a]pyrazine derivatives as an agent for treatment of acute ischemic stroke," 15 Bioorg. & Med. Chem. 868-85 (2007).

Mulvihill et al., "1,3-Disubstituted-imidazo[1,5-a]pyrazines as insulin-like growth-factor-I receptor (IGF-IR) inhibitors," 17 Bioorg. & Med. Chem. Lett. 1091-97 (2007).

Mulvihill et al., "Novel 2-phenylquinolin-7-yl-derived imidazo[1,5-a]pyrazines as potent insulin-growth factor-I receptor (IGF-IR) inhibitors," 16 Bioorg. & Med. Chem. 1359-75 (2008).

Odom et al., "Negative Regulation of Immunoglobulin E-dependent Allergic Responses by Lyn Kinase," 199(11) J. Exp. Med. 1491-1502 (2004).

Pan et al., "Discovery of Selective Irreversible Inhibitors for Bruton's Tyrosine Kinase," 2 ChemMedChem 58-61 (2007).

Roby et al., "Alterations in Reproductive Function in Src Tyrosine Kinase Knockout Mice," 26 Endocrine 169-76 (2005).

Roche (ed.), *Bioreversible Carriers in Drug Design*, Pergamon Press (1987).

Shinohara et al., "Tyrosine Kinases Btk and Tec Regulate Osteoclast Differentiation by Linking RANK and ITAM Signals," 132 Cell 794-806 (2008).

Van Tonder et al., "Preparation and Physicochemical Characterization of 5 Niclosamide Solvates and 1 Hemisolvate," 5(1) AAPS PharmSciTech Article 12 (2004).

* cited by examiner

4-IMIDAZOPYRIDAZIN-1-YL-BENZAMIDES AS BTK INHIBITORS

RELATED APPLICATIONS

This application is a divisional of U.S. patent application Ser. No. 15/019,543, which is a divisional of U.S. patent application Ser. No. 14/233,418, now U.S. Pat. No. 9,290,504, which is the U.S. national stage of International Patent Application No. PCT/EP2012/063552 filed Jul. 11, 2012, which claims priority to U.S. Patent Application No. 61/509,397 filed Jul. 19, 2011, and to EP Patent Application No. 11174578.2 filed Jul. 19, 2011, each of which is hereby incorporated by reference in its entirety herein.

FIELD OF THE INVENTION

The present invention relates to 6-5 membered fused pyridine ring compounds, to pharmaceutical compositions comprising these compounds and to their use in therapy. In particular, the present invention relates to the use of 6-5 membered fused pyridine ring compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton's tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll like receptor signaling was suggested. Functional mutations in Btk in humans results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These findings support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gilfillan et al, Immunological Reviews 288 (2009) pp 149-169].

Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-92].

Some classes of 6-5 membered fused pyridine ring compounds have been described as kinase inhibitors e.g. Imidazo[1,5-f][1,2,4]triazine compounds have been described in WO2005097800 and WO2007064993. Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases. Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice.

Female Src knockout mice are infertile due to reduced follicle development and ovulation [Roby et al, Endocrine, 26 (2005) pp 169-176].

The double knockouts $Src^{-/-}Fyn^{-/-}$ and $Src^{-/-}Yes^{-/-}$ show a severe phenotype with effects on movement and breathing. The triple knockouts $Src^{-/-}Fyn^{-/-}Yes^{-/-}$ die at day 9.5 [Klinghoffer et al, EMBO J., 18 (1999) pp 2459-2471]. For the double knockout $Src^{-/-}Hck^{-/-}$, two thirds of the mice die at birth, with surviving mice developing osteopetrosis, extramedullary hematopoiesis, anemia, and leukopenia [Lowell et al, Blood, 87 (1996) pp 1780-1792].

Hence, an inhibitor that inhibits multiple or all kinases of the Src-family kinases simultaneously may cause serious adverse effects.

DETAILED DESCRIPTION OF THE INVENTION

The object of the present invention is to provide 6-5 membered fused pyridine ring compounds, to pharmaceutical compositions comprising these compounds and to their use in therapy. In particular, the present invention relates to the use of 6-5 membered fused pyridine ring compounds in the treatment of Bruton's Tyrosine Kinase (Btk) mediated disorders.

More specifically, the present invention provides 6-5 membered fused pyridine ring compounds according to Formula (I) or pharmaceutically acceptable salts thereof.

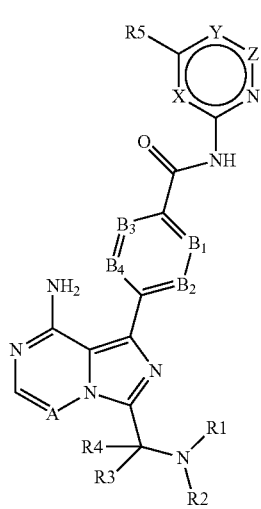

Formula (I)

In this formula the substituents are defined as
X is CH, N, O or S;
Y is C(R6), N, O or S;
Z is CH, N or a bond;
A is CH or N;
B1 is N or C(R7);
B2 is N or C(R8);
B3 is N or C(R9);
B4 is N or C(R10);
R1 is R11C(O), R12S(O), R13SO$_2$ or (1-6C)alkyl optionally substituted with R14;
R2 is H, (1-3C)alkyl or (3-7C)cycloalkyl;
R3 is H, (1-6C)alkyl or (3-7C)cycloalkyl); or
R2 and R3 form, together with the N and C atom they are attached to, a (3-7C)heterocycloalkyl optionally substituted with one or more fluorine, hydroxyl, (1-3C)alkyl, (1-3C)alkoxy or oxo;
R4 is H or (1-3C)alkyl;
R5 is H, halogen, cyano, (1-4C)alkyl, (1-3C)alkoxy, (3-6C)cycloalkyl; all alkyl groups of R5 are optionally substituted with one or more halogen; or R5 is (6-10C)aryl or (2-6C)heterocycloalkyl;
R6 is H or (1-3C)alkyl; or
R5 and R6 together may form a (3-7C)cycloalkenyl, or (2-6C)heterocycloalkenyl; each optionally substituted with (1-3C)alkyl, or one or more halogen;
R7 is H, halogen or (1-3C)alkoxy;
R8 is H or (1-3C)alkyl; or
R7 and R8 form, together with the carbon atom they are attached to, a (6-10C)aryl or (1-9C)heteroaryl;
R9 is H, halogen or (1-3C)alkoxy;
R10 is H, halogen, or (1-3C)alkoxy;
R11 is independently selected from a group consisting of (1-6C)alkyl, (2-6C)alkenyl and (2-6C)alkynyl each alkyl, alkenyl or alkynyl optionally substituted with one or more groups selected from hydroxyl, (1-4C)alkyl, (3-7C)cycloalkyl, [(1-4C)alkyl]amino, di[(1-4C)alkyl]amino, (1-3C)alkoxy, (3-7C)cycloalkoxy, (6-10C)aryl or (3-7C)heterocycloalkyl; or
R11 is (1-3C)alkyl-C(O)—S-(1-3C)alkyl; or
R11 is (1-5C)heteroaryl optionally substituted with one or more groups selected from halogen or cyano.
R12 and R13 are independently selected from a group consisting of (2-6C)alkenyl or (2-6C)alkynyl both optionally substituted with one or more groups selected from hydroxyl, (1-4C)alkyl, (3-7C)cycloalkyl, [(1-4C)alkyl]amino, di[(1-4C)alkyl]amino, (1-3C)alkoxy, (3-7C)cycloalkoxy, (6-10C)aryl, or (3-7C)heterocycloalkyl; or
(1-5C)heteroaryl optionally substituted with one or more groups selected from halogen or cyano;
R14 is independently selected from a group consisting of halogen, cyano or (2-6C)alkenyl or (2-6C)alkynyl both optionally substituted with one or more groups selected from hydroxyl, (1-4C)alkyl, (3-7C)cycloalkyl, [(1-4C)alkyl]amino, di[(1-4C)alkyl]amino, (1-3C)alkoxy, (3-7C)cycloalkoxy, (6-10C)aryl, (1-5C)heteroaryl or (3-7C)heterocycloalkyl.

With the proviso that:
0 to 2 atoms of X, Y, Z can simultaneously be a heteroatom;
when one atom selected from X, Y is O or S, then Z is a bond and the other atom selected from X, Y cannot be O or S;
when Z is CH or N then Y is C(R6) or N and X is CH or N;
0 to 2 atoms of B1, B2, B3 and B4 are N.

The terms as used herein refer to the following:
(1-2C)Alkyl means an alkyl group having 1 to 2 carbon atoms, being methyl or ethyl.
(1-3C)Alkyl means a branched or unbranched alkyl group having 1-3 carbon atoms, being methyl, ethyl, propyl or isopropyl.
(1-4C)Alkyl means a branched or unbranched alkyl group having 1-4 carbon atoms, being methyl, ethyl, propyl, isopropyl, butyl, isobutyl, sec-butyl and tert-butyl, (1-3C)alkyl groups being preferred.
(1-5C)Alkyl means a branched or unbranched alkyl group having 1-5 carbon atoms, for example methyl, ethyl, propyl, isopropyl, butyl, isobutyl, sec-butyl, tert-butyl, pentyl and isopentyl, (1-4C)alkyl groups being preferred.
(1-6C)Alkyl means a branched or unbranched alkyl group having 1-6 carbon atoms, for example methyl, ethyl, propyl, isopropyl, butyl, tert-butyl, n-pentyl and n-hexyl. (1-5C) alkyl groups are preferred, (1-4C)alkyl being most preferred.
(1-2C)Alkoxy means an alkoxy group having 1-2 carbon atoms, the alkyl moiety having the same meaning as previously defined.
(1-3C)Alkoxy means an alkoxy group having 1-3 carbon atoms, the alkyl moiety having the same meaning as previously defined. (1-2C)alkoxy groups are preferred.
(1-4C)Alkoxy means an alkoxy group having 1-4 carbon atoms, the alkyl moiety having the same meaning as previously defined. (1-3C)alkoxy groups are preferred, (1-2C) alkoxy groups being most preferred.
(2-4C)Alkenyl means a branched or unbranched alkenyl group having 2-4 carbon atoms, such as ethenyl, 2-propenyl, isobutenyl or 2-butenyl.
(2-6C)Alkenyl means a branched or unbranched alkenyl group having 2-6 carbon atoms, such as ethenyl, 2-butenyl, and n-pentenyl. (2-4C)alkenyl groups are preferred.
(2-4C)Alkynyl means a branched or unbranched alkynyl group having 2-4 carbon atoms, such as ethynyl, 2-propynyl or 2-butynyl.
(2-6C)Alkynyl means a branched or unbranched alkynyl group having 2-6 carbon atoms, such as ethynyl, propynyl, n-butynyl, n-pentynyl, isopentynyl, isohexynyl or n-hexynyl. (2-4C)alkynyl groups are preferred.
(3-6C)Cycloalkyl means a cycloalkyl group having 3-6 carbon atoms, being cyclopropyl, cyclobutyl, cyclopentyl or cyclohexyl.

(3-7C)Cycloalkyl means a cycloalkyl group having 3-7 carbon atoms, being cyclopropyl, cyclobutyl, cyclopentyl, cyclohexyl or cycloheptyl.

(2-6C)Heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom. Preferred heteroatoms are N or O. Preferred are piperidine, morpholine, pyrrolidine and piperazine. Most preferred (2-6C)heterocycloalkyl is pyrrolidine. The heterocycloalkyl group may be attached via a heteroatom if feasible.

(3-7C)Heterocycloalkyl means a heterocycloalkyl group having 3-7 carbon atoms, preferably 3-5 carbon atoms, and one or two heteroatoms selected from N, O and/or S. Preferred heteroatoms are N or O. Preferred (3-7C) heterocycloalkyl groups are azetidinyl, pyrrolidinyl, piperidinyl, homopiperidinyl or morpholinyl. More preferred (3-7C) heterocycloalkyl groups are piperidine, morpholine and pyrrolidine. The heterocycloalkyl group may be attached via a heteroatom if feasible.

(3-7C)Cycloalkoxy means a cycloalkyl group having 3-7 carbon atoms, with the same meaning as previously defined, attached via a ring carbon atom to an exocyclic oxygen atom.

(6-10C)Aryl means an aromatic hydrocarbon group having 6-10 carbon atoms, such as phenyl, naphthyl, tetrahydronaphthyl or indenyl. The preferred (6-10C)aryl group is phenyl.

(1-5C)Heteroaryl means a substituted or unsubstituted aromatic group having 1-5 carbon atoms and 1-4 heteroatoms selected from N, O and/or S. The (1-5C)heteroaryl may optionally be substituted. Preferred (1-5C)heteroaryl groups are tetrazolyl, imidazolyl, thiadiazolyl, pyridyl, pyrimidyl, triazinyl, thienyl or furyl, more preferred (1-5C)heteroaryl is pyrimidyl.

(1-9C)Heteroaryl means a substituted or unsubstituted aromatic group having 1-9 carbon atoms and 1-4 heteroatoms selected from N, O and/or S. The (1-9C)heteroaryl may optionally be substituted. Preferred (1-9C)heteroaryl groups are quinoline, isoquinoline and indole.

[(1-4C)Alkyl]amino means an amino group, monosubstituted with an alkyl group containing 1-4 carbon atoms having the same meaning as previously defined. Preferred [(1-4C)alkyl]amino group is methylamino.

Di[(1-4C)alkyl]amino means an amino group, disubstituted with alkyl group(s), each containing 1-4 carbon atoms and having the same meaning as previously defined. Preferred di[(1-4C)alkyl]amino group is dimethylamino.

Halogen means fluorine, chlorine, bromine or iodine.

(1-3C)Alkyl-C(O)—S-(1-3C)alkyl means an alkyl-carbonyl-thio-alkyl group, each of the alkyl groups having 1 to 3 carbon atoms with the same meaning as previously defined.

(3-7C)Cycloalkenyl means a cycloalkenyl group having 3-7 carbon atoms, preferably 5-7 carbon atoms. Preferred (3-7C)cycloalkenyl groups are cyclopentenyl or cyclohexenyl. Cyclohexenyl groups are most preferred.

(2-6C)Heterocycloalkenyl means a heterocycloalkenyl group having 2-6 carbon atoms, preferably 3-5 carbon atoms; and 1 heteroatom selected from N, O and/or S. Preferred (2-6C)heterocycloalkenyl groups are oxycyclohexenyl and azacyclohexenyl groups.

In the above definitions with multifunctional groups, the attachment point is at the last group.

When, in the definition of a substituent, it is indicated that "all of the alkyl groups" of said substituent are optionally substituted, this also includes the alkyl moiety of an alkoxy group.

A circle in a ring of Formula (I) indicates that the ring is aromatic.

Depending on the ring formed, the nitrogen, if present in X or Y, may carry a hydrogen.

The term "substituted" means that one or more hydrogens on the designated atom/atoms is/are replaced with a selection from the indicated group, provided that the designated atom's normal valency under the existing circumstances is not exceeded, and that the substitution results in a stable compound.

Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

Aspects of the Invention

In one aspect the invention relates to a compound according to Formula (I) wherein B1 is C(R7); B2 is C(R8); B3 is C(R9) and B4 is C(R10).

In another aspect the invention relates to a compound according to Formula (I) wherein B1 is C(R7); B2 is C(R8); B3 is C(R9); B4 is C(R10); R7, R9, and R10 each are H; and R8 is selected from a group consisting of hydrogen and methyl.

In one aspect the invention relates to a compound according to Formula (I) wherein R8 is hydrogen or methyl, in particular R8 is hydrogen.

In another aspect the invention relates to a compound according to Formula (I) wherein R7 is hydrogen, fluorine or (1-3C)alkoxy. In particular, R7 is hydrogen, fluorine or methoxy. Even more particularly, an aspect of the invention relates to a compound according to Formula (I) wherein R7 is hydrogen.

In yet another aspect the invention relates to a compound according to Formula (I) wherein R9 is hydrogen, fluorine or (1-3C)alkoxy. In particular, R9 is hydrogen, fluorine or methoxy. Even more particularly, an aspect of the invention relates to a compound according to Formula (I) wherein R9 is hydrogen.

In another aspect the invention relates to a compound according to Formula (I) wherein R10 is hydrogen fluorine or (1-3C)alkoxy. In particular, R10 is hydrogen, fluorine or methoxy. Even more particularly, an aspect of the invention relates to a compound according to Formula (I) wherein R10 is hydrogen.

In still another aspect the invention relates to a compound according to Formula (I) wherein R7 and R8 form, together with the carbon atom they are attached to, an indole or quinoline or naphthyl.

In another aspect the invention relates to a compound according to Formula (I) wherein B1 is C(R7); B2 is C(R8); B3 is C(R9); B4 is C(R10) and R7, R8, R9, and R10 each are H;

In yet another aspect the invention relates to a compound according to Formula (I) wherein R4 is hydrogen or methyl. In particular, R4 is hydrogen.

In still another aspect the invention relates to a compound according to Formula (I) wherein A is N.

In another aspect the invention relates to a compound according of Formula (I) wherein A is CH.

In another aspect the invention relates to a compound according to Formula (I) wherein the ring containing X, Y and Z is selected from a group consisting of pyridyl, pyrimidyl, pyridazyl, triazinyl, thiazolyl, oxazolyl, and isoxazolyl. In particular, the invention relates to a compound according to Formula (I) wherein the ring containing X, Y and Z is selected from a group consisting of pyridyl, pyrimidyl and thiazolyl. The definition of R5 and R6 is independent from the selection of X, Y, and Z. The place of attachment of R5 and optionally of R6 to these heteroaryl rings follows from Formula (I).

The invention further relates to a compound according to Formula (I) wherein R5 is selected from a group consisting of hydrogen, halogen, cyano, (1-4C)alkyl, (1-3C)alkoxy and (3-6C)cycloalkyl. All of the alkyl groups of R5 are optionally substituted with one or more halogen. In particular, the (1-4C)alkyl group in R5 is optionally substituted with one or more halogen.

In another aspect the invention relates to a compound according to Formula (I) wherein R5 is selected from a group consisting of hydrogen, fluorine, chlorine, (1-3C)alkyl and (1-2C)alkoxy, all of the alkyl groups of R5 are optionally substituted with one or more halogen. In particular, the (1-3C)alkyl group in R5 is optionally substituted with one or more fluoro. Even more particularly, the invention relates to a compound according to Formula (I) wherein R5 is hydrogen, fluorine, methyl, ethyl, propyl, methoxy or trifluoromethyl.

In yet another aspect the invention relates to a compound according to Formula (I) wherein R5 is pyrrolidine or phenyl.

In another aspect, the invention relates to a compound according to Formula (I) wherein R6 is hydrogen or (1-3C) alkyl, preferably R6 is hydrogen.

In yet another aspect the invention relates to a compound according to Formula (I) wherein R5 and R6 together form a (3-7C)cycloalkenyl or a (2-6C)heterocycloalkenyl both optionally substituted with (1-3C)alkyl or one or more halogen. In particular, (3-7C)cycloalkenyl groups are cyclohexenyl and cyclopentenyl. In particular, (2-6C)heterocycloalkenyl groups are azacyclohexenyl and oxycyclohexenyl. Even more in particularly, the invention relates to a compound according to Formula (I) wherein the (3-7C) cycloalkenyl in R5 is cyclohexenyl.

In another aspect, the invention relates to a compound according to Formula (I) wherein R2 is hydrogen or (1-3C) alkyl. In particular, R2 is hydrogen or methyl. R2 is hydrogen being most preferred.

In yet another aspect the invention relates to a compound according to Formula (I) wherein R3 is (1-6C)alkyl. In particular, R3 is (1-3C)alkyl. R3 is methyl being most preferred.

In another aspect the invention relates to a compound according to Formula (I) wherein R3 is (3-7C)cycloalkyl.

In another aspect the invention relates to a compound according to Formula (I) wherein R2 is hydrogen or (1-3C) alkyl and R3 is (1-6C)alkyl. In particular, R2 is hydrogen or methyl and R3 is (1-3C)alkyl. Even more particularly, the invention relates to a compound according to Formula (I) wherein R2 is hydrogen and R3 is methyl.

In yet another aspect the invention relates to a compound according to Formula (I) wherein R2 or R3 are independently selected from a group consisting of cyclopropyl, cyclobutyl and cyclopentyl.

In another aspect the invention relates to a compound of Formula (I) wherein, R2 and R3 form, together with the N and C atom they are attached to, a (3-7C)heterocycloalkyl optionally substituted with one or more halogen, hydroxyl, (1-3C)alkyl. In particular, R2 and R3 form, together with the N and C atom they are attached to, an azetidinyl, pyrrolidinyl, piperidinyl, homopiperidinyl or morpholinyl ring each optionally substituted with one or more halogen, hydroxyl, (1-3C)alkyl, (1-3C)alkoxy or oxo, preferred halogen substituent being fluoro.

In yet another aspect the invention relates to a compound of Formula (I) wherein, R2 and R3 form, together with the N and C atom they are attached to, an azetidinyl, pyrrolidinyl, piperidinyl, homopiperidinyl or morpholinyl ring each optionally substituted with fluoro, hydroxyl, (1-3C)alkyl, (1-3C)alkoxy or oxo. In particular, R2 and R3, together with the N and C atom they are attached to, form a pyrrolidinyl, piperidinyl, morpholinyl or homopiperidinyl ring.

In yet another aspect the invention relates to a compound according to Formula (I) wherein, R1 is R11C(O) and R11 is (1-6C)alkyl, (2-6C)alkenyl or (2-6C)alkynyl each optionally independently substituted with one or more groups selected from hydroxyl, (1-4C)alkyl, (3-7C)cycloalkyl, (3-7C)heterocycloalkyl, [(1-4C)alkyl]amino, di[(1-4C) alkyl]amino, (1-3C)alkoxy, (3-7C)cycloalkoxy, (6-10C)aryl, (1-5C)heteroaryl or (1-3C)alkyl-S—C(O)-(1-3C)alkyl. In particular, the (1-5C)heteroaryl group is pyrimidyl or triazinyl optionally substituted with one or more groups selected from halogen or cyano. In particular, the (3-7C)heterocycloalkyl is pyrrolidinyl. Even more particularly, the invention relates to a compound according to Formula (I) wherein the (3-7C)cycloalkyl substituent of R11 is cyclopropyl. In particular, the (6-10C)aryl substituent of R11 is phenyl.

In yet another aspect the invention relates to a compound according to Formula (I) wherein,
R1 is C(O)R11 and R11 is (2-6C)alkenyl or (2-6C)alkynyl each optionally substituted with one or more groups selected from hydroxyl, (1-4C)alkyl, (3-7C)cycloalkyl, (3-7C)heterocycloalkyl, (di)[(1-4C)alkyl]amino, (1-3C)alkoxy or (3-7C)cycloalkoxy. In particular, the (3-7C)heterocycloalkyl substituent of R11 is pyrrolidinyl and the (3-7C)cycloalkyl substituent of R11 is cyclopropyl.

In another aspect the invention relates to a compound according to Formula (I) wherein, R1 is C(O)R11 and R11 is (2-4C)alkenyl or (2-4C)alkynyl each optionally substituted with one or more groups selected from (1-4C)alkyl, (3-7C)cycloalkyl, (3-7C)heterocycloalkyl, (di)[(1-4C)alkyl] amino or (1-3C)alkoxy. In particular, the (3-7C)heterocycloalkyl substituent of R11 is pyrrolidinyl and the (3-7C) cycloalkyl substituent is cyclopropyl. Even more particularly, R11 is (2-4C)alkenyl or (2-4C)alkynyl each optionally substituted with one or more groups selected from methyl, ethyl, cyclopropyl, pyrrolidinyl, dimethylamino, methoxy or ethoxy.

In a further aspect the invention relates to compounds according to Formula (I) wherein R1 is C(O)R11 wherein R11 is (1-5C)heteroaryl optionally substituted with one or more groups selected from halogen or cyano. In particular, the (1-5C)heteroaryl substituent is pyrimidyl or triazinyl, pyrimidyl rings being preferred, optionally substituted with one or more groups selected from halogen or cyano. In particular, the halogen substituent is chlorine.

In another aspect, the invention relates to compounds according to Formula (I) wherein R1 is R13SO$_2$, wherein R13 is (2-6C)alkenyl or (2-6C)alkynyl. In particular, R13 is (2-4C)alkenyl. Even more particularly, R13 is ethenyl.

In another aspect, the invention relates to compounds according to Formula (I) wherein R1 is R12S(O), wherein R12 is (2-6C)alkenyl or (2-6C)alkynyl. In particular, R13 is (2-4C)alkenyl. Even more particularly, R12 is ethenyl.

In yet another aspect, the invention relates to compounds according to Formula (I) wherein R1 is (1-3C)alkyl optionally substituted with R14 wherein R14 is (2-4C)alkenyl or (2-4C)alkynyl.

In yet another aspect the invention relates to a compound according to Formula (I) selected from the group consisting of (S)-4-(3-(1-Acryloylpyrrolidin-2-yl)-8-aminoimidazo[1,5-a]pyrazin-1-yl)-N-(pyridin-2-yl)benzamide,
(S,E)-4-(8-amino-3-(1-(4-(pyrrolidin-1-yl)but-2-enoyl)pyrrolidin-2-yl)imidazo[1,5-a]pyrazin-1-yl)-N-(pyridin-2-yl)benzamide,
(S,E)-4-(8-Amino-3-(1-(4-(dimethylamino)but-2-enoyl)pyrrolidin-2-yl)imidazo[1,5-a]pyrazin-1-yl)-N-(pyridin-2-yl)benzamide,
(S,E)-4-(8-amino-3-(1-(4-methoxybut-2-enoyl)pyrrolidin-2-yl)imidazo[1,5-a]pyrazin-1-yl)-N-(pyridin-2-yl)benzamide,
(S)-4-(8-amino-3-(1-(2-chloropyrimidine-4-carbonyl)pyrrolidin-2-yl)imidazo[1,5-a]pyrazin-1-yl)-N-(pyridin-2-yl)benzamide,
(S)-4-(8-amino-3-(1-but-2-ynoylpyrrolidin-2-yl)imidazo[1,5-a]pyrazin-1-yl)-N-(pyridin-2-yl)benzamide,
(S,E)-4-(8-Amino-3-(1-(4-(dimethylamino)but-2-enoyl)pyrrolidin-2-yl)imidazo[1,5-a]pyrazin-1-yl)-N-(4-fluoropyridin-2-yl)benzamide,
(S)-4-(8-Amino-3-(1-but-2-ynoylpyrrolidin-2-yl)imidazo[1,5-a]pyrazin-1-yl)-N-(4-methylpyridin-2-yl)benzamide,
(S,E)-4-(8-Amino-3-(1-(4-methoxybut-2-enoyl)pyrrolidin-2-yl)imidazo[1,5-a]pyrazin-1-yl)-N-(4-propylpyridin-2-yl)benzamide,
(S)-4-(8-Amino-3-(1-but-2-ynoylpyrrolidin-2-yl)imidazo[1,5-a]pyrazin-1-yl)-N-(4-(trifluoromethyl)pyridin-2-yl)benzamide,
(S,E)-4-(8-Amino-3-(1-(4-methoxybut-2-enoyl)pyrrolidin-2-yl)imidazo[1,5-a]pyrazin-1-yl)-N-(4-ethylpyridin-2-yl)benzamide,
(S)-4-(8-Amino-3-(1-but-2-ynoylpyrrolidin-2-yl)imidazo[1,5-a]pyrazin-1-yl)-N-(4,5,6,7-tetrahydrobenzo[d]thiazol-2-yl)benzamide,
(S)-4-(3-(1-Acryloylpyrrolidin-2-yl)-8-aminoimidazo[1,5-a]pyrazin-1-yl)-2-fluoro-N-(pyridin-2-yl)benzamide,
(S)-4-(3-(1-Acryloylpyrrolidin-2-yl)-8-aminoimidazo[1,5-a]pyrazin-1-yl)-2-methoxy-N-(pyridin-2-yl)benzamide,
(S,E)-4-(8-Amino-3-(1-(4-(dimethylamino)but-2-enoyl)pyrrolidin-2-yl)imidazo[1,5-a]pyrazin-1-yl)-N-(thiazol-2-yl)benzamide,
(S,E)-4-(8-Amino-3-(1-(4-methoxybut-2-enoyl)piperidin-2-yl)imidazo[1,5-a]pyrazin-1-yl)-N-(pyridin-2-yl)benzamide,
(S)-4-(3-(1-Acryloylpiperidin-2-yl)-8-aminoimidazo[1,5-a]pyrazin-1-yl)-N-(4-fluoropyridin-2-yl)benzamide,
(S)-4-(3-(1-Acryloylpiperidin-2-yl)-8-aminoimidazo[1,5-a]pyrazin-1-yl)-N-(4-cyanopyridin-2-yl)benzamide,
(S)-4-(8-Amino-3-(1-(vinylsulfonyl)piperidin-2-yl)imidazo[1,5-a]pyrazin-1-yl)-N-(4-(trifluoromethyl)pyridin-2-yl)benzamide,
(S)-4-(3-(1-Acryloylpiperidin-2-yl)-8-aminoimidazo[1,5-a]pyrazin-1-yl)-N-(pyrimidin-2-yl)benzamide,
(S)-4-(3-(1-Acryloylpiperidin-2-yl)-8-aminoimidazo[1,5-a]pyrazin-1-yl)-N-(4-methylpyrimidin-2-yl)benzamide,
(S)-4-(8-Amino-3-(1-but-2-ynoylpiperidin-2-yl)imidazo[1,5-a]pyrazin-1-yl)-N-(pyrimidin-4-yl)benzamide,
(S)-4-(8-Amino-3-(1-but-2-ynoylpiperidin-2-yl)imidazo[1,5-a]pyrazin-1-yl)-N-(pyridazin-3-yl)benzamide,
(S)-4-(8-Amino-3-(1-but-2-ynoylpiperidin-2-yl)imidazo[1,5-a]pyrazin-1-yl)-N-(isoxazol-3-yl)benzamide,
(S,E)-4-(8-Amino-3-(1-(4-methoxybut-2-enoyl)piperidin-2-yl)imidazo[1,5-a]pyrazin-1-yl)-N-(5-ethylthiazol-2-yl)benzamide,
(S)-4-(3-(1-Acryloylpiperidin-2-yl)-8-aminoimidazo[1,5-a]pyrazin-1-yl)-2-fluoro-N-(4-propylpyridin-2-yl)benzamide,
(S,E)-4-(8-Amino-3-(1-(4-(dimethylamino)but-2-enoyl)piperidin-2-yl)imidazo[1,5-a]pyrazin-1-yl)-2-methoxy-N-(4-propylpyridin-2-yl)benzamide,
4-(8-Amino-3-((S)-1-but-2-ynoylpiperidin-2-yl)imidazo[1,5-a]pyrazin-1-yl)-3-methyl-N-(pyridin-2-yl)benzamide,
4-(3-(Acrylamidomethyl)-8-aminoimidazo[1,5-a]pyrazin-1-yl)-N-(pyridin-2-yl)benzamide,
(S)-4-(8-Amino-3-(1-but-2-ynamidoethyl)imidazo[1,5-a]pyrazin-1-yl)-N-(pyridin-2-yl)benzamide,
(S)—S-2-(2-(8-Amino-1-(4-(pyridin-2-ylcarbamoyl)phenyl)imidazo[1,5-a]pyrazin-3-yl)pyrrolidin-1-yl)-2-oxoethyl ethanethioate,
(S)-4-(8-Amino-3-(1-(4-hydroxy-4-methylpent-2-ynoyl)pyrrolidin-2-yl)imidazo[1,5-a]pyrazin-1-yl)-N-(pyridin-2-yl)benzamide,
(S)-4-(8-Amino-3-(1-(6-chloropyrimidine-4-carbonyl)pyrrolidin-2-yl)imidazo[1,5-a]pyrazin-1-yl)-N-(pyridin-2-yl)benzamide,
(S)-4-(8-Amino-3-(1-pent-2-ynoylpyrrolidin-2-yl)imidazo[1,5-a]pyrazin-1-yl)-N-(pyridin-2-yl)benzamide,
(S)-4-(8-Amino-3-(1-(3-cyclopropylpropioloyl)pyrrolidin-2-yl)imidazo[1,5-a]pyrazin-1-yl)-N-(pyridin-2-yl)benzamide,
(S)-4-(8-Amino-3-(1-hex-2-ynoylpyrrolidin-2-yl)imidazo[1,5-a]pyrazin-1-yl)-N-(pyridin-2-yl)benzamide,
4-(3-(1-Acryloylazepan-2-yl)-8-aminoimidazo[1,5-a]pyrazin-1-yl)-N-(pyridin-2-yl)benzamide,
(R)-4-(8-Amino-3-(4-but-2-ynoylmorpholin-3-yl)imidazo[1,5-a]pyrazin-1-yl)-N-(pyridin-2-yl)benzamide,
(S)-4-(8-amino-3-(1-(N-methylbut-2-ynamido)ethyl)imidazo[1,5-a]pyrazin-1-yl)-N-(4-(trifluoromethyl)pyridin-2-yl)benzamide,
(S)-4-(8-Amino-3-(1-(4-(dimethylamino)but-2-ynoyl)pyrrolidin-2-yl)imidazo[1,5-a]pyrazin-1-yl)-N-(pyridin-2-yl)benzamide,
(S)-4-(8-Amino-3-(1-(4-methoxybut-2-ynoyl)pyrrolidin-2-yl)imidazo[1,5-a]pyrazin-1-yl)-N-(pyridin-2-yl)benzamide,
(S)-4-(3-(1-acryloylpyrrolidin-2-yl)-8-aminoimidazo[1,5-a]pyrazin-1-yl)-N-(4-fluoropyridin-2-yl)benzamide,
(S)-4-(3-(1-acryloylpyrrolidin-2-yl)-8-aminoimidazo[1,5-a]pyrazin-1-yl)-N-(4-(pyrrolidin-1-yl)pyridin-2-yl)benzamide,
(S)-4-(8-amino-3-(1-but-2-ynoylpiperidin-2-yl)imidazo[1,5-a]pyrazin-1-yl)-N-(4-fluoropyridin-2-yl)benzamide,
(S)-4-(8-amino-3-(1-but-2-ynoylpiperidin-2-yl)imidazo[1,5-a]pyrazin-1-yl)-N-(pyridin-2-yl)benzamide,
(S)-4-(3-(1-acryloylpiperidin-2-yl)-8-aminoimidazo[1,5-a]pyrazin-1-yl)-N-(pyridin-2-yl)benzamide,
(S)-4-(8-amino-3-(1-but-2-ynoylpyrrolidin-2-yl)imidazo[1,5-a]pyrazin-1-yl)-N-(4-propylpyridin-2-yl)benzamide,
(S,E)-4-(8-amino-3-(1-(4-methoxy-N-methylbut-2-enamido)ethyl)imidazo[1,5-a]pyrazin-1-yl)-N-(4-propylpyridin-2-yl)benzamide,
(S)-4-(8-amino-3-(1-(vinylsulfonyl)piperidin-2-yl)imidazo[1,5-a]pyrazin-1-yl)-N-(4-propylpyridin-2-yl)benzamide, (S)-4-(8-amino-3-(1-but-2-ynoylpyrrolidin-2-yl)imidazo[1,5-a]pyrazin-1-yl)-2-fluoro-N-(pyridin-2-yl)benzamide,
(S,E)-4-(8-amino-3-(1-(4-methoxybut-2-enoyl)pyrrolidin-2-yl)imidazo[1,5-a]pyrazin-1-yl)-N-(4-methoxypyridin-2-yl)benzamide,
(S,E)-4-(8-amino-3-(1-(4-methoxybut-2-enoyl)pyrrolidin-2-yl)imidazo[1,5-a]pyrazin-1-yl)-2-fluoro-N-(4-methoxypyridin-2-yl)benzamide,
(S,E)-4-(8-amino-3-(1-(4-methoxybut-2-enoyl)pyrrolidin-2-yl)imidazo[1,5-a]pyrazin-1-yl)-N-(4-fluoropyridin-2-yl)benzamide,
(S,E)-4-(8-amino-3-(1-(4-methoxybut-2-enoyl)piperidin-2-yl)imidazo[1,5-a]pyrazin-1-yl)-N-(isoxazol-3-yl)benzamide,
(S,E)-4-(8-amino-3-(1-(4-methoxybut-2-enoyl)piperidin-2-yl)imidazo[1,5-a]pyrazin-1-yl)-N-(pyrimidin-2-yl)benzamide,
4-(8-amino-3-((S)-1-(2-chloropyrimidine-4-carbonyl)piperidin-2-yl)imidazo[1,5-a]pyrazin-1-yl)-3-methyl-N-(pyridin-2-yl)benzamide,
(S,E)-4-(8-amino-3-(1-(4-methoxybut-2-enoyl)pyrrolidin-2-yl)imidazo[1,5-a]pyrazin-1-yl)-N-(4-methylpyridin-2-yl)benzamide,
(S,E)-4-(8-amino-3-(1-(4-methoxybut-2-enoyl)pyrrolidin-2-yl)imidazo[1,5-a]pyrazin-1-yl)-N-(4-isopropylpyridin-2-yl)benzamide,
(S,E)-4-(8-amino-3-(1-(4-(dimethylamino)but-2-enoyl)pyrrolidin-2-yl)imidazo[1,5-a]pyrazin-1-yl)-N-(4-methylpyridin-2-yl)benzamide,
(S)-4-(8-amino-3-(1-but-2-ynoylpyrrolidin-2-yl)imidazo[1,5-a]pyrazin-1-yl)-N-(thiazol-2-yl)benzamide,
(S)-4-(3-(1-acryloylpiperidin-2-yl)-8-aminoimidazo[1,5-a]pyrazin-1-yl)-N-(4-propylpyridin-2-yl)benzamide,
(S)-4-(3-(1-acryloylpyrrolidin-2-yl)-8-aminoimidazo[1,5-a]pyrazin-1-yl)-N-(4-(trifluoromethyl)pyridin-2-yl)benzamide,
(S)-4-(8-amino-3-(1-but-2-ynoylpiperidin-2-yl)imidazo[1,5-a]pyrazin-1-yl)-N-(4-(trifluoromethyl)pyridin-2-yl)benzamide,
(S)-4-(8-amino-3-(1-but-2-ynoylpiperidin-2-yl)imidazo[1,5-a]pyrazin-1-yl)-N-(4-propylpyridin-2-yl)benzamide,
(S,E)-4-(8-amino-3-(1-(4-(dimethylamino)but-2-enoyl)pyrrolidin-2-yl)imidazo[1,5-a]pyrazin-1-yl)-N-(4-isopropylpyridin-2-yl)benzamide,
4-(8-amino-3-((S)-1-(vinylsulfonyl)piperidin-2-yl)imidazo[1,5-a]pyrazin-1-yl)-3-methyl-N-(pyridin-2-yl)benzamide,
(S)-4-(8-amino-3-(1-but-2-ynoylpiperidin-2-yl)imidazo[1,5-a]pyrazin-1-yl)-2-fluoro-N-(4-propylpyridin-2-yl)benzamide,
4-(3-((S)-1-acryloylpiperidin-2-yl)-8-aminoimidazo[1,5-a]pyrazin-1-yl)-3-methyl-N-(pyridin-2-yl)benzamide,
(E)-4-(8-amino-3-((4-(dimethyl amino)but-2-enamido)methyl) imidazo[1,5-a]pyrazin-1-yl)-N-(pyridin-2-yl)benzamide,
(S)-4-(8-amino-3-(1-(2-chloro pyrimidine-4-carbonyl)pyrrolidin-2-yl)imidazo[1,5-a]pyrazin-1-yl)-N-(4-isopropylpyridin-2-yl)benzamide,
(S)-4-(8-amino-3-(1-(2-chloro pyrimidine-4-carbonyl)pyrrolidin-2-yl)imidazo[1,5-a]pyrazin-1-yl)-N-(4,5,6,7-tetrahydrobenzo[d]thiazol-2-yl)benzamide,
(S,E)-4-(8-amino-3-(1-(4-methoxybut-2-enoyl)piperidin-2-yl)imidazo[1,5-a]pyrazin-1-yl)-N-(pyridazin-3-yl)benzamide,
(S,E)-4-(8-amino-3-(1-(4-(dimethylamino)but-2-enoyl)piperidin-2-yl)imidazo[1,5-a]pyrazin-1-yl)-N-(pyridazin-3-yl)benzamide,
(S)-4-(8-amino-3-(1-(2-chloropyrimidine-4-carbonyl)piperidin-2-yl)imidazo[1,5-a]pyrazin-1-yl)-N-(pyridazin-3-yl)benzamide,
(S,E)-4-(8-amino-3-(1-(4-methoxy-N-methylbut-2-enamido)ethyl)imidazo[1,5-a]pyrazin-1-yl)-N-(4-(trifluoromethyl)pyridin-2-yl)benzamide,
(S,E)-4-(8-amino-3-(1-(4-(dimethylamino)-N-methylbut-2-enamido)ethyl)imidazo[1,5-a]pyrazin-1-yl)-N-(4-propylpyridin-2-yl)benzamide,
(S,E)-4-(8-amino-3-(1-(4-(pyrrolidin-1-yl)but-2-enoyl)pyrrolidin-2-yl)imidazo[1,5-a]pyrazin-1-yl)-N-(4-propylpyridin-2-yl)benzamide,
(S,E)-4-(8-amino-3-(1-(4-(dimethylamino)but-2-enoyl)piperidin-2-yl)imidazo[1,5-a]pyrazin-1-yl)-N-(pyridin-2-yl)benzamide,
(S)-4-(8-amino-3-(1-(2-chloropyrimidine-4-carbonyl)pyrrolidin-2-yl)imidazo[1,5-a]pyrazin-1-yl)-N-(4-propylpyridin-2-yl)benzamide,
(S)-4-(8-amino-3-(1-(2-chloropyrimidine-4-carbonyl)piperidin-2-yl)imidazo[1,5-a]pyrazin-1-yl)-N-(4-fluoropyridin-2-yl)benzamide,
(S,E)-4-(8-amino-3-(1-(4-methoxybut-2-enoyl)piperidin-2-yl)imidazo[1,5-a]pyrazin-1-yl)-N-(4-fluoropyridin-2-yl)benzamide,
(S,E)-4-(8-amino-3-(1-(4-methoxybut-2-enoyl)pyrrolidin-2-yl)imidazo[1,5-a]pyrazin-1-yl)-N-(4,5,6,7-tetrahydrobenzo[d]thiazol-2-yl)benzamide,
(S)-4-(8-amino-3-(1-(2-chloropyrimidine-4-carbonyl)pyrrolidin-2-yl)imidazo[1,5-a]pyrazin-1-yl)-2-methoxy-N-(pyridin-2-yl)benzamide,
(S)-4-(8-amino-3-(1-(2-chloropyrimidine-4-carbonyl)pyrrolidin-2-yl)imidazo[1,5-a]pyrazin-1-yl)-2-fluoro-N-(pyridin-2-yl)benzamide,
4-(8-amino-3-((S)-1-((E)-4-methoxybut-2-enoyl)piperidin-2-yl)imidazo[1,5-a]pyrazin-1-yl)-3-methyl-N-(pyridin-2-yl)benzamide,
(S,E)-4-(8-amino-3-(1-(4-methoxybut-2-enoyl)piperidin-2-yl)imidazo[1,5-a]pyrazin-1-yl)-N-(pyrimidin-4-yl)benzamide,
4-(8-amino-3-((S)-1-((E)-4-methoxybut-2-enoyl)pyrrolidin-2-yl)imidazo[1,5-a]pyrazin-1-yl)-3-methyl-N-(4-propylpyridin-2-yl)benzamide,
(S,E)-4-(8-amino-3-(1-(4-methoxybut-2-enoyl)piperidin-2-yl)imidazo[1,5-a]pyrazin-1-yl)-N-(4-methylpyrimidin-2-yl)benzamide,
(S)-4-(8-amino-3-(1-but-2-ynoylpiperidin-2-yl)imidazo[1,5-a]pyrazin-1-yl)-N-(4-methylpyrimidin-2-yl)benzamide,
(S)-4-(8-amino-3-(1-(2-chloropyrimidine-4-carbonyl)piperidin-2-yl)imidazo[1,5-a]pyrazin-1-yl)-N-(pyrimidin-2-yl)benzamide,
(S)-4-(8-amino-3-(1-methacryloylpyrrolidin-2-yl)imidazo[1,5-a]pyrazin-1-yl)-N-(pyridin-2-yl)benzamide,
(S)-4-(8-amino-3-(1-(2-(trifluoromethyl)acryloyl)pyrrolidin-2-yl)imidazo[1,5-a]pyrazin-1-yl)-N-(pyridin-2-yl)benzamide,
(S,E)-4-(8-amino-3-(1-but-2-enoylpyrrolidin-2-yl)imidazo[1,5-a]pyrazin-1-yl)-N-(pyridin-2-yl)benzamide,
(S)-4-(8-amino-3-(1-(cyanomethyl)pyrrolidin-2-yl)imidazo[1,5-a]pyrazin-1-yl)-N-(pyridin-2-yl)benzamide,
(E)-4-(8-amino-3-((4-methoxybut-2-enamido)methyl)imidazo[1,5-a]pyrazin-1-yl)-N-(pyridin-2-yl)benzamide,
(S)-4-(8-amino-3-(1-but-2-ynoylpyrrolidin-2-yl)imidazo[1,5-a]pyrazin-1-yl)-N-(4-(pyrrolidin-1-yl)pyridin-2-yl)benzamide,
(E)-4-(8-amino-3-(1-(4-methoxybut-2-enoyl)azepan-2-yl)imidazo[1,5-a]pyrazin-1-yl)-N-(pyridin-2-yl)benzamide, (S,E)-4-(8-amino-3-(1-(4-methoxybut-2-enoyl)pyrrolidin-2-yl)imidazo[1,5-a]pyrazin-1-yl)-N-(4-cyanopyridin-2-yl)benzamide, (S)-4-(8-amino-3-(1-but-2-ynoylpyrrolidin-2-yl)imidazo[1,5-a]pyrazin-1-yl)-2-methoxy-N-(pyridin-2-yl)benzamide, (S)-4-(3-(1-acrylamidoethyl)-8-aminoimidazo[1,5-a]pyrazin-1-yl)-N-(pyridin-2-yl)benzamide, (S)-4-(3-(1-acryloylpyrrolidin-2-yl)-8-aminoimidazo[1,5-a]pyrazin-1-yl)-N-(thiazol-2-yl)benzamide, (S)-4-(8-amino-3-(1-but-2-ynoylpyrrolidin-2-yl)imidazo[1,5-a]pyrazin-1-yl)-N-(4-isopropylpyridin-2-yl)benzamide, (S,E)-4-(8-amino-3-(1-(4-methoxybut-2-enoyl)pyrrolidin-2-yl)imidazo[1,5-a]pyrazin-1-yl)-2-methoxy-N-(pyridin-2-yl)benzamide, (S,E)-4-(8-amino-3-(1-cinnamoylpyrrolidin-2-yl)imidazo[1,5-a]pyrazin-1-yl)-N-(pyridin-2-yl)benzamide, (S)—N-(1-(8-amino-1-(4-(pyridin-2-ylcarbamoyl)phenyl)imidazo[1,5-a]pyrazin-3-yl)ethyl)-2-chloropyrimidine-4-carboxamide, (S)-4-(8-amino-3-(1-but-2-ynoylpyrrolidin-2-yl)imidazo[1,5-a]pyrazin-1-yl)-N-(4-fluoropyridin-2-yl)benzamide, (S)-4-(8-amino-3-(1-(2-chloropyrimidine-4-carbonyl)piperidin-2-yl)imidazo[1,5-a]pyrazin-1-yl)-N-(4-propylpyridin-2-yl)benzamide, (S,E)-4-(8-amino-3-(1-(4-methoxybut-2-enoyl)piperidin-2-yl)imidazo[1,5-a]pyrazin-1-yl)-N-(4-(trifluoromethyl)pyridin-2-yl)benzamide, (S)-4-(3-(1-acryloylpiperidin-2-yl)-8-aminoimidazo[1,5-a]pyrazin-1-yl)-N-(4-(trifluoromethyl)pyridin-2-yl)benzamide, (S)-4-(8-amino-3-(1-but-2-ynoylpiperidin-2-yl)imidazo[1,5-a]pyrazin-1-yl)-2-methoxy-N-(4-propylpyridin-2-yl)benzamide, (S,E)-4-(8-amino-3-(1-(4-methoxybut-2-enoyl)piperidin-2-yl)imidazo[1,5-a]pyrazin-1-yl)-2-methoxy-N-(4-propylpyridin-2-yl)benzamide, 4-(8-amino-3-(but-2-ynamidomethyl)imidazo[1,5-a]pyrazin-1-yl)-N-(pyridin-2-yl)benzamide, (S)-4-(8-amino-3-(1-(N-methylbut-2-ynamido)ethyl)imidazo[1,5-a]pyrazin-1-yl)-N-(4-propylpyridin-2-yl)benzamide, (S,E)-4-(8-amino-3-(1-(4-methoxybut-2-enoyl)piperidin-2-yl)imidazo[1,5-a]pyrazin-1-yl)-2-fluoro-N-(4-propylpyridin-2-yl)benzamide, (S)-4-(8-amino-3-(1-(2-chloropyrimidine-4-carbonyl)piperidin-2-yl)imidazo[1,5-a]pyrazin-1-yl)-N-(4-(trifluoromethyl)pyridin-2-yl)benzamide, (S)-4-(8-amino-3-(1-but-2-ynoylpiperidin-2-yl)imidazo[1,5-a]pyrazin-1-yl)-N-(5-ethylthiazol-2-yl)benzamide, (S)-4-(3-(1-acryloylpiperidin-2-yl)-8-aminoimidazo[1,5-a]pyrazin-1-yl)-N-(5-ethylthiazol-2-yl)benzamide, (S)-4-(8-amino-3-(1-(2-chloropyrimidine-4-carbonyl)piperidin-2-yl)imidazo[1,5-a]pyrazin-1-yl)-N-(5-ethylthiazol-2-yl)benzamide, (S)-4-(8-amino-3-(1-(2-chloropyrimidine-4-carbonyl)pyrrolidin-2-yl)imidazo[1,5-a]pyrazin-1-yl)-N-(4-(trifluoromethyl)pyridin-2-yl)benzamide, (R,E)-4-(8-amino-3-(4-(4-methoxybut-2-enoyl)morpholin-3-yl)imidazo[1,5-a]pyrazin-1-yl)-N-(pyridin-2-yl)benzamide, (S,E)-4-(8-amino-3-(1-(4-methoxybut-2-enoyl)piperidin-2-yl)imidazo[1,5-a]pyrazin-1-yl)-N-(4-propylpyridin-2-yl)benzamide, (S)-4-(3-(1-acryloylpyrrolidin-2-yl)-8-aminoimidazo[1,5-a]pyrazin-1-yl)-N-(4-cyanopyridin-2-yl)benzamide, (S)-4-(8-amino-3-(1-but-2-ynoylpyrrolidin-2-yl)imidazo[1,5-a]pyrazin-1-yl)-N-(4-methoxypyridin-2-yl)benzamide, (S)-4-(3-(1-acryloylpyrrolidin-2-yl)-8-aminoimidazo[1,5-a]pyrazin-1-yl)-N-(4-methylpyridin-2-yl)benzamide, (S)-4-(3-(1-acryloylpyrrolidin-2-yl)-8-aminoimidazo[1,5-a]pyrazin-1-yl)-N-(4-propylpyridin-2-yl)benzamide, (S)-4-(3-(1-acryloylpyrrolidin-2-yl)-8-aminoimidazo[1,5-a]pyrazin-1-yl)-N-(4-ethylpyridin-2-yl)benzamide, (S,E)-4-(8-amino-3-(1-(4-(dimethylamino)but-2-enoyl)pyrrolidin-2-yl)imidazo[1,5-a]pyrazin-1-yl)-N-(pyridin-2-yl)benzamide, (S,E)-4-(8-amino-3-(1-(4-methoxybut-2-enoyl)pyrrolidin-2-yl)imidazo[1,5-a]pyrazin-1-yl)-N-(4-(trifluoromethyl)pyridin-2-yl)benzamide, (S)-4-(8-amino-3-(1-(2-chloropyrimidine-4-carbonyl)pyrrolidin-2-yl)imidazo[1,5-a]pyrazin-1-yl)-N-(4-methylpyridin-2-yl)benzamide, (S)-4-(8-amino-3-(1-but-2-ynoylpyrrolidin-2-yl)imidazo[1,5-a]pyrazin-1-yl)-N-(4-cyanopyridin-2-yl)benzamide, (S)-4-(8-amino-3-(1-but-2-ynoylpyrrolidin-2-yl)imidazo[1,5-a]pyrazin-1-yl)-N-(4-ethylpyridin-2-yl)benzamide, (S)-4-(8-amino-3-(1-but-2-ynoylpyrrolidin-2-yl)imidazo[1,5-a]pyrazin-1-yl)-N-(4-phenylpyridin-2-yl)benzamide, and (S)-4-(3-(1-acryloylpyrrolidin-2-yl)-8-aminoimidazo[1,5-a]pyrazin-1-yl)-N-(4-phenylpyridin-2-yl)benzamide.

The invention also relates to those compounds wherein all specific definitions for R1 through R14 and all substituent groups in the various aspects of the inventions defined here above occur in any combination within the definition of the 6-5 membered fused pyridine ring compounds i.e. 8-amino-imidazo[1,5-a]pyrazine and 4-amino-imidazo[1,5-f][1,2,4]triazine compounds of Formula (I).

The 6-5 membered fused pyridine ring compounds like 8-amino-imidazo[1,5-a]pyrazine and 4-amino-imidazo[1,5-f][1,2,4]triazine compounds of the invention inhibit the Btk kinase activity. All compounds of the invention have an EC50 of 10 µM or lower.

In another aspect the invention relates to compounds of Formula (I) which have an EC50 of less than 100 nM. In yet another aspect the invention relates to compounds of Formula (I) which have an EC50 of less than 10 nM.

The term EC50 means the concentration of the test compound that is required for 50% inhibition of its maximum effect in vitro.

Inhibition of kinase activity can be measured using the Immobilized Metal Assay for Phosphochemicals (IMAP) assay. IMAP is a homogeneous fluorescence polarization (FP) assay based on affinity capture of phosphorylated peptide substrates. IMAP uses fluorescein-labeled peptide substrates that, upon phosphorylation by a protein kinase, bind to so-called IMAP nanoparticles, which are derivatized with trivalent metal complexes. Binding causes a change in the rate of the molecular motion of the peptide, and results in an increase in the FP value observed for the fluorescein label attached to the substrate peptide (Gaudet et al. A homogeneous fluorescence polarization assay adaptable for a range of protein serine/threonine and tyrosine kinases. J. Biomol. Screen (2003) 8, 164-175).

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

A discussion of prodrugs is provided in T. Higuchi and V. Stella, Pro-drugs as Novel Delivery Systems (1975) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and V. Stella, "Pro-drugs as Novel Delivery Systems," Vol. 14 of the A.C.S. Symposium Series, 1975, and in Bioreversible Carriers in Drug Design, ed. Edward B. Roche, American Pharmaceutical Association and Pergamon Press, 1987.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The present invention also relates to a pharmaceutical composition comprising 6-5 membered fused pyridine ring compounds like imidazopyrazine and imidazotriazine compounds or pharmaceutically acceptable salts thereof having the general Formula (I) in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a compound of Formula (I) in combination with one or more other drug(s). Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

The compounds according to the invention can be used in therapy.

A further aspect of the invention resides in the use of 6-5 membered fused pyridine ring compounds or a pharmaceutically acceptable salt thereof, having the general Formula (I) for the manufacture of a medicament to be used for the treatment of Btk-mediated diseases or Btk-mediated conditions.

A further aspect of the invention resides in the use of 6-5 membered fused pyridine ring compounds or a pharmaceutically acceptable salt thereof having the general Formula (I) for the manufacture of a medicament to be used for the treatment of chronic B cell disorders in which T cells play a prominent role. In yet another aspect the invention resides in the use of 6-5 membered fused pyridine ring compounds like 8-amino-imidazo[1,5-a]pyrazine and 4-amino-imidazo [1,5-f][1,2,4]triazine compounds having the general Formula (I) for the manufacture of a medicament to be used for the treatment of Btk-mediated diseases or conditions. These include, but are not limited to, the treatment of B cell lymphomas resulting from chronic active B cell receptor signaling.

Thus, the compounds according to the invention can be used in therapies to treat or prevent diseases Bruton's Tyrosine Kinase (Btk) mediated disorders. Btk mediated disorders or Btk mediated condition as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that can be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), autoimmune hematologic disorders (e.g. hemolytic anemia, aplasic anemia, idiopathic thrombocytopenia, and neutropenia), autoimmune gastritis, and autoimmune inflammatory bowel diseases (e.g. ulcerative colitis and Crohn's disease), host versus graft disease, allograft rejection, chronic thyroiditis, Graves' disease, scleroderma, diabetes (type I and type II), active hepatitis (acute and chronic), pancreatitis, primary biliary cirrhosis, myasthenia gravis, multiple sclerosis, systemic lupus erythematosus, psoriasis, atopic dermatitis, contact dermatitis, eczema, skin sunburns, vasculitis (e.g. Behcet's disease) chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that can be treated or prevented include, among others, allergies to foods, food additives, insect poisons, dust mites, pollen, animal materials and contact allergans, type I hypersensitivity allergic asthma, allergic rhinitis, allergic conjunctivitis.

Infectious diseases that can be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that can be treated or prevented include, among others, osteoporosis, osteoarthritis, traumatic arthritis, gouty arthritis and bone disorders related with multiple myeloma.

Proliferative diseases that can be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular compounds of the invention can be used for the treatment of B cell lymphomas resulting from chronic active B cell receptor signaling.

Inhibition of kinase activity can be measured using the Immobilized Metal Assay for Phosphochemicals (IMAP) assay. IMAP is a homogeneous fluorescence polarization (FP) assay based on affinity capture of phosphorylated peptide substrates. IMAP uses fluorescein-labeled peptide substrates that, upon phosphorylation by a protein kinase, bind to so-called IMAP nanoparticles, which are derivatized with trivalent metal complexes. Binding causes a change in the rate of the molecular motion of the peptide, and results in an increase in the FP value observed for the fluorescein label attached to the substrate peptide.

The Btk activity can also be determined in B cell lines such as Ramos cells or in primary cell assays, e.g PBMC or whole blood from human, monkey, rat or mouse or isolated splenocytes from monkey, rat or mouse. Inhibition of Btk activity can be investigated measuring anti-IgM-induced MIP1β production (Ramos, PBMC, splenocytes), $H_2O_2$-induced Btk and PLCγ2 phosphorylation (Ramos cells), or anti-IgM-induced B cell proliferation or CD86 expression on primary B cells (PBMC and splenocytes).

Regulation of Btk activity can also be determined on human, monkey, rat or mouse mast cells following activation FcεR induced degranulation, cytokine production and CD63 induced cell surface expression.

Furthermore, regulation of Btk activity can be determined on CD14+ monocytes differentiated following treatment with M-CSF to osteoclasts and activated with RANKL.

Activity of Btk inhibitors can be investigated in mouse splenocytes following administration in vivo. In a typical experiment mice can be euthanized 3 h following compound administration. Spleens can be extracted from the treated mice for splenocyte isolation. Splenocytes can be plated in 96 well culture plates and stimulated with anti-IgM, without further addition of compounds. Anti-IgM-induced B cell stimulation and inhibition thereof by Btk inhibitors can be measured by B cell proliferation, MIP1β production or CD86 expression on CD19+ splenocyte B cells.

Efficacy of Btk inhibitors can also be investigated in the mouse collagen induced arthritis model using a therapeutic protocol with start of treatment following onset of disease, measuring disease score, X-ray analysis of bone destruction, cartilage breakdown and histology of joints Efficacy of Btk inhibitors on the regulation of activated mast cells can be investigated in vivo using the passive cutaneous anaphylaxis model.

The effect of Btk inhibitors on bone resorption in vivo can be investigated using the rat OVX model. In this model ovariectomized animals develop symptoms of osteoporosis that may be regulated using a Btk inhibitor.

General Synthesis

The 8-amino-imidazo[1,5-a]pyrazine and 4-amino-imidazo[1,5-f][1,2,4]triazine derivatives of the present invention can be prepared by methods well known in the art of organic chemistry. See, for example, J. March, *'Advanced Organic Chemistry'* $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts *'Protective Groups in Organic Synthesis'* $3^{rd}$ Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

8-amino-imidazo[1,5-a]pyrazine compounds of Formula (I), wherein $R_1$-$R_5$ have the previously defined meanings, can be prepared by the general synthetic route shown in scheme I Scheme I

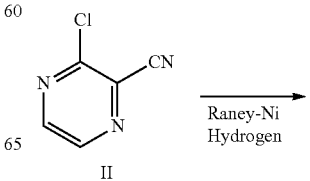

-continued

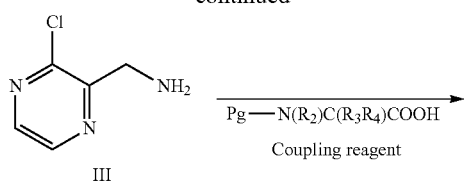

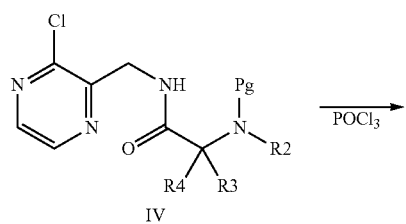

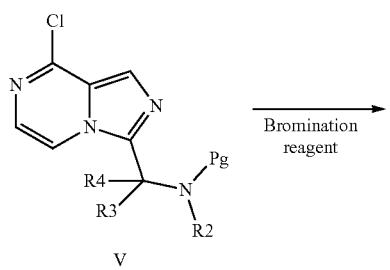

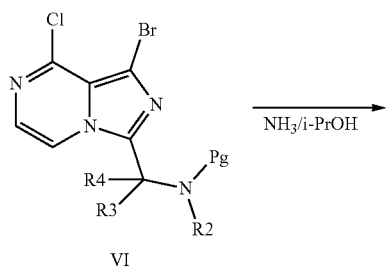

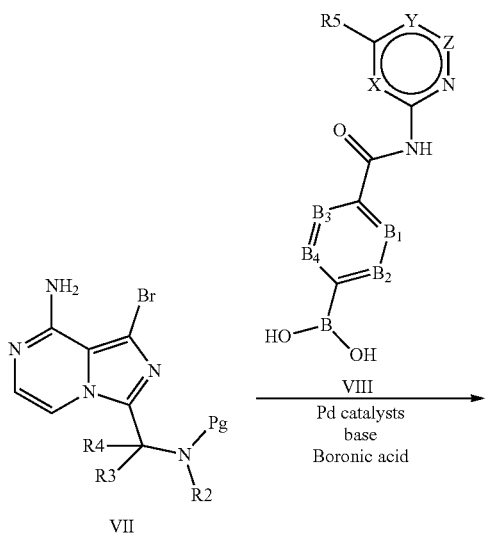

-continued

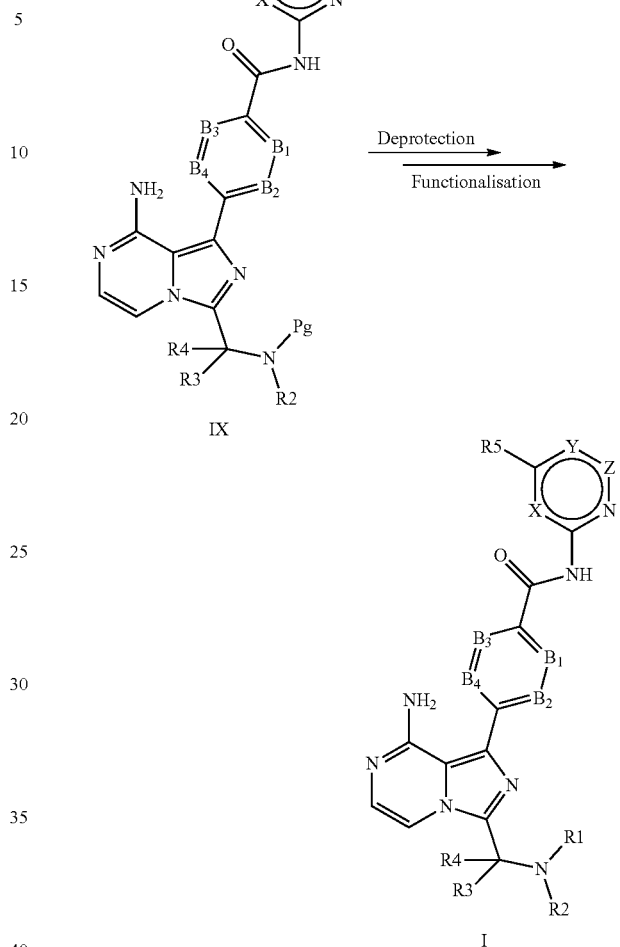

Reduction of 3-chloropyrazine-2-carbonitrile (II) can be accomplished by hydrogenation in the presence of a suitable catalysts system and solvent, for example Raney-Nickel to provide (3-chloropyrazin-2-yl)methanamine (III). This can then be reacted with an appropriately amine protected amino acid. The reaction of Cbz-N(R$_2$)CR$_3$R$_4$)COOH can be carried out in a solvent such as DMF, THF or DCM in the presence of a base such as DIPEA, N-methylmorpholine, 4-DMAP or triethylamine and in the presence of a coupling reagent such as PyBOP, TBTU, EDCI or HATU to form N-((3-chloropyrazin-2-yl)methyl)amide IV. Cyclisation of chloropyrazine IV can be performed using condensation reagents like phosphorous oxychloride under heating conditions to provide the 8-chloroimidazo[1,5-a]pyrazine derivatives V. Subsequent bromination can be accomplished using bromine or N-bromosuccinimide in a suitable solvent like DCM or DMF at appropriate temperature to obtain compounds of formula VI. 8-Aminoimidazo[1,5-a]pyrazine derivatives (VII) can be prepared from compounds VI using ammonia(gas) in isopropanol at elevated temperature in a pressure vessel (>4 atm). Compounds of formula IX can be prepared from compounds of formula VII using an appropriate boronic acid or pinacol ester (VIII), in the presence of a suitable palladium catalyst system and solvent, for example bis(diphenylphosphino)ferrocene palladium(II)

chloride complex or tetrakis(triphenylphosphine)palladium (0) in the presence of potassium carbonate in dioxane/water provide compounds of formula IX. Finally, cleaving the protective group of compounds with the formula IX give the unprotected amine which after functionalisation, using methods well known in the art, with appropriate warheads with previously defined meanings, provided compounds of Formula (I). An example of such protective strategy is the use of the benzyloxycarbonyl protecting group to protect the amine from the amino acids used, and after deprotection with 33% HBr/HOAc or conc. HCl gave the resulting amines.

The amino acids $HN(R_2)CR_3R_4)COOH$ are either commercially available or they can be readily prepared using methods well known to the skilled organic chemist, to introduce protecting groups like benzyloxycarbonyl or tert-butyloxycarbonyl.

Palladium catalysts and conditions to form either the pinacol esters or to couple the boronic acids or pinacol esters with the 1-bromoimidazo[1,5-a]pyrazin-8-amine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002.

4-Amino-imidazo[1,5-f][1,2,4]triazine compounds of Formula (I), wherein $R_1$-$R_5$ have the previously defined meanings, can be prepared by the general synthetic route shown in scheme II

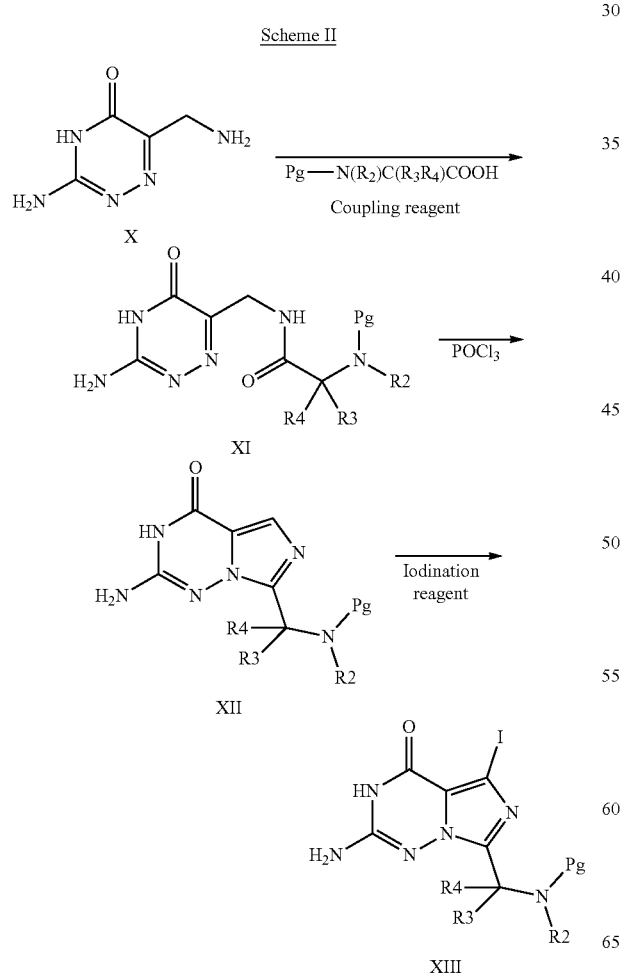
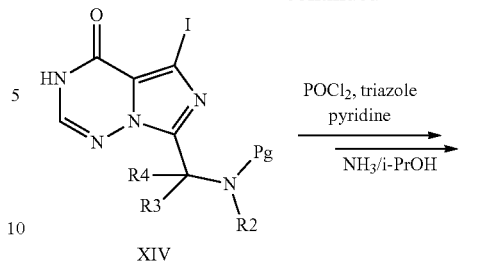
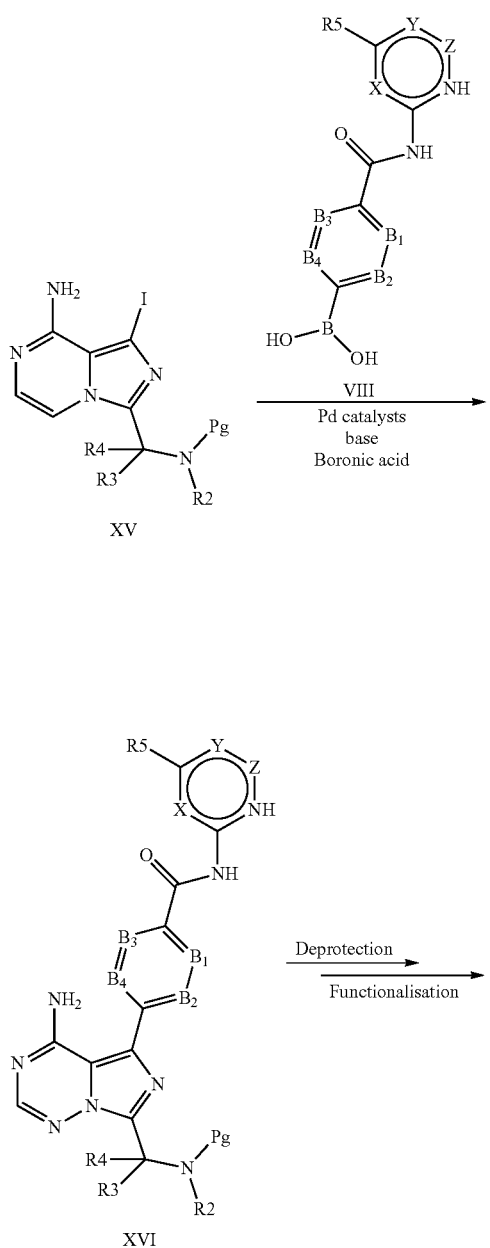

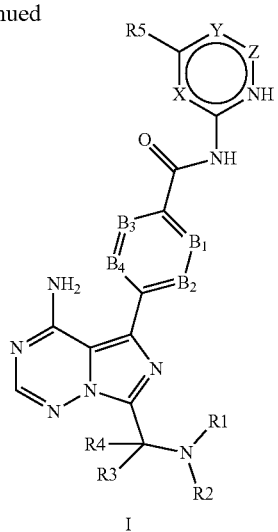

Starting material 3-amino-6-(aminomethyl)-1,2,4-triazin-5(4H)-one X can be prepared via a condensation reaction of ethyl bromopyruvate, dibenzylamine, and aminoguanidine carbonate, followed by debenzylation via hydrogenation over Pd—C catalyst [Mitchel, W. L. et al, *J. Heterocycl. Chem.* 21 (1984) pp 697]. This can then be reacted with an appropriately amine protected amino acid. The reaction of Cbz-N($R_2$)C$R_3R_4$)COOH can be carried out in a solvent such as DMF, THF or DCM in the presence of a base such as DIPEA, N-methylmorpholine, 4-DMAP or triethylamine and in the presence of a coupling reagent such as PyBOP, TBTU, EDCI or HATU to form N-((3-amino-5-oxo-4,5-dihydro-1,2,4-triazin-6-yl)methyl)amide XI. Cyclisation of the amino-triazinone XI can be performed using condensation reagents like phosphorous oxychloride under heating conditions to provide the 2-aminoimidazo[1,5-f][1,2,4]triazin-4(3H)-one derivatives XII. Subsequent iodination can be accomplished using iodine or N-iodosuccinimide in a suitable solvent like DCM or DMF at appropriate temperature to obtain compounds of formula XIII. Removal of the 2-amino group in the 2-aminoimidazo[1,5-f][1,2,4]triazin-4(3H)-one derivatives XIII can be performed using t-butyl nitrite in solvents like DMF/THF at room temperature to form imidazo[1,5-f][1,2,4]triazin-4(3H)-one derivatives XIV. 4-Amino-imidazo[1,5-f][1,2,4]triazine derivatives (XV) can be prepared from compounds XIV using phosphorousoxychloride, 1,2,4-triazole in pyridine and subsequent ammonolysis with ammonia(gas) in isopropanol at room temperature. Compounds of formula XVI can be prepared from compounds of formula XV using an appropriate boronic acid or pinacol ester (VIII), in the presence of a suitable palladium catalyst system and solvent, for example bis(diphenylphosphino)ferrocene palladium(II) chloride complex or tetrakis(triphenylphosphine)palladium (0) in the presence of potassium carbonate in dioxane/water provide compounds of formula XVI. Finally, cleaving the protective group of compounds with the formula XVI give the unprotected amine which after functionalisation, using methods well known in the art, with appropriate warheads with previously defined meanings, provided compounds of Formula (I). An example of such protective strategy is the use of the benzyloxycarbonyl protecting group to protect the amine from the amino acids used, and after deprotection with 33% HBr/HOAc or conc. HCl gave the resulting amines.

The amino acids HN($R_2$)C$R_3R_4$)COOH are either commercially available or they can be readily prepared using methods well known to the skilled organic chemist, to introduce protecting groups like benzyloxycarbonyl or tert-butyloxycarbonyl.

Palladium catalysts and conditions to form either the pinacol esters or to couple the boronic acids or pinacol esters with the 5-iodoimidazo[1,5-f][1,2,4]triazin-4-amine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002.

The present invention also includes within its scope all stereoisomeric forms of the 8-amino-imidazo[1,5-a]pyrazine and 4-amino-imidazo[1,5-f][1,2,4]triazine derivatives according to the present invention resulting, for example, because of configurational or geometrical isomerism. Such stereoisomeric forms are enantiomers, diastereoisomers, cis and trans isomers etc. For example where azepane-2-carboxylic acid is used as amino acid, there exists a mixture of two enantiomers. In the case of the individual stereoisomers of compounds of Formula (I) or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The 8-amino-imidazo[1,5-a]pyrazine and 4-amino-imidazo[1,5-f][1,2,4]triazine derivatives of the present invention, which can be in the form of a free base, may be isolated from the reaction mixture in the form of a pharmaceutically acceptable salt. The pharmaceutically acceptable salts may also be obtained by treating the free base of Formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The 8-amino-imidazo[1,5-a]pyrazine and 4-amino-imidazo[1,5-f][1,2,4]triazine derivatives of the present invention also exist as amorphous forms. Multiple crystalline forms are also possible. All the physical forms are included within the scope of the present invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{17}O$, $^{18}O$, $^{31}P$, $^{32}P$, $^{35}S$, $^{18}F$, and $^{36}Cl$, respectively.

Certain isotopically-labeled compounds of Formula (I) (e.g. those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically-labeled compounds of Formula (I) can generally be prepared by following procedures analogous to those disclosed in the Schemes and/or in the Examples hereinbelow, by substituting an appropriate isotopically labeled reagent for a non-isotopically labeled reagent.

The invention is illustrated by the following examples.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da and scanned with a step rate of 0.2 Da. and the capillary voltage was set to 5000 V. N2-gas was used for nebulisation.

LC-MS spectrometer (Waters) Detector: PDA (200-320 nm), Mass detector: ZQ

Eluent: A: acetonitrile with 0.05% trifluoroacetic acid, B: acetonitrile/water=1/9 (v/v) with 0.05% trifluoroacetic acid Method LCMS (A)

Column 1: Chromolith Performance, RP-18e, 4.6×100 mm,

Gradient method: Flow: 4 mL/min

| Time (min) | A (%) | B (%) |
|---|---|---|
| 0.00 | 100 | 0 |
| 3.60 | 0 | 100 |
| 4.00 | 0 | 100 |
| 4.05 | 100 | 0 |
| 6.00 | 100 | 0 |

Method LCMS (B)

Column 2: XBridge C18, 3.5 μm, 4.6×20 mm

Gradient method: Flow: 4 ml/min

| Time (min.) | A (%) | B (%) |
|---|---|---|
| 0.0 | 100 | 0 |
| 1.60 | 0 | 100 |
| 3.10 | 0 | 100 |
| 3.20 | 100 | 0 |
| 5.00 | 100 | 0 |

UPLC: Water acquity UPLC system; Column: BEH C18 1.7 μm, 2.1×100 mm, Detector: PDA (200-320 nm), Mass detector: SQD Eluent: A: acetonitrile with 0.035% trifluoroacetic acid, B: acetonitrile/water=1/9 (v/v) with 0.035% trifluoroacetic acid

| | Method | | | | | |
|---|---|---|---|---|---|---|
| | UPLC (A) Method 60 100 Flow: 0.75 mL/min | | UPLC (B) Method 40 80 Flow: 0.65 mL/min | | UPLC (C) Method 0 60 Flow: 0.60 mL/min | |
| Time (min) | A (%) | B (%) | A (%) | B (%) | A (%) | B (%) |
| 0.0 | 40 | 60 | 60 | 40 | 100 | 0 |
| 3.00 | 0 | 100 | 20 | 80 | 40 | 60 |
| 3.20 | 0 | 100 | 0 | 100 | 0 | 100 |
| 3.69 | 0 | 100 | 0 | 100 | 0 | 100 |
| 3.70 | 40 | 60 | 60 | 40 | 100 | 0 |

Preparative HPLC was conducted on a column (50×10 mm ID, 5 μm, Xterra Prep MS C18) at a flow rate of 5 ml/min, injection volume 500 μl, at room temperature and UV Detection at 210 nm.

The following abbreviations are used throughout the application with respect to chemical terminology:

HATU O-(7-Azabenzotriazol-1-yl)-1,1,3,3-tetramethyl-uroniumhexafluoro phosphate
Cbz Benzyloxycarbonyl
DMF N,N-Dimethylformamide
DCM Dichloromethane
EtOAc Ethyl acetate
DIPEA N,N-Diisopropylethylamine
THF Tetrahydrofuran
EtOH Ethanol
EDCI.HCl 1-(3-Dimethylaminopropyl)-3-ethylcarbodi-imide.hydrochloride
4-DMAP 4-Dimethylamino pyridine
PyBOP O-Benzotriazole-1-yl-oxy-trispyrrolidinophos-phonium hexafluorophosphate
TBTU O-Benzotriazol-1-yl-N,N,N',N'-tetramethyluro-nium tetrafluoroborate
HBr Hydrogen bromide
HCl Hydrogen chloride
HOAc Acetic acid
Z Benzyloxycarbonyl
Pro Proline
POCl$_3$ Phosphorous oxychloride
HPLC High Pressure Liquid Chromatography
UPLC Ultra Performance Liquid Chromatography
LiHMDS Lithium hexamethyldisilazide
MeOH Methanol
Gly Glycine
Ala Alanine
n-BuLi n-Butyllithium
CO$_2$ Carbon dioxide The names of the final products in the examples are generated using Chemdraw Ultra (version 9.0.7).

Intermediate 1

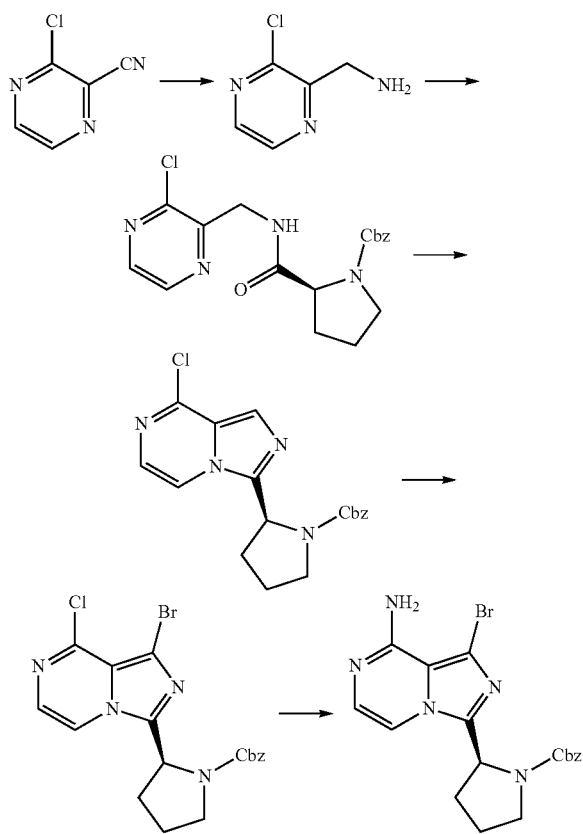

(S)-Benzyl 2-(8-amino-1-bromoimidazo[1,5-a]
pyrazin-3-yl)pyrrolidine-1-carboxylate (a)
(3-Chloropyrazin-2-yl)methanamine.hydrochloride To a solution of 3-chloropyrazine-2-carbonitrile (160 g, 1.147 mol) in acetic acid (1.5 L) was added Raney Nickel (50% slurry in water, 70 g, 409 mmol). The resulting mixture was stirred under 4 bar hydrogen at room temperature overnight. Raney Nickel was removed by filtration over decalite and the filtrate was concentrated under reduced pressure and co-evaporated with toluene. The remaining brown solid was dissolved in ethyl acetate at 50° C. and cooled on an ice-bath. 2M hydrogen chloride solution in diethyl ether (1.14 L) was added in 30 min. The mixture was allowed to stir at room temperature over weekend. The crystals were collected by filtration, washed with diethyl ether and dried under reduced pressure at 40° C. The product brown solid obtained was dissolved in methanol at 60° C. The mixture was filtered and partially concentrated, cooled to room temperature and diethyl ether (1000 ml) was added. The mixture was allowed to stir at room temperature overnight. The solids formed were collected by filtration, washed with diethyl ether and dried under reduced pressure at 40° C. to give 153.5 g of (3-chloropyrazin-2-yl)methanamine.hydrochloride as a brown solid (74.4%, content 77%).

(b) (S)-benzyl 2-((3-chloropyrazin-2-yl)methylcarbamoyl)pyrrolidine-1-carboxylate To a solution of (3-chloropyrazin-2-yl)methanamine.HCl (9.57 g, 21.26 mmol, 40% wt) and Z-Pro-OH (5.3 g, 21.26 mmol) in dichloromethane (250 mL) was added triethylamine (11.85 mL, 85 mmol) and the reaction mixture was cooled to 0° C. After 15 min stirring at 0° C., HATU (8.49 g, 22.33 mmol) was added. The mixture was stirred for 1 hour at 0° C. and then overnight at room temperature. The mixture was washed with 0.1 M HCl-solution, 5% NaHCO₃, water and brine, dried over sodium sulfate and concentrated in vacuo. The product was purified using silica gel chromatography (heptane/ethyl acetate=1/4 v/v %) to give 5 g of (S)-benzyl 2-((3-chloropyrazin-2-yl)methylcarbamoyl)pyrrolidine-1-carboxylate (62.7%).

(c) (S)-Benzyl 2-(8-chloroimidazo[1,5-a]pyrazin-3-yl)pyrrolidine-1-carboxylate (S)-Benzyl 2-((3-chloropyrazin-2-yl)methylcarbamoyl)pyrrolidine-1-carboxylate (20.94 mmol, 7.85 g) was dissolved in acetonitrile (75 ml), 1,3-dimethyl-2-imidazolidinone (62.8 mmol, 6.9 ml, 7.17 g) was added and the reaction mixture was cooled to 0° C. before POCl₃ (84 mmol, 7.81 ml, 12.84 g) was added drop wise while the temperature remained around 5° C. The reaction mixture was refluxed at 60-65° C. overnight. The reaction mixture was poured carefully in ammonium hydroxide 25% in water (250 ml)/crushed ice (500 ml) to give a yellow suspension (pH~8-9) which was stirred for 15 min until no ice was present in the suspension. Ethyl acetate was added, layers were separated and the aqueous layer was extracted with ethyl acetate (3×). The organic layers were combined and washed with brine, dried over sodium sulfate, filtered and evaporated to give 7.5 g crude product. The crude product was purified using silica gel chromatography (heptane/ethyl acetate=1/4 v/v %) to give 6.6 g of (S)-benzyl 2-(8-chloroimidazo[1,5-a]pyrazin-3-yl)pyrrolidine-1-carboxylate (88%).

(d) (S)-Benzyl 2-(1-bromo-8-chloroimidazo[1,5-a]pyrazin-3-yl)pyrrolidine-1-carboxylate N-Bromosuccinimide (24.69 mmol, 4.4 g) was added to a stirred solution of (S)-benzyl 2-(8-chloroimidazo[1,5-a]pyrazin-3-yl)pyrrolidine-1-carboxylate (24.94 mmol, 8.9 g) in DMF (145 mL). The reaction was stirred 3 h at rt. The mixture was poured (slowly) in a stirred mixture of water (145 mL), ethyl acetate (145 mL) and brine (145 mL). The mixture was then transferred into a separating funnel and extracted. The water layer was extracted with 2×145 mL ethyl acetate. The combined organic layers were washed with 3×300 mL water, 300 mL brine, dried over sodium sulfate, filtered and evaporated. The product was purified using silica gel chromatography (ethyl acetate/heptane=3/1 v/v %) to give 8.95 g of (S)-benzyl 2-(1-bromo-8-chloroimidazo[1,5-a]pyrazin-3-yl)pyrrolidine-1-carboxylate (82.3%).

(e) (S)-Benzyl 2-(8-amino-1-bromoimidazo[1,5-a]pyrazin-3-yl)pyrrolidine-1-carboxylate (S)-Benzyl 2-(1-bromo-8-chloroimidazo[1,5-a]pyrazin-3-yl)pyrrolidine-1-carboxylate (20.54 mmol, 8.95 g) was suspended in 2-propanol (113 ml) in a pressure vessel. 2-propanol (50 ml) was cooled to −78° C. in a pre-weighed flask (with stopper and stirring bar) and ammonia gas (646 mmol, 11 g) was led through for 15 minutes. The resulting solution was added to the suspension in the pressure vessel. The vessel was closed and stirred at room temperature and a slight increase in pressure was observed. Then the suspension was heated to 110° C. which resulted in an increased pressure to 4.5 bar. The clear solution was stirred at 110° C., 4.5 bar overnight. After 18 h the pressure remained 4 bar. The reaction mixture was concentrated in vacuum, the residue was suspended in ethyl acetate and subsequently washed with water. The layers were separated and the aqueous layer was extracted with ethyl acetate. The combined organic layers were washed with water, saturated sodium chloride solution, dried over sodium sulfate and concentrated to give 7.35 g of (S)-benzyl 2-(8-amino-1-bromoimidazo[1,5-a]pyrazin-3-yl)pyrrolidine-1-carboxylate (86%).

Intermediate 2

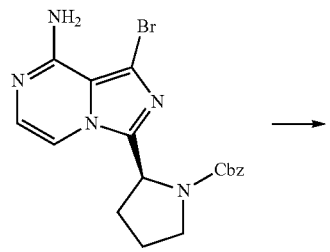

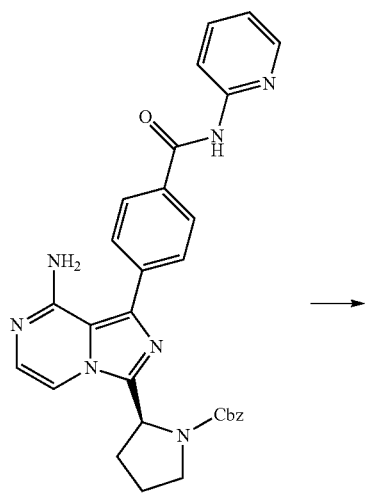

(S)-4-(8-Amino-3-(pyrrolidin-2-yl)imidazo[1,5-a]pyrazin-1-yl)-N-(pyridin-2-yl)benzamide (a) (S)-Benzyl 2-(8-amino-1-(4-(pyridin-2-ylcarbamoyl)phenyl)imidazo[1,5-a]pyrazin-3-yl)pyrrolidine-1-carboxylate (S)-benzyl 2-(8-amino-1-bromoimidazo[1,5-a]pyrazin-3-yl)pyrrolidine-1-carboxylate (0.237 mmol, 98.5 mg) and 4-(pyridin-2-yl-aminocarbonyl)benzeneboronic acid (0.260 mmol, 63.0 mg) were suspended in a mixture of 2N aqueous potassium carbonate solution (2.37 mmol, 1.18 mL) and dioxane (2.96 mL). Nitrogen was bubbled through the mixture, followed by the addition of 1,1'-bis(diphenylphosphino)ferrocene palladium (ii) chloride (0.059 mmol, 47.8 mg). The reaction mixture was heated for 20 minutes at 140° C. in the microwave. Water was added to the reaction mixture, followed by an extraction with ethyl acetate (2×). The combined organic layer was washed with brine, dried over magnesium sulfate and evaporated. The product was purified using silica gel and dichloromethane/methanol=9/1 v/v % as eluent to afford 97.1 mg of (S)-benzyl 2-(8-amino-1-(4-(pyridin-2-ylcarbamoyl)phenyl)imidazo[1,5-a]pyrazin-3-yl)pyrrolidine-1-carboxylate (77%).

(b) (S)-4-(8-Amino-3-(pyrrolidin-2-yl)imidazo[1,5-a]pyrazin-1-yl)-N-(pyridin-2-yl)benzamide To (S)-benzyl 2-(8-amino-1-(4-(pyridin-2-ylcarbamoyl)phenyl)imidazo[1,5-a]pyrazin-3-yl)pyrrolidine-1-carboxylate (0.146 mmol, 78 mg) was added a 33% hydrobromic acid/acetic acid solution (11.26 mmol, 2 ml) and the mixture was left at room temperature for 1 hour. The mixture was diluted with water and extracted with dichloromethane. The aqueous phase was neutralized using 2N sodium hydroxide solution, and then extracted with dichloromethane. The organic layer was dried over magnesium sulfate, filtered and evaporated to give 34 mg of (S)-4-(8-Amino-3-(pyrrolidin-2-yl)imidazo[1,5-a]pyrazin-1-yl)-N-(pyridin-2-yl)benzamide (58%).

Example 1

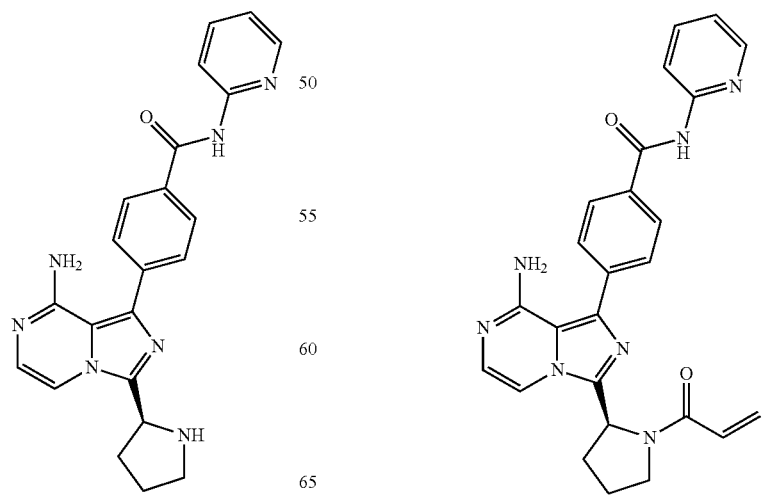

(S)-4-(3-(1-Acryloylpyrrolidin-2-yl)-8-aminoimidazo[1,5-a]pyrazin-1-yl)-N-(pyridin-2-yl)benzamide To a solution of (S)-4-(8-amino-3-(pyrrolidin-2-yl)imidazo[1,5-a]pyrazin-1-yl)-N-(pyridin-2-yl)benzamide (0.626 mmol, 250 mg) in dichloromethane (25 ml) at 0° C. was added triethylamine (0.626 mmol, 0.087 ml, 63.3 mg) and, drop wise, acryloyl chloride (0.657 mmol, 0.053 ml, 59.5 mg). The resulting mixture was stirred at 0° C. for 2 hours. The mixture was washed with water, dried over magnesium sulfate. After evaporation, the residue was purified by preparative HPLC. Fractions containing product were collected and lyophilized to afford 126 mg of (S)-4-(3-(1-acryloylpyrrolidin-2-yl)-8-aminoimidazo[1,5-a]pyrazin-1-yl)-N-(pyridin-2-yl)benzamide (44.4% yield). Data: UPLC (C) $R_t$: 1.50 min; m/z 454.3 (M+H)$^+$.

Example 2

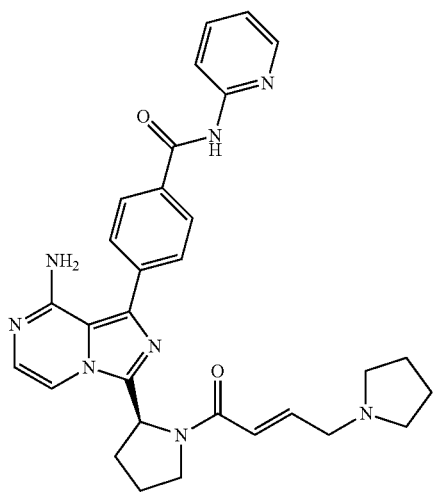 [SMILES: Nc1nccn2c([C@@H]3CCCN3C(=O)/C=C/CN3CCCC3)nc(-c3ccc(C(=O)Nc4ccccn4)cc3)c12]

(S,E)-4-(8-amino-3-(1-(4-(pyrrolidin-1-yl)but-2-enoyl)pyrrolidin-2-yl)imidazo[1,5-a]pyrazin-1-yl)-N-(pyridin-2-yl)benzamide To a solution of (S)-4-(8-Amino-3-(pyrrolidin-2-yl)imidazo[1,5-a]pyrazin-1-yl)-N-(pyridin-2-yl)benzamide (intermediate 2b, 19.7 mg, 0.049 mmol), triethylamine (20 mg, 0.197 mmol, 0.027 mL) and (E)-4-(pyrrolidin-1-yl)but-2-enoic acid hydrochloride (9.45 mg, 0.049 mmol) in dichloromethane (2 mL) was added HATU (18.75 mg, 0.049 mmol). The mixture was stirred for 30 min at room temperature. The mixture was washed with water dried over magnesium sulfate and concentrated in vacuo. The residue was purified by preparative HPLC. Fractions containing product were collected and reduced to dryness to afford 7.1 mg of (S,E)-4-(8-amino-3-(1-(4-(pyrrolidin-1-yl)but-2-enoyl)pyrrolidin-2-yl)imidazo[1,5-a]pyrazin-1-yl)-N-(pyridin-2-yl)benzamide (26.8% yield). Data: UPLC (C) $R_t$: 1.25 min; m/z 537.4 (M+H)$^+$.

Example 3

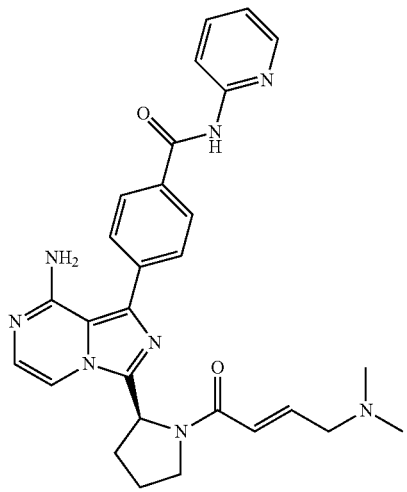 [SMILES: CN(C)C/C=C/C(=O)N1CCC[C@H]1c1nc(-c2ccc(C(=O)Nc3ccccn3)cc2)c2c(N)nccn12]

(S,E)-4-(8-Amino-3-(1-(4-(dimethylamino)but-2-enoyl)pyrrolidin-2-yl)imidazo[1,5-a]pyrazin-1-yl)-N-(pyridin-2-yl)benzamide This compound was prepared, in an analogous manner as described in Example 2, from the compound described in intermediate 2b and (E)-4-(dimethylamino)but-2-enoic acid, to afford the title compound (11.8 mg, 46.6%). Data: UPLC (C) $R_t$: 1.29 min; m/z 511.0 (M+H)$^+$.

Intermediate 3

(E)-4-Methoxybut-2-enoic acid

Sodium methoxide (30%/Methanol, 30.3 mmol, 5.68 mL) was added via a glass syringe to a stirred solution of 4-bromocrotonic acid (6.06 mmol, 1 g) in methanol (60 mL) at room temperature. The light yellow solution was stirred for 30 min at room temperature and 2 h. at reflux. After cooling the reaction mixture, the solvent was removed under reduced pressure. The residue was partitioned between water (50 mL) and diethyl ether (50 mL). 2M aq. hydrochloride solution (3.5 mL) was added until pH was ~pH 1. The water layer was separated and extracted with diethyl ether (3×20 mL). The combined organic layers were washed with brine, dried over sodium sulfate, filtered and concentrated in vacuo, to give 650 mg of (E)-4-Methoxybut-2-enoic acid (92%).

Example 4

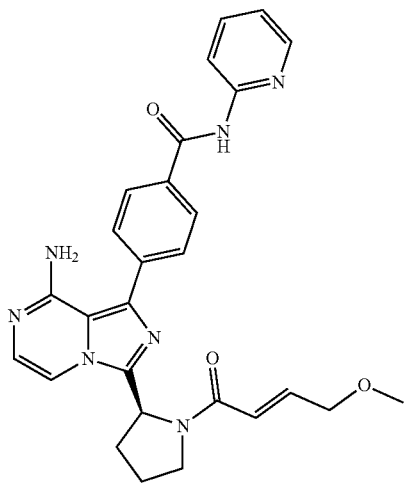 [SMILES: COC/C=C/C(=O)N1CCC[C@H]1c1nc(-c2ccc(C(=O)Nc3ccccn3)cc2)c2c(N)nccn12]

(S,E)-4-(8-amino-3-(1-(4-methoxybut-2-enoyl)pyrrolidin-2-yl)imidazo[1,5-a]pyrazin-1-yl)-N-(pyridin-2-yl)benzamide This compound was prepared, in an analogous manner as described in Example 2, from the compound described in intermediate 2b and (E)-4-methoxybut-2-enoic acid (Intermediate 3), to afford the title compound (11 mg, 29.9%). Data: UPLC (C) $R_t$: 1.58 min; m/z 498.3 (M+H)$^+$.

Example 5

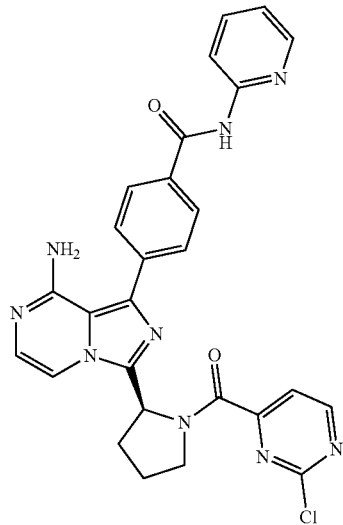 [SMILES: Nc1nccn2c([C@@H]3CCCN3C(=O)c3ccnc(Cl)n3)nc(-c3ccc(C(=O)Nc4ccccn4)cc3)c12]

(S)-4-(8-amino-3-(1-(2-chloropyrimidine-4-carbonyl)pyrrolidin-2-yl)imidazo[1,5-a]pyrazin-1-yl)-N-(pyridin-2-yl)benzamide This compound was prepared, in an analogous manner as described in Example 2, from the compound described in intermediate 2b and 2-chloropyrimidine-4-carboxylic acid, to afford the title compound (8.3 mg, 40.4%). Data: UPLC (C) $R_t$: 1.64 min; m/z 540.1 (M+H)$^+$.

Example 6

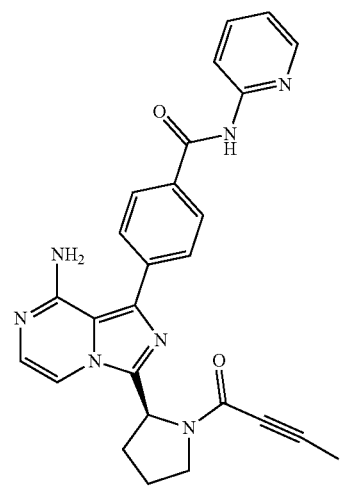 [SMILES: CC#CC(=O)N1CCC[C@H]1c1nc(-c2ccc(C(=O)Nc3ccccn3)cc2)c2c(N)nccn12]

(S)-4-(8-amino-3-(1-but-2-ynoylpyrrolidin-2-yl)imidazo[1,5-a]pyrazin-1-yl)-N-(pyridin-2-yl)benzamide This compound was prepared, in an analogous manner as described in Example 2, from the compound described in intermediate 2b and 2-butynoic acid, to afford the title compound (10.5 mg, 18.0%). Data: LCMS (B) $R_t$: 2.08 min; m/z 466.1 (M+H)$^+$.

Intermediate 4

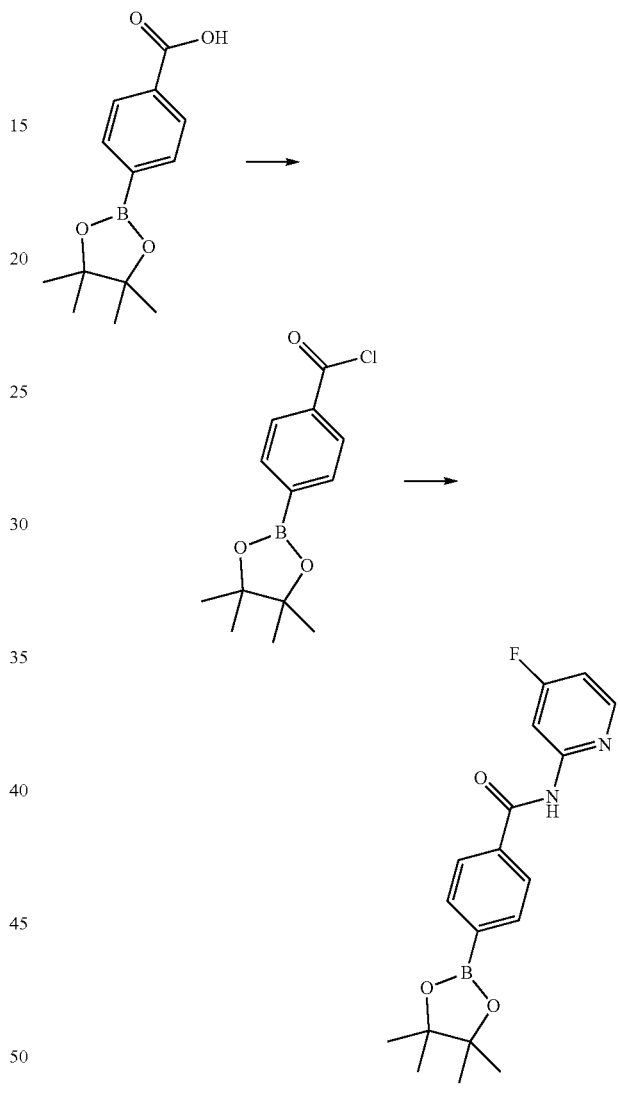

N-(4-fluoropyridin-2-yl)-4-(4,4,5,5-tetramethyl-1,3,2-dioxaborolan-2-yl)benzamide (a) 4-(4,4,5,5-Tetramethyl-1,3,2-dioxaborolan-2-yl)benzoyl chloride To a cold (0° C.) solution of 4-(4,4,5,5-tetramethyl-1,3,2-dioxaborolan-2-yl)benzoic acid (40.3 mmol, 10.01 g) in dichloromethane (206 mL) was added a catalytic amount of DMF. A solution of oxalyl chloride (101 mmol, 8.66 mL, 12.8 g) was added drop wise. After stirring for 30 min at 0° C., the reaction mixture was allowed to warm up to room temperature and the mixture was stirred for an additional 3 hours. The reaction mixture was concentrated to give 10.9 g. of crude 4-(4,4,5,5-tetramethyl-1,3,2-dioxaborolan-2-yl)benzoyl chloride (101%).

(b) N-(4-fluoropyridin-2-yl)-4-(4,4,5,5-tetramethyl-1,3,2-dioxaborolan-2-yl)benzamide To a solution of 4-(4,4,5,5-tetramethyl-1,3,2-dioxaborolan-2-yl)benzoyl chloride (1.688 mmol, 450 mg) in acetonitrile (24.8 mL) was added 2-amino-4-fluoropyridine (4.22 mmol, 473 mg). The reaction mixture was stirred at room temperature for 1.5 h. The reaction mixture was concentrated to a small volume, 3% aq. citric acid solution (18 mL) was added and the mixture was extracted with dichloromethane (2×15 mL). The combined organic layer was washed with 3% aq. citric acid solution, dried over magnesium sulfate, filtered and evaporated to afford 542.2 mg of N-(4-fluoropyridin-2-yl)-4-(4,4,5,5-tetramethyl-1,3,2-dioxaborolan-2-yl)benzamide (94%) as an off-white solid.

Intermediate 5

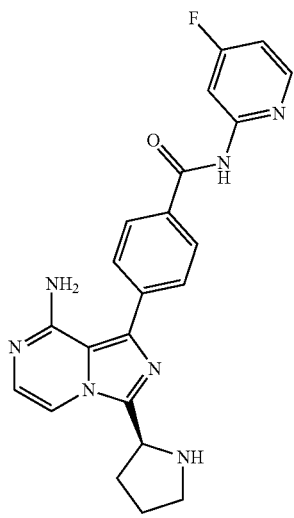 [SMILES: Nc1nccn2c([C@@H]3CCCN3)nc(-c3ccc(C(=O)Nc4cc(F)ccn4)cc3)c12]

(S)-4-(8-Amino-3-(pyrrolidin-2-yl)imidazo[1,5-a]pyrazin-1-yl)-N-(4-fluoropyridin-2-yl)benzamide This intermediate was prepared, in an analogous manner as described for intermediate 2b, from (S)-benzyl 2-(8-amino-1-bromoimidazo[1,5-a]pyrazin-3-yl)pyrrolidine-1-carboxylate (Intermediate 1e) and N-(4-fluoropyridin-2-yl)-4-(4,4,5,5-tetramethyl-1,3,2-dioxaborolan-2-yl)benzamide (intermediate 4b) to afford the title compound (331 mg, 93%).

Example 7

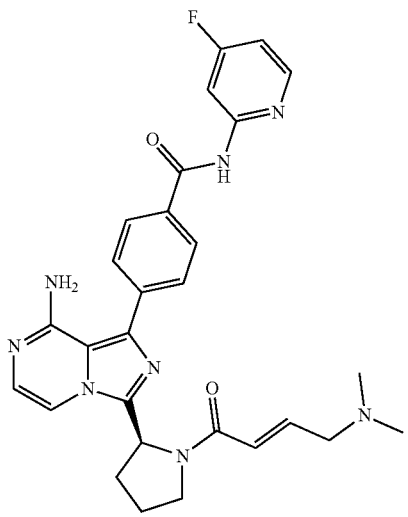 [SMILES: CN(C)C/C=C/C(=O)N1CCC[C@H]1c1nc(-c2ccc(C(=O)Nc3cc(F)ccn3)cc2)c2c(N)nccn12]

(S,E)-4-(8-Amino-3-(1-(4-(dimethylamino)but-2-enoyl)pyrrolidin-2-yl)imidazo[1,5-a]pyrazin-1-yl)-N-(4-fluoropyridin-2-yl)benzamide This compound was prepared, in an analogous manner as described in Example 2, from the compound described in intermediate 5 and (E)-4-(dimethylamino)but-2-enoic acid, to afford the title compound (33.4 mg, 54.1%). Data: UPLC (C) $R_t$: 1.72 min; m/z 529.3 (M+H)⁺.

Intermediate 6

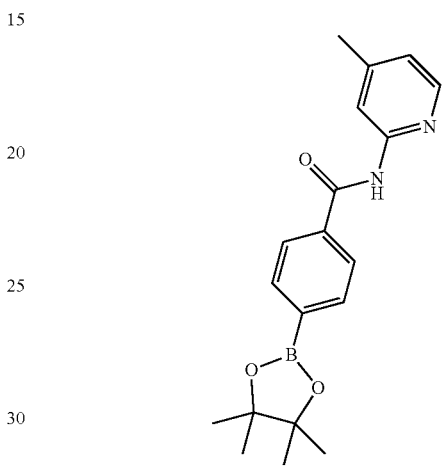

N-(4-Methylpyridin-2-yl)-4-(4,4,5,5-tetramethyl-1,3,2-dioxaborolan-2-yl)benzamide To a stirred solution of 4-methylpyridin-2-amine (7.86 mmol, 850 mg) in THF (50 mL) was added dropwise a solution of 1M LiHMDS in THF (8.0 mmol, 8 mL) at room temperature. After the reaction mixture turned dark green, a solution of 4-(4,4,5,5-tetramethyl-1,3,2-dioxaborolan-2-yl) benzoyl chloride (9.6 mmol, 2.56 g) in dichloromethane (55 mL) was added dropwise. The mixture was stirred at room temperature for 2.5 h and was then concentrated. 3% aq. Citric acid solution (18 mL) was added and the mixture was extracted with dichloromethane (2×15 mL). The combined organic layer was washed with 3% aq. citric acid solution, dried over magnesium sulfate, filtered and evaporated. The residue was dissolved in THF (15 mL) and 6M NaOH solution (15 mL) was added. The mixture was stirred for 4 h. at room temperature. Ethyl acetate was added and the layers were separated. The organic layer was washed with water and brine, dried over sodium sulfate, filtered and evaporated. The residue was purified by chromatography on silica (eluent: DCM/MeOH=98/2 to DCM/MeOH=95/5) to yield 1.1 g of N-(4-methylpyridin-2-yl)-4-(4,4,5,5-tetramethyl-1,3,2-dioxaborolan-2-yl)benzamide (40.7%).

Intermediate 7

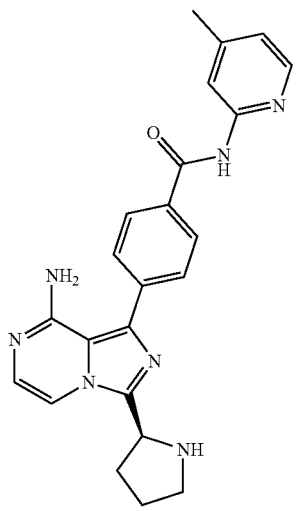 [SMILES: Cc1ccnc(NC(=O)c2ccc(-c3nc([C@@H]4CCCN4)n4ccnc(N)c34)cc2)c1]

(S)-4-(8-Amino-3-(pyrrolidin-2-yl)imidazo[1,5-a]
pyrazin-1-yl)-N-(4-methylpyridin-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and N-(4-methylpyridin-2-yl)-4-(4,4,5,5-tetramethyl-1,3,2-dioxaborolan-2-yl)benzamide (intermediate 6) to afford the title compound (125.5 mg, 82%).

Example 8

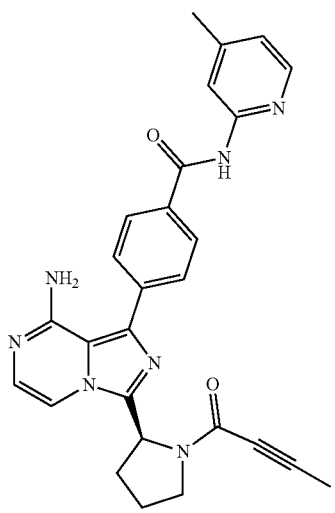 [SMILES: CC#CC(=O)N1CCC[C@H]1c1nc(-c2ccc(C(=O)Nc3cc(C)ccn3)cc2)c2c(N)nccn12]

(S)-4-(8-Amino-3-(1-but-2-ynoylpyrrolidin-2-yl)
imidazo[1,5-a]pyrazin-1-yl)-N-(4-methylpyridin-2-
yl)benzamide This compound was prepared, in an analogous manner as described in Example 2, from (S)-4-(8-amino-3-(pyrrolidin-2-yl)imidazo[1,5-a]pyrazin-1-yl)-N-(4-methylpyridin-2-yl)benzamide (intermediate 7) and 2-butynoic acid, to afford the title compound (6.3 mg, 27.2%). Data: UPLC (C) $R_t$: 1.56 min; m/z 480.3 (M+H)$^+$.

Intermediate 8

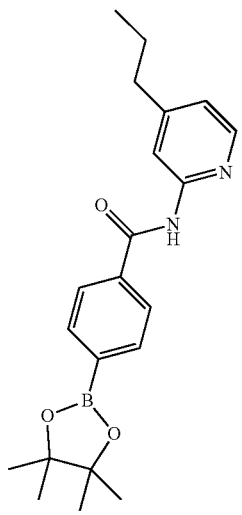 [SMILES: CCCc1ccnc(NC(=O)c2ccc(B3OC(C)(C)C(C)(C)O3)cc2)c1]

N-(4-Propylpyridin-2-yl)-4-(4,4,5,5-tetramethyl-1,3,
2-dioxaborolan-2-yl)benzamide This compound was prepared, in an analogous manner as described in Intermediate 6, starting from 4-propylpyridin-2-amine, to afford the title compound (371.5 mg, 54.1%).

Intermediate 9

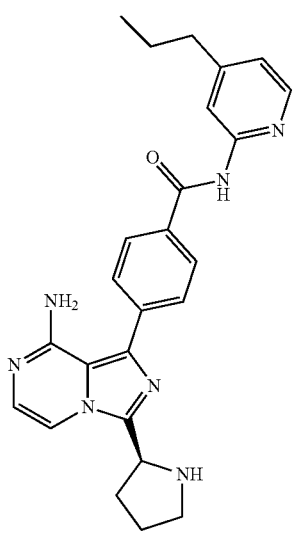 [SMILES: CCCc1ccnc(NC(=O)c2ccc(-c3nc([C@@H]4CCCN4)n4ccnc(N)c34)cc2)c1]

(S)-4-(8-Amino-3-(pyrrolidin-2-yl)imidazo[1,5-a]
pyrazin-1-yl)-N-(4-propylpyridin-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and N-(4-Propylpyridin-2-yl)-4-(4,4,5,5-tetramethyl-1,3,2-dioxaborolan-2-yl)benzamide (intermediate 8) to afford the title compound (147.8 mg, 93%).

Example 9

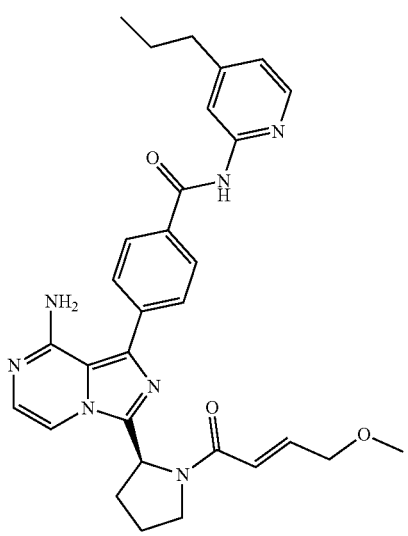 [SMILES: CCCc1ccnc(NC(=O)c2ccc(-c3nc([C@@H]4CCCN4C(=O)/C=C/COC)n4ccnc(N)c34)cc2)c1]

(S,E)-4-(8-Amino-3-(1-(4-methoxybut-2-enoyl)pyr-rolidin-2-yl)imidazo[1,5-a]pyrazin-1-yl)-N-(4-pro-pylpyridin-2-yl)benzamide This compound was prepared, in an analogous manner as described in Example 2, from (S)-4-(8-amino-3-(pyrrolidin-2-yl)imidazo[1,5-a]pyrazin-1-yl)-N-(4-propylpyridin-2-yl)benzamide (intermediate 9) and (E)-4-methoxybut-2-enoic acid (Intermediate 3), to afford the title compound (30.9 mg, 65.7%). Data: UPLC (C) $R_t$: 2.73 min; m/z 566.3 (M+H)$^+$.

Intermediate 10

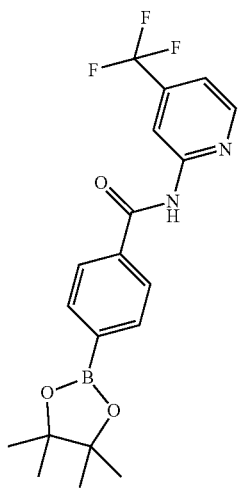 [SMILES: CC1(C)OB(c2ccc(C(=O)Nc3cc(C(F)(F)F)ccn3)cc2)OC1(C)C]

4-(4,4,5,5-Tetramethyl-1,3,2-dioxaborolan-2-yl)-N-(4-(trifluoromethyl)pyridin-2-yl)benzamide This compound was prepared, in an analogous manner as described in Intermediate 6, starting from 4-(trifluoromethyl)pyridin-2-amine, to afford the title compound (657.2 mg, 89%).

Intermediate 11

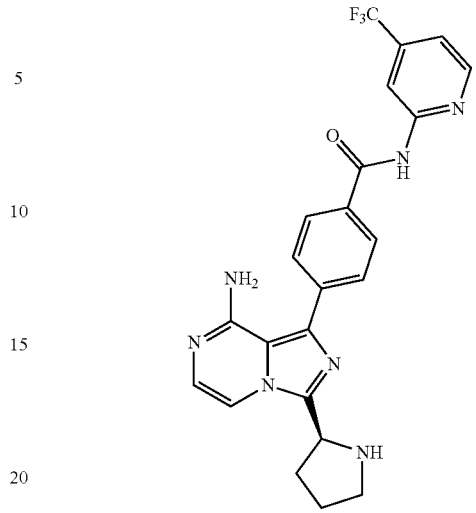

(S)-4-(8-Amino-3-(pyrrolidin-2-yl)imidazo[1,5-a]pyrazin-1-yl)-N-(4-(trifluoromethyl)pyridin-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and 4-(4,4,5,5-Tetramethyl-1,3,2-dioxaborolan-2-yl)-N-(4-(trifluoromethyl)pyridin-2-yl)benzamide (intermediate 10) to afford the title compound (163 mg, 87%).

Example 10

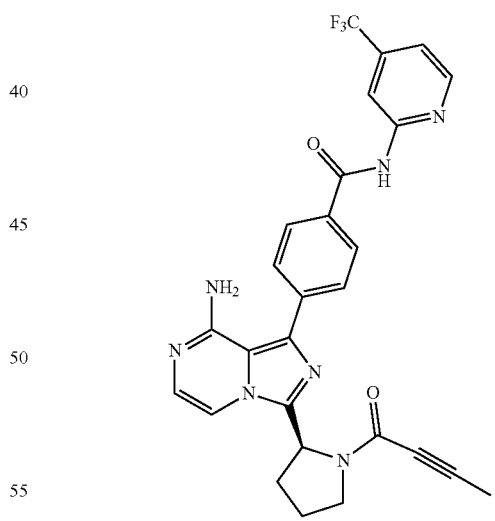

(S)-4-(8-Amino-3-(1-but-2-ynoylpyrrolidin-2-yl)imidazo[1,5-a]pyrazin-1-yl)-N-(4-(trifluoromethyl)pyridin-2-yl)benzamide This compound was prepared, in an analogous manner as described in Example 2, from (S)-4-(8-amino-3-(pyrrolidin-2-yl)imidazo[1,5-a]pyrazin-1-yl)-N-(4-(trifluoromethyl)pyridin-2-yl)benzamide (intermediate 11) and 2-butynoic acid, to afford the title compound (7.1 mg, 31.1%). Data: UPLC (C) $R_t$: 2.63 min; m/z 534.2 (M+H)$^+$.

Intermediate 12

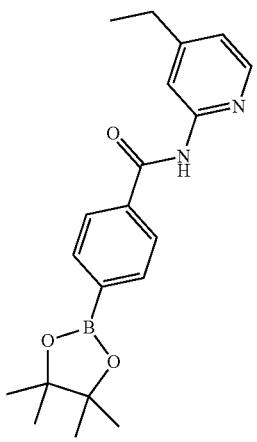 [SMILES: CCc1ccnc(NC(=O)c2ccc(B3OC(C)(C)C(C)(C)O3)cc2)c1]

N-(4-Ethylpyridin-2-yl)-4-(4,4,5,5-tetramethyl-1,3,2-dioxaborolan-2-yl)benzamide This compound was prepared, in an analogous manner as described in Intermediate 4, starting from 4-ethylpyridin-2-amine, to afford the title compound (334.5 mg, 50.6%).

Intermediate 13

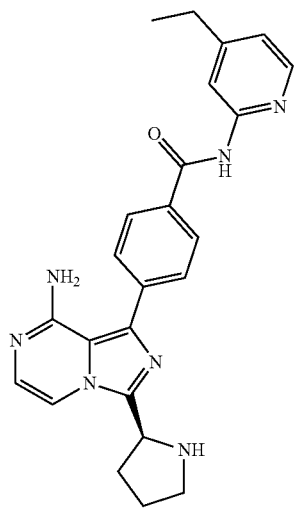 [SMILES: CCc1ccnc(NC(=O)c2ccc(-c3nc([C@@H]4CCCN4)n4ccnc(N)c34)cc2)c1]

(S)-4-(8-Amino-3-(pyrrolidin-2-yl)imidazo[1,5-a]pyrazin-1-yl)-N-(4-ethylpyridin-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and N-(4-ethylpyridin-2-yl)-4-(4,4,5,5-tetramethyl-1,3,2-dioxaborolan-2-yl)benzamide (intermediate 12) to afford the title compound (133.8 mg, 89%).

Example 11

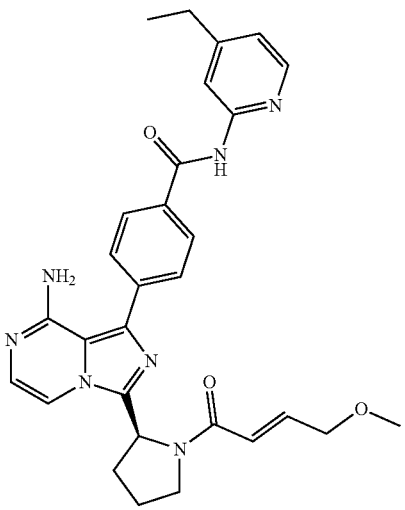 [SMILES: CCc1ccnc(NC(=O)c2ccc(-c3nc([C@@H]4CCCN4C(=O)/C=C/COC)n4ccnc(N)c34)cc2)c1]

(S,E)-4-(8-Amino-3-(1-(4-methoxybut-2-enoyl)pyrrolidin-2-yl)imidazo[1,5-a]pyrazin-1-yl)-N-(4-ethylpyridin-2-yl)benzamide This compound was prepared, in an analogous manner as described in Example 2, from (S)-4-(8-amino-3-(pyrrolidin-2-yl)imidazo[1,5-a]pyrazin-1-yl)-N-(4-ethylpyridin-2-yl)benzamide (intermediate 13) and (E)-4-methoxybut-2-enoic acid (Intermediate 3), to afford the title compound (10.6 mg, 28.8%). Data: UPLC (C) $R_t$: 1.60 min; m/z 526.3 (M+H)$^+$.

Intermediate 14

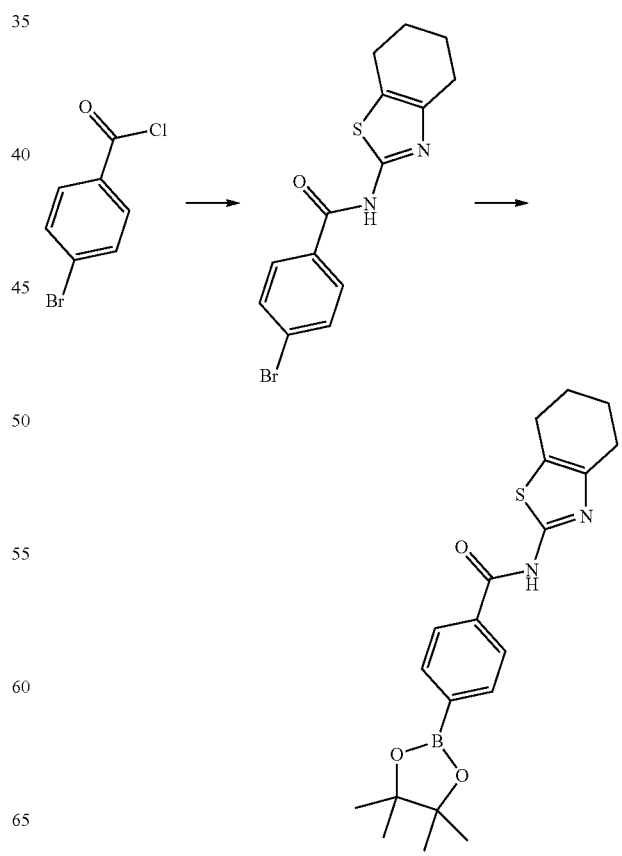

N-(4,5,6,7-Tetrahydrobenzo[d]thiazol-2-yl)-4-(4,4,5,5-tetramethyl-1,3,2-dioxaborolan-2-yl)benzamide (a) 4-Bromo-N-(4,5,6,7-tetrahydrobenzo[d]thiazol-2-yl)benzamide 4-Bromobenzoyl chloride (1.5 g, 6.83 mmol) and 4,5,6,7-Tetrahydro-1,3-benzothiazol-2-amine (1.054 g, 6.83 mmol) were dissolved in Pyridine (15 ml) and stirred at 50° C. for 1.5 h. The reaction mixture was cooled to room temperature and poured in water. The solid formed was filtered, washed with water. The solids were co-evaporated with toluene twice to afford 1.8 g of 4-bromo-N-(4,5,6,7-tetrahydrobenzo[d]thiazol-2-yl)benzamide (78%) as a yellow solid.

(b) N-(4,5,6,7-Tetrahydrobenzo[d]thiazol-2-yl)-4-(4,4,5,5-tetramethyl-1,3,2-dioxaboro-lan-2-yl)benzamide To a solution of 4-bromo-N-(4,5,6,7-tetrahydrobenzo[d]thiazol-2-yl)benzamide (1.8 g, 5.34 mmol) dioxane (40 ml) was added bis(pinacolato)diboron (1.762 g, 6.94 mmol) and potassium acetate (1.048 g, 10.68 mmol). The reaction mixture was degassed with nitrogen. Subsequently 1,1'-bis(diphenylphosphino)ferrocenepalladium(II) dichloride (0.218 g, 0.267 mmol) was added and the is reaction mixture was stirred at 80° C. for 5 days. The mixture was cooled to room temperature and after addition of water extracted three times with EtOAC. The organic layers were combined, washed with brine, dried over sodium sulfate, filtered and evaporated. The crude product was purified using silica gel chromatography (heptane/ethyl acetate 3/7 to 7/3 v/v %) to give 600 mg of N-(4,5,6,7-tetrahydrobenzo[d]thiazol-2-yl)-4-(4,4,5,5-tetramethyl-1,3,2-dioxaboro-lan-2-yl)benzamide (29.3%).
Intermediate 15

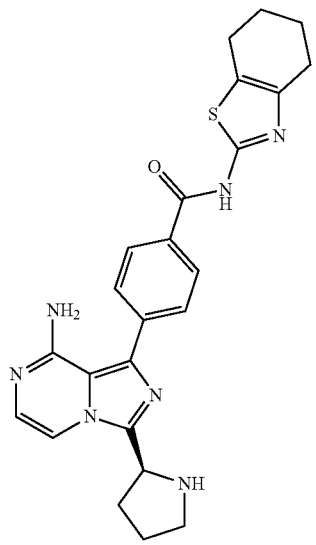 [SMILES: Nc1nccn2c([C@@H]3CCCN3)nc(-c3ccc(C(=O)Nc4nc5c(s4)CCCC5)cc3)c12]

(S)-4-(8-Amino-3-(pyrrolidin-2-yl)imidazo[1,5-a]pyrazin-1-yl)-N-(4,5,6,7-tetrahydrobenzo[d]thiazol-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and N-(4,5,6,7-tetrahydrobenzo[d]thiazol-2-yl)-4-(4,4,5,5-tetramethyl-1,3,2-dioxaborolan-2-yl)benzamide (intermediate 14b) to afford the title compound (260 mg, 60%).

Example 12

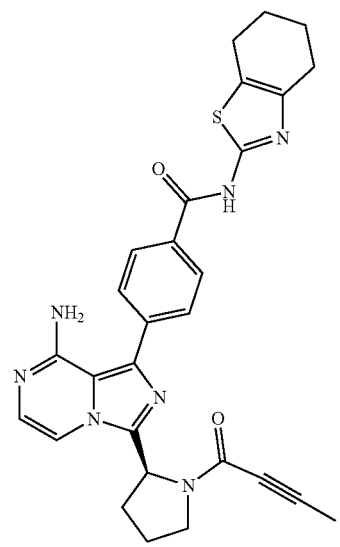 [SMILES: CC#CC(=O)N1CCC[C@H]1c1nc(-c2ccc(C(=O)Nc3nc4c(s3)CCCC4)cc2)c2c(N)nccn12]

(S)-4-(8-Amino-3-(1-but-2-ynoylpyrrolidin-2-yl)imidazo[1,5-a]pyrazin-1-yl)-N-(4,5,6,7-tetrahydrobenzo[d]thiazol-2-yl)benzamide This compound was prepared, in an analogous manner as described in Example 2, from (S)-4-(8-amino-3-(pyrrolidin-2-yl)imidazo[1,5-a]pyrazin-1-yl)-N-(4,5,6,7-tetrahydrobenzo[d]thiazol-2-yl)benzamide (intermediate 15) and 2-butynoic acid, to afford the title compound (7 mg, 19.2%).
Data: UPLC (C) $R_t$: 2.41 min; m/z 526.3 (M+H)$^+$.
Intermediate 16

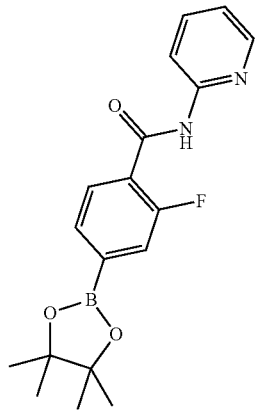 [SMILES: CC1(C)OB(c2ccc(C(=O)Nc3ccccn3)c(F)c2)OC1(C)C]

2-Fluoro-N-(pyridin-2-yl)-4-(4,4,5,5-tetramethyl-1,3,2-dioxaborolan-2-yl)benzamide This compound was prepared, in an analogous manner as described in Intermediate 14, starting from 4-bromo-2-fluorobenzoic acid, to afford the title compound (2.54 g, 76%).

Intermediate 17

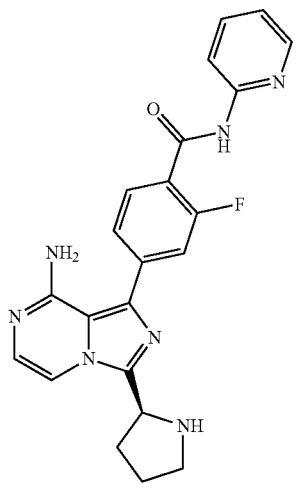 [SMILES: Nc1nccn2c([C@@H]3CCCN3)nc(-c3ccc(C(=O)Nc4ccccn4)c(F)c3)c12]

(S)-4-(8-Amino-3-(pyrrolidin-2-yl)imidazo[1,5-a]pyrazin-1-yl)-2-fluoro-N-(pyridin-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and 2-Fluoro-N-(pyridin-2-yl)-4-(4,4,5,5-tetramethyl-1,3,2-dioxaborolan-2-yl)benzamide (intermediate 16) to afford the title compound (160 mg, 76%).

Example 13

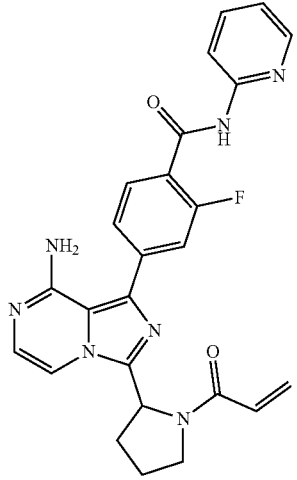 [SMILES: C=CC(=O)N1CCCC1c1nc(-c2ccc(C(=O)Nc3ccccn3)c(F)c2)c2c(N)nccn12]

(S)-4-(3-(1-acryloylpyrrolidin-2-yl)-8-aminoimidazo[1,5-a]pyrazin-1-yl)-2-fluoro-N-(pyridin-2-yl)benzamide This compound was prepared, in an analogous manner as described in Example 1, from (S)-4-(8-amino-3-(pyrrolidin-2-yl)imidazo[1,5-a]pyrazin-1-yl)-2-fluoro-N-(pyridin-2-yl)benzamide (intermediate 17) and acryloylchloride, to afford the title compound (13 mg, 38.4%). Data: UPLC (C) $R_t$: 1.67 min; m/z 472.3 (M+H)$^+$.

Intermediate 18

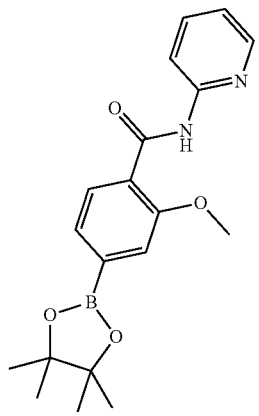 [SMILES: COc1cc(B2OC(C)(C)C(C)(C)O2)ccc1C(=O)Nc1ccccn1]

2-Methoxy-N-(pyridin-2-yl)-4-(4,4,5,5-tetramethyl-1,3,2-dioxaborolan-2-yl)benzamide This compound was prepared, in an analogous manner as described in Intermediate 14, starting from 4-bromo-2-methoxybenzoic acid, to afford the title compound (2.6 g, 90%).

Intermediate 19

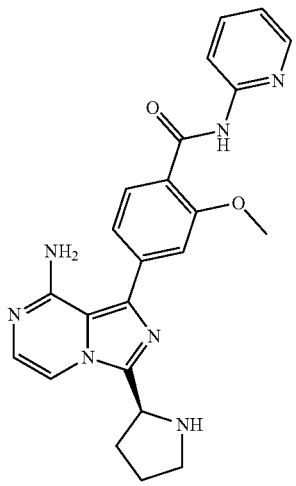 [SMILES: COc1cc(-c2nc([C@@H]3CCCN3)n3ccnc(N)c23)ccc1C(=O)Nc1ccccn1]

(S)-4-(8-Amino-3-(pyrrolidin-2-yl)imidazo[1,5-a]pyrazin-1-yl)-2-methoxy-N-(pyridin-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and 2-methoxy-N-(pyridin-2-yl)-4-(4,4,5,5-tetramethyl-1,3,2-dioxaborolan-2-yl)benzamide (intermediate 18) to afford the title compound (175 mg, 56.6%).

Example 14

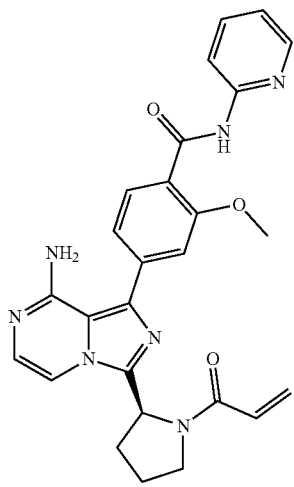 [SMILES: C=CC(=O)N1CCC[C@H]1c1nc(-c2ccc(C(=O)Nc3ccccn3)c(OC)c2)c2c(N)nccn12]

(S)-4-(3-(1-Acryloylpyrrolidin-2-yl)-8-aminoimidazo[1,5-a]pyrazin-1-yl)-2-methoxy-N-(pyridin-2-yl)benzamide This compound was prepared, in an analogous manner as described in Example 1, from (S)-4-(8-amino-3-(pyrrolidin-2-yl)imidazo[1,5-a]pyrazin-1-yl)-2-methoxy-N-(pyridin-2-yl)benzamide (intermediate 19) and acryloylchloride, to afford the title compound (14 mg, 35.5%). Data: UPLC (C) $R_t$: 1.74 min; m/z 484.3 (M+H)$^+$.

Intermediate 20

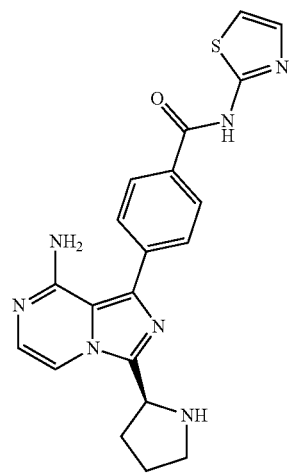 [SMILES: Nc1nccn2c([C@@H]3CCCN3)nc(-c3ccc(C(=O)Nc4nccs4)cc3)c12]

(S)-4-(8-Amino-3-(pyrrolidin-2-yl)imidazo[1,5-a]pyrazin-1-yl)-N-(thiazol-2-yl)benzamide This intermediate was prepared, in an analogous manner as described for intermediate 2, from (S)-benzyl 2-(8-amino-1-bromoimidazo[1,5-a]pyrazin-3-yl)pyrrolidine-1-carboxylate (Intermediate 1e) and commercially available N-2-thiazolyl 4-boronobenzamide to afford the title compound (229 mg, 73.1%).

Example 15

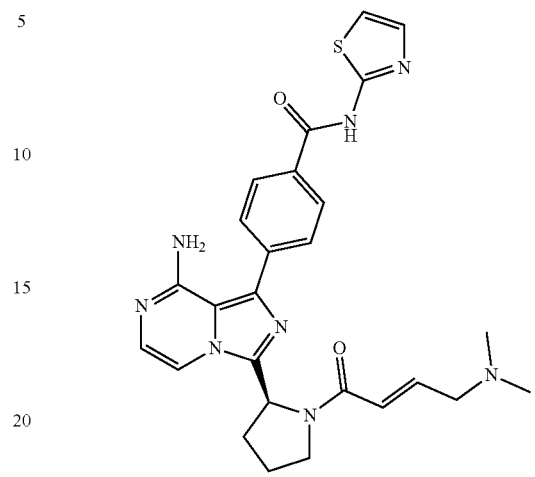

(S,E)-4-(8-Amino-3-(1-(4-(dimethylamino)but-2-enoyl)pyrrolidin-2-yl)imidazo[1,5-a]pyrazin-1-yl)-N-(thiazol-2-yl)benzamide This compound was prepared, in an analogous manner as described in Example 2, from (S)-4-(8-amino-3-(pyrrolidin-2-yl)imidazo[1,5-a]pyrazin-1-yl)-N-(thiazol-2-yl)benzamide (intermediate 20) and (E)-4-(dimethylamino)but-2-enoic acid, to afford the title compound (18.9 mg, 29.7%). Data: UPLC (C) $R_t$: 1.38 min; m/z 517.3 (M+H)$^+$.

Intermediate 21

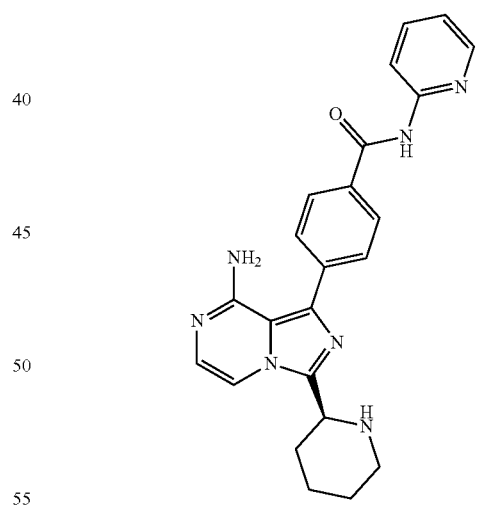

(S)-4-(8-Amino-3-(piperidin-2-yl)imidazo[1,5-a]pyrazin-1-yl)-N-(pyridin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with commercially available 4-(pyridin-2-yl-aminocarbonyl)benzeneboronic acid, in an analogous manner as described for intermediate 2, afforded the title compound (491 mg, 91%).

Example 16

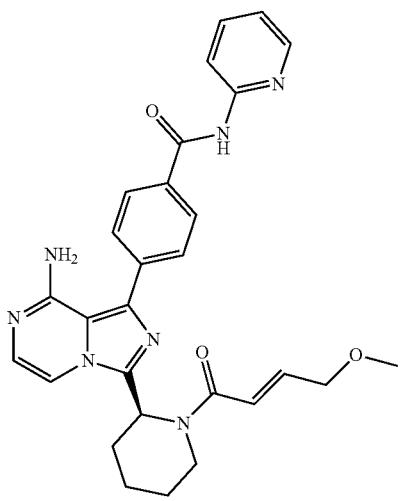 [SMILES: COC/C=C/C(=O)N1CCCC[C@H]1c1nc(-c2ccc(C(=O)Nc3ccccn3)cc2)c2c(N)nccn12]

(S,E)-4-(8-Amino-3-(1-(4-methoxybut-2-enoyl)piperidin-2-yl)imidazo[1,5-a]pyrazin-1-yl)-N-(pyridin-2-yl)benzamide This compound was prepared, in an analogous manner as described in Example 2, from (S)-4-(8-amino-3-(piperidin-2-yl)imidazo[1,5-a]pyrazin-1-yl)-N-(pyridin-2-yl)benzamide (intermediate 21) and (E)-4-methoxybut-2-enoic acid (intermediate 3), to afford the title compound (21.1 mg, 54.3%). Data: LCMS (B) $R_t$: 2.22 min; m/z 512.3 (M+H)$^+$.

Intermediate 22

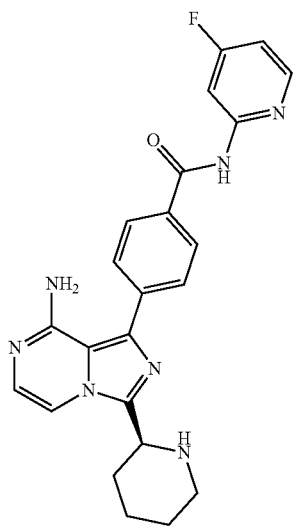 [SMILES: Nc1nccn2c([C@@H]3CCCCN3)nc(-c3ccc(C(=O)Nc4cc(F)ccn4)cc3)c12]

(S)-4-(8-Amino-3-(piperidin-2-yl)imidazo[1,5-a]pyrazin-1-yl)-N-(4-fluoropyridin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(4-fluoropyridin-2-yl)-4-(4,4,5,5-tetramethyl-1,3,2-dioxaborolan-2-yl)benzamide (Intermediate 4), in an analogous manner as described for intermediate 2, afforded the title compound (160 mg, 71.8%).

Example 17

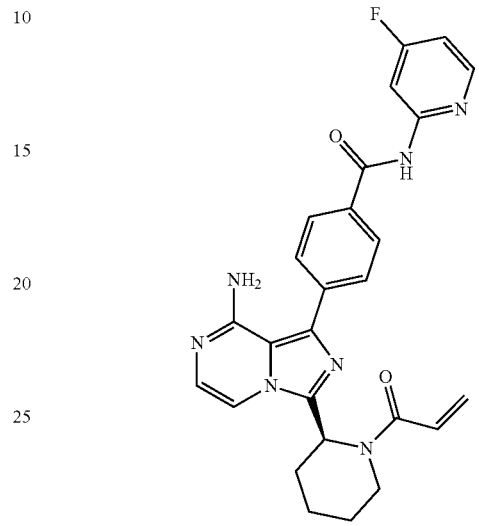

(S)-4-(3-(1-Acryloylpiperidin-2-yl)-8-aminoimidazo[1,5-a]pyrazin-1-yl)-N-(4-fluoropyridin-2-yl)benzamide This compound was prepared, in an analogous manner as described in Example 1, from (S)-4-(8-amino-3-(piperidin-2-yl)imidazo[1,5-a]pyrazin-1-yl)-N-(4-fluoropyridin-2-yl)benzamide (intermediate 22) and acryloylchlroide, to afford the title compound (12 mg, 42.7%). Data: UPLC(C) $R_t$: 2.29 min; m/z 486.3 (M+H)$^+$.

Intermediate 23

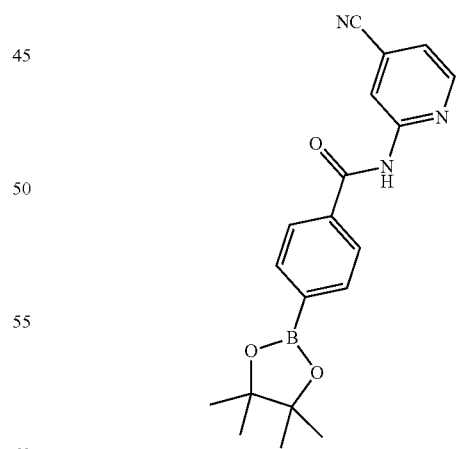

N-(4-Cyanopyridin-2-yl)-4-(4,4,5,5-tetramethyl-1,3,2-dioxaborolan-2-yl)benzamide This compound was prepared, in an analogous manner as described in Intermediate 4, starting from 2-aminoisonicotinonitrile, to afford the title compound (1.3 g, 99%).

Intermediate 24

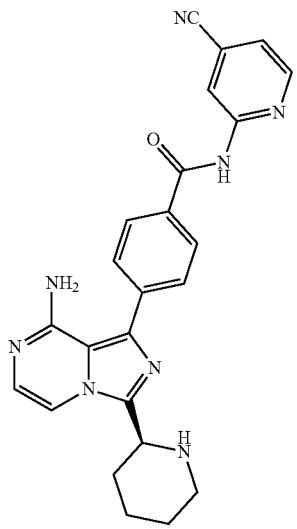 [SMILES: N#Cc1ccnc(NC(=O)c2ccc(-c3nc([C@@H]4CCCCN4)n4ccnc(N)c34)cc2)c1]

(S)-4-(8-Amino-3-(piperidin-2-yl)imidazo[1,5-a]pyrazin-1-yl)-N-(4-cyanopyridin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(4-cyanopyridin-2-yl)-4-(4,4,5,5-tetramethyl-1,3,2-dioxaborolan-2-yl)benzamide (Intermediate 23), in an analogous manner as described for intermediate 2, afforded the title compound (82 mg, 35.7%).

Example 18

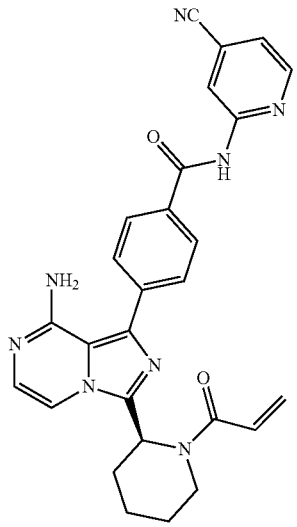 [SMILES: C=CC(=O)N1CCCC[C@H]1c1nc(-c2ccc(C(=O)Nc3cc(C#N)ccn3)cc2)c2c(N)nccn12]

(S)-4-(3-(1-Acryloylpiperidin-2-yl)-8-aminoimidazo[1,5-a]pyrazin-1-yl)-N-(4-cyanopyridin-2-yl)benzamide This compound was prepared, in an analogous manner as described in Example 1, from (S)-4-(8-amino-3-(piperidin-2-yl)imidazo[1,5-a]pyrazin-1-yl)-N-(4-cyanopyridin-2-yl)benzamide (intermediate 24) and acryloylchloride, to afford the title compound (4.8 mg, 10.4%). Data: UPLC(C) $R_t$: 2.31 min.

Intermediate 25

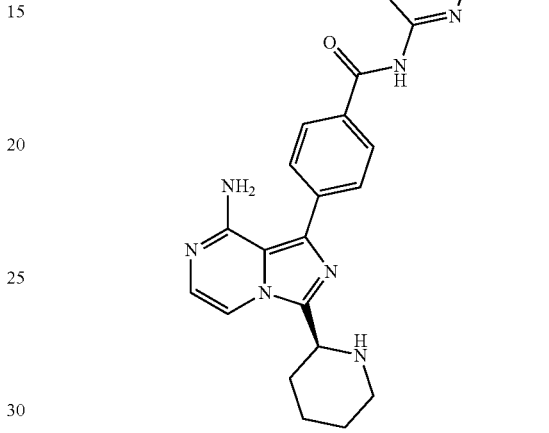

(S)-4-(8-Amino-3-(piperidin-2-yl)imidazo[1,5-a]pyrazin-1-yl)-N-(4-(trifluoromethyl)pyridin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with 4-(4,4,5,5-tetramethyl-1,3,2-dioxaborolan-2-yl)-N-(4-(trifluoromethyl)pyridin-2-yl)benzamide (Intermediate 10), in an analogous manner as described for intermediate 2, afforded the title compound (144 mg, 59.1%).

Example 19

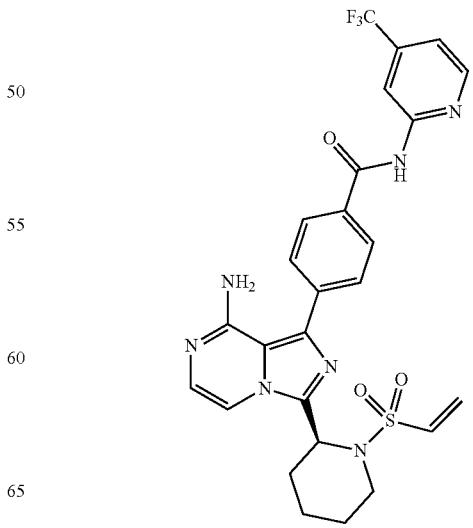

(S)-4-(8-Amino-3-(1-(vinylsulfonyl)piperidin-2-yl)imidazo[1,5-a]pyrazin-1-yl)-N-(4-(trifluoromethyl)pyridin-2-yl)benzamide This compound was prepared, in an analogous manner as described in Example 1, from (S)-4-(8-amino-3-(piperidin-2-yl)imidazo[1,5-a]pyrazin-1-yl)-N-(4-(trifluoromethyl)pyridin-2-yl)benzamide (intermediate 25) and ethenesulfonyl chloride prepared according to procedures described by King et. al. in Can. J. Chem. 66 (1988) pp 1109-1116, to afford the title compound (6.1 mg, 20.5%). Data: UPLC(B) $R_t$: 1.24 min; m/z 572.2 (M+H)⁺.

Intermediate 26

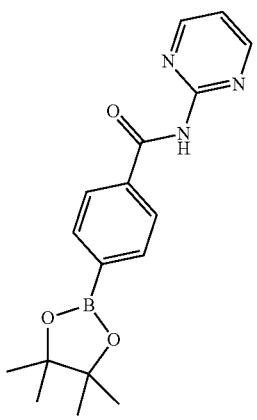 [SMILES: CC1(C)OB(c2ccc(C(=O)Nc3ncccn3)cc2)OC1(C)C]

N-(Pyrimidin-2-yl)-4-(4,4,5,5-tetramethyl-1,3,2-dioxaborolan-2-yl)benzamide

This compound was prepared, in an analogous manner as described in Intermediate 14, starting from 2-aminopyrimidine, to afford the title compound (855 mg, 42.6%).

Intermediate 27

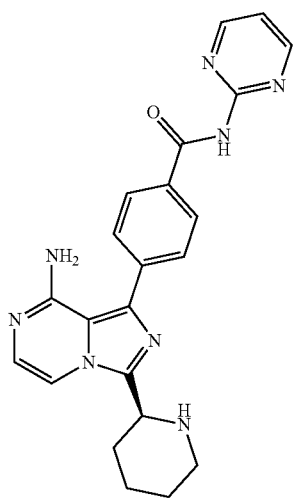 [SMILES: Nc1nccn2c([C@@H]3CCCCN3)nc(-c3ccc(C(=O)Nc4ncccn4)cc3)c12]

(S)-4-(8-Amino-3-(piperidin-2-yl)imidazo[1,5-a]pyrazin-1-yl)-N-(pyrimidin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(pyrimidin-2-yl)-4-(4,4,5,5-tetramethyl-1,3,2-dioxaborolan-2-yl)benzamide (Intermediate 26), in an analogous manner as described for intermediate 2, afforded the title compound (100.8 mg, 95.4%).

Example 20

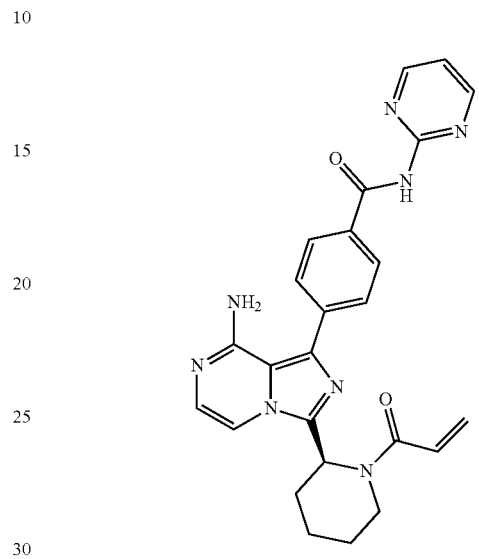

(S)-4-(3-(1-Acryloylpiperidin-2-yl)-8-aminoimidazo[1,5-a]pyrazin-1-yl)-N-(pyrimidin-2-yl)benzamide This compound was prepared, in an analogous manner as described in Example 1, from (S)-4-(8-amino-3-(piperidin-2-yl)imidazo[1,5-a]pyrazin-1-yl)-N-(pyrimidin-2-yl)benzamide (intermediate 27) and acryloylchloride, to afford the title compound (5.9 mg, 26.2%). Data: UPLC(C) $R_t$: 1.70 min; m/z 469.3 (M+H)⁺.

Intermediate 28

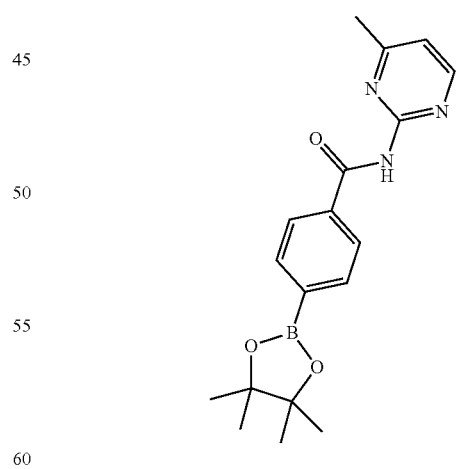

N-(4-Methylpyrimidin-2-yl)-4-(4,4,5,5-tetramethyl-1,3,2-dioxaborolan-2-yl)benzamide This compound was prepared, in an analogous manner as described in Intermediate 14, starting from 2-amino-4-methylpyrimidine, to afford the title compound (420 mg, 60.6%).

Intermediate 29

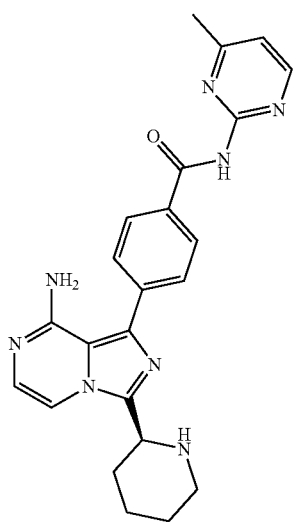 [SMILES: Cc1ccnc(NC(=O)c2ccc(-c3nc([C@@H]4CCCCN4)n4ccnc(N)c34)cc2)n1]

(S)-4-(8-Amino-3-(piperidin-2-yl)imidazo[1,5-a]pyrazin-1-yl)-N-(4-methylpyrimidin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(4-methylpyrimidin-2-yl)-4-(4,4,5,5-tetramethyl-1,3,2-dioxaborolan-2-yl)benzamide (Intermediate 28), in an analogous manner as described for intermediate 2, afforded the title compound (83 mg, 50.4%).

Example 21

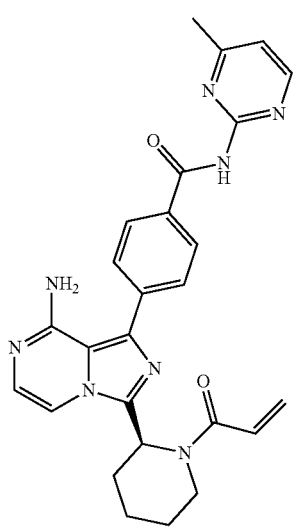 [SMILES: C=CC(=O)N1CCCC[C@H]1c1nc(-c2ccc(C(=O)Nc3nccc(C)n3)cc2)c2c(N)nccn12]

(S)-4-(3-(1-Acryloylpiperidin-2-yl)-8-aminoimidazo[1,5-a]pyrazin-1-yl)-N-(4-methylpyrimidin-2-yl)benzamide This compound was prepared, in an analogous manner as described in Example 1, from (S)-4-(8-amino-3-(piperidin-2-yl)imidazo[1,5-a]pyrazin-1-yl)-N-(4-methylpyrimidin-2-yl)benzamide (intermediate 29) and acryloylchloride, to afford the title compound (4.5 mg, 27.4%). Data: UPLC(C) $R_t$: 1.79 min; m/z 483.3 (M+H)$^+$.

Intermediate 30

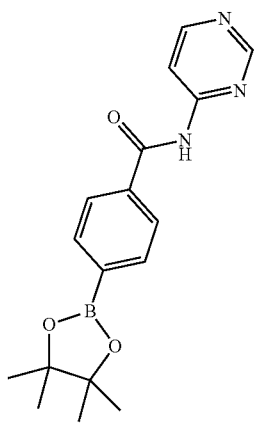 [SMILES: CC1(C)OB(c2ccc(C(=O)Nc3ccncn3)cc2)OC1(C)C]

N-(Pyrimidin-4-yl)-4-(4,4,5,5-tetramethyl-1,3,2-dioxaborolan-2-yl)benzamide

This compound was prepared, in an analogous manner as described in Intermediate 14, starting from 4-aminopyrimidine, to afford the title compound (1 g, 59.4%).

Intermediate 31

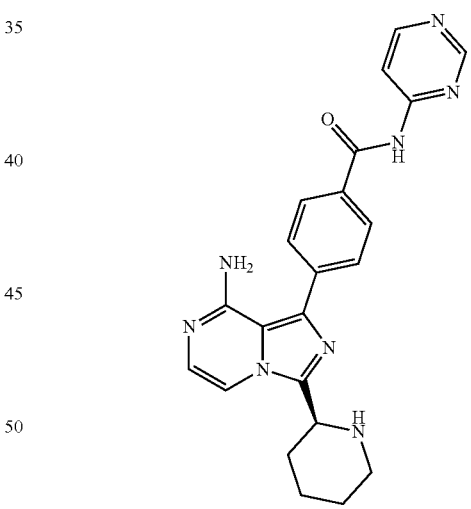

(S)-4-(8-Amino-3-(piperidin-2-yl)imidazo[1,5-a]pyrazin-1-yl)-N-(pyrimidin-4-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(pyrimidin-4-yl)-4-(4,4,5,5-tetramethyl-1,3,2-dioxaborolan-2-yl)benzamide (Intermediate 30), in an analogous manner as described for intermediate 2, afforded the title compound (66 mg, 42.8%).

Example 22

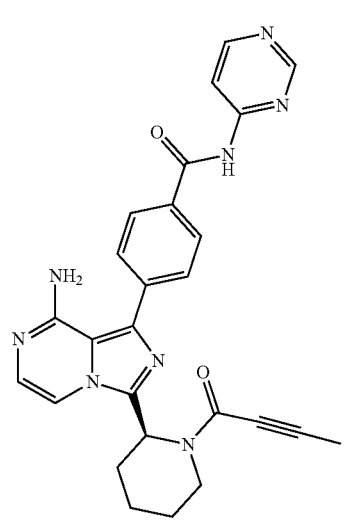 [SMILES: CC#CC(=O)N1CCCC[C@H]1c1nc(-c2ccc(C(=O)Nc3ccncn3)cc2)c2c(N)nccn12]

(S)-4-(8-Amino-3-(1-but-2-ynoylpiperidin-2-yl)imidazo[1,5-a]pyrazin-1-yl)-N-(pyrimidin-4-yl)benzamide This compound was prepared, in an analogous manner as described in Example 2, from (S)-4-(8-amino-3-(piperidin-2-yl)imidazo[1,5-a]pyrazin-1-yl)-N-(pyrimidin-4-yl)benzamide (intermediate 31) and 2-butynoic acid, to afford the title compound (10.3 mg, 26.9%). Data: UPLC(C) R$_t$: 1.91 min; m/z 481.3 (M+H)$^+$.

Intermediate 32

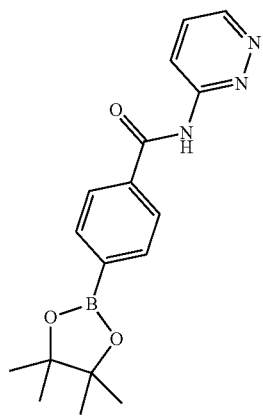 [SMILES: CC1(C)OB(c2ccc(C(=O)Nc3cccnn3)cc2)OC1(C)C]

N-(Pyridazin-3-yl)-4-(4,4,5,5-tetramethyl-1,3,2-dioxaborolan-2-yl)benzamide

This compound was prepared, in an analogous manner as described in Intermediate 14, starting from 3-aminopyridazine, to afford the title compound (1.25 g, 71.3%).

Intermediate 33

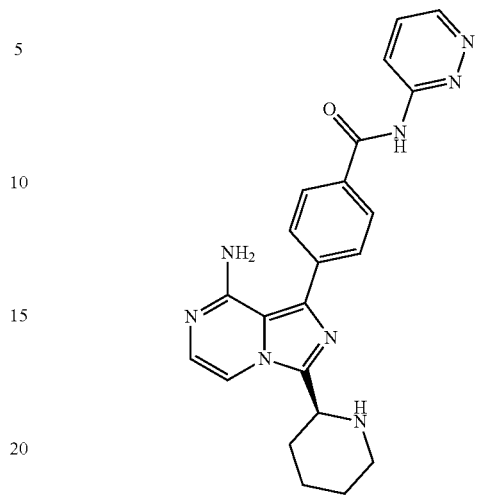

(S)-4-(8-Amino-3-(piperidin-2-yl)imidazo[1,5-a]pyrazin-1-yl)-N-(pyridazin-3-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(pyridazin-3-yl)-4-(4,4,5,5-tetramethyl-1,3,2-dioxaborolan-2-yl)benzamide (Intermediate 32) and deprotection, in an analogous manner as described for intermediate 2, afforded the title compound (258 mg, 85%).

Example 23

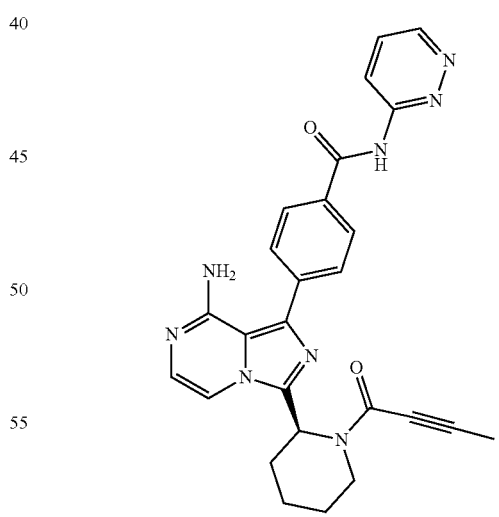

(S)-4-(8-Amino-3-(1-but-2-ynoylpiperidin-2-yl)imidazo[1,5-a]pyrazin-1-yl)-N-(pyridazin-3-yl)benzamide This compound was prepared, in an analogous manner as described in Example 2, from (S)-4-(8-amino-3-(piperidin-2-yl)imidazo[1,5-a]pyrazin-1-yl)-N-(pyridazin-3-yl)benzamide (intermediate 33) and 2-butynoic acid, to afford the title compound (11 mg, 31.8%). Data: UPLC(C) R$_t$: 1.92 min; m/z 481.3 (M+H)$^+$.

Intermediate 34

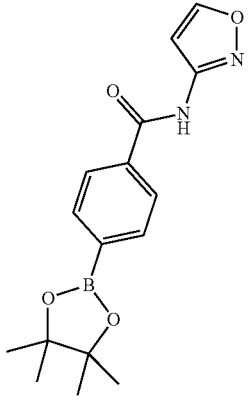 [SMILES: CC1(C)OB(c2ccc(C(=O)Nc3ccon3)cc2)OC1(C)C]

N-(Isoxazol-3-yl)-4-(4,4,5,5-tetramethyl-1,3,2-dioxaborolan-2-yl)benzamide

This compound was prepared, in an analogous manner as described in Intermediate 14, starting from 3-aminoisoxazole, to afford the title compound (1.64 g, 95%).

Intermediate 35

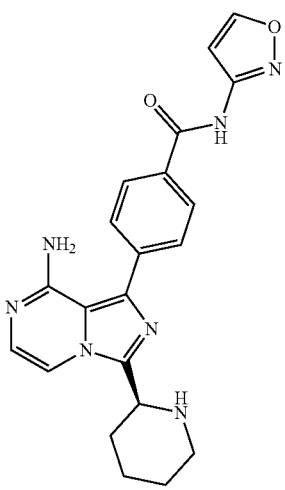 [SMILES: Nc1nccn2c([C@@H]3CCCCN3)nc(-c3ccc(C(=O)Nc4ccon4)cc3)c12]

(S)-4-(8-Amino-3-(piperidin-2-yl)imidazo[1,5-a]pyrazin-1-yl)-N-(isoxazol-3-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(isoxazol-3-yl)-4-(4,4,5,5-tetramethyl-1,3,2-dioxaborolan-2-yl)benzamide (Intermediate 34) and deprotection, in an analogous manner as described for intermediate 2, afforded the title compound (72 mg, 129%).

Example 24

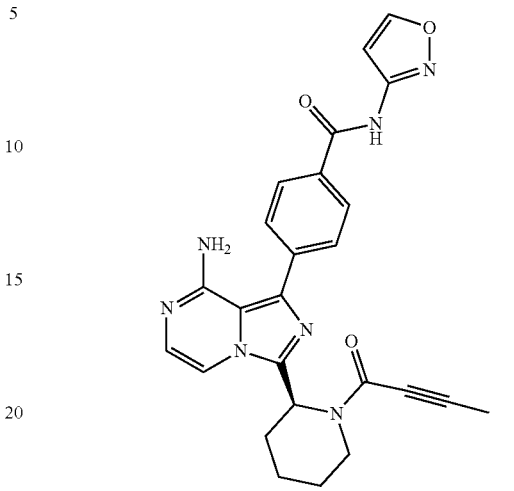

(S)-4-(8-Amino-3-(1-but-2-ynoylpiperidin-2-yl)imidazo[1,5-a]pyrazin-1-yl)-N-(isoxazol-3-yl)benzamide This compound was prepared, in an analogous manner as described in Example 2, from (S)-4-(8-amino-3-(piperidin-2-yl)imidazo[1,5-a]pyrazin-1-yl)-N-(isoxazol-3-yl)benzamide (intermediate 35) and 2-butynoic acid, to afford the title compound (2 mg, 6.6%). Data: UPLC(C) R$_t$: 2.23 min; m/z 470.3 (M+H)$^+$.

Intermediate 36

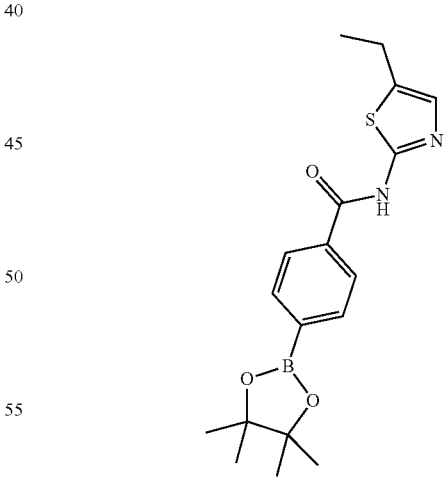

N-(5-Ethylthiazol-2-yl)-4-(4,4,5,5-tetramethyl-1,3,2-dioxaborolan-2-yl)benzamide This compound was prepared, in an analogous manner as described in Intermediate 4, starting from 5-ethylthiazol-2-amine, to afford the title compound (191 mg, 34.2%).

Intermediate 37

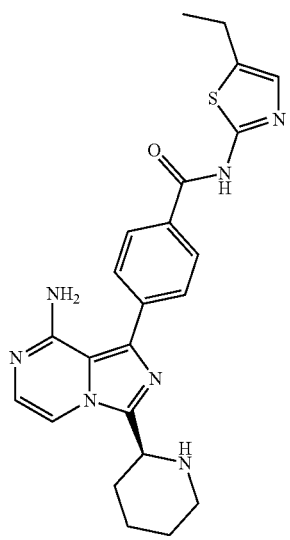 [SMILES: CCc1cnc(NC(=O)c2ccc(-c3nc([C@@H]4CCCCN4)n4ccnc(N)c34)cc2)s1]

(S)-4-(8-Amino-3-(piperidin-2-yl)imidazo[1,5-a]pyrazin-1-yl)-N-(5-ethylthiazol-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with N-(5-ethylthiazol-2-yl)-4-(4,4,5,5-tetramethyl-1,3,2-dioxaborolan-2-yl)benzamide (Intermediate 36) and deprotection, in an analogous manner as described for intermediate 2, afforded the title compound (146 mg, 52.4%).

Example 25

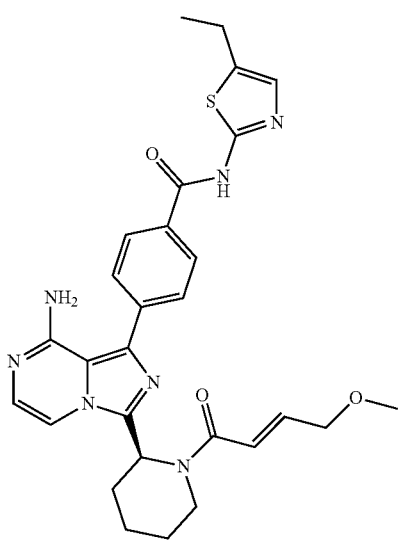 [SMILES: CCc1cnc(NC(=O)c2ccc(-c3nc([C@@H]4CCCCN4C(=O)/C=C/COC)n4ccnc(N)c34)cc2)s1]

(S,E)-4-(8-Amino-3-(1-(4-methoxybut-2-enoyl)piperidin-2-yl)imidazo[1,5-a]pyrazin-1-yl)-N-(5-ethylthiazol-2-yl)benzamide This compound was prepared, in an analogous manner as described in Example 2, from (S)-4-(8-amino-3-(piperidin-2-yl)imidazo[1,5-a]pyrazin-1-yl)-N-(5-ethylthiazol-2-yl)benzamide (intermediate 37) and (E)-4-methoxybut-2-enoic acid (Intermediate 3), to afford the title compound (11.7 mg, 47.6%). Data: UPLC(C) R$_t$: 2.59 min; m/z 546.3 (M+H)$^+$.

Intermediate 38

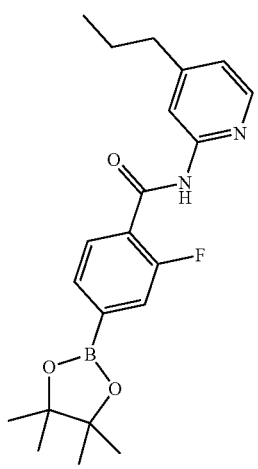 [SMILES: CCCc1ccnc(NC(=O)c2ccc(B3OC(C)(C)C(C)(C)O3)cc2F)c1]

2-Fluoro-N-(4-propylpyridin-2-yl)-4-(4,4,5,5-tetramethyl-1,3,2-dioxaborolan-2-yl)benzamide This compound was prepared, in an analogous manner as described in Intermediate 4, starting from commercially available 2-fluoro-4-(4,4,5,5-tetramethyl-1,3,2-dioxaborolan-2-yl)benzoic acid and 4-propyl-pyridin-2-ylamine, to afford the title compound (830 mg, 63.3%).

Intermediate 39

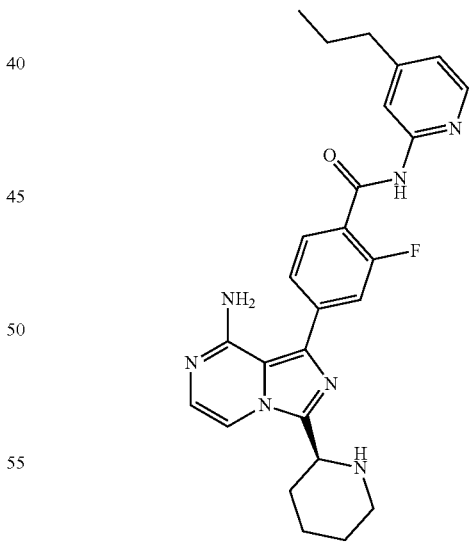

(S)-4-(8-Amino-3-(piperidin-2-yl)imidazo[1,5-a]pyrazin-1-yl)-2-fluoro-N-(4-propylpyridin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with 2-fluoro-N-(4-propylpyridin-2-yl)-4-(4,4,5,5-tetramethyl-1,3,2-dioxaborolan-2-yl)benzamid (Intermediate 38) and deprotection, in an analogous manner as described for intermediate 2, afforded the title compound (75.4 mg, 62%).

Example 26

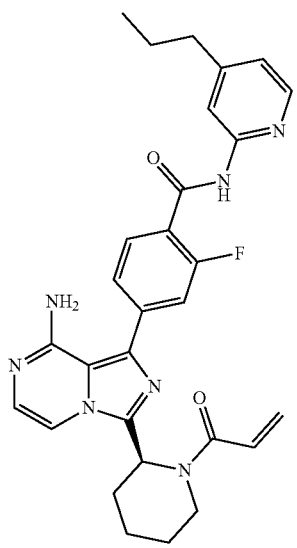 [SMILES: C=CC(=O)N1CCCC[C@H]1c1nc(-c2ccc(C(=O)Nc3cc(CCC)ccn3)c(F)c2)c2c(N)nccn12]

(S)-4-(3-(1-Acryloylpiperidin-2-yl)-8-aminoimidazo[1,5-a]pyrazin-1-yl)-2-fluoro-N-(4-propylpyridin-2-yl)benzamide This compound was prepared, in an analogous manner as described in Example 2, from (S)-4-(8-amino-3-(piperidin-2-yl)imidazo[1,5-a]pyrazin-1-yl)-2-fluoro-N-(4-propylpyridin-2-yl)benzamide (intermediate 39) and acrylic acid, to afford the title compound (5.9 mg, 28.9%). Data: UPLC(C) $R_t$: 2.41 min; m/z 528.4 (M+H)$^+$.

Intermediate 40

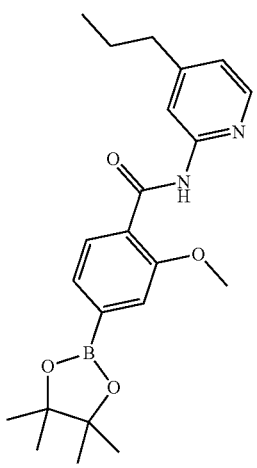 [SMILES: CCCc1ccnc(NC(=O)c2ccc(B3OC(C)(C)C(C)(C)O3)cc2OC)c1]

2-Methoxy-N-(4-propylpyridin-2-yl)-4-(4,4,5,5-tetramethyl-1,3,2-dioxaborolan-2-yl)benzamide This compound was prepared, in an analogous manner as described in Intermediate 14, starting from commercially available 4-bromo-2-methoxybenzoic acid and 4-propylpyridin-2-ylamine, to afford the title compound (240 mg, 15.1%).

Intermediate 41

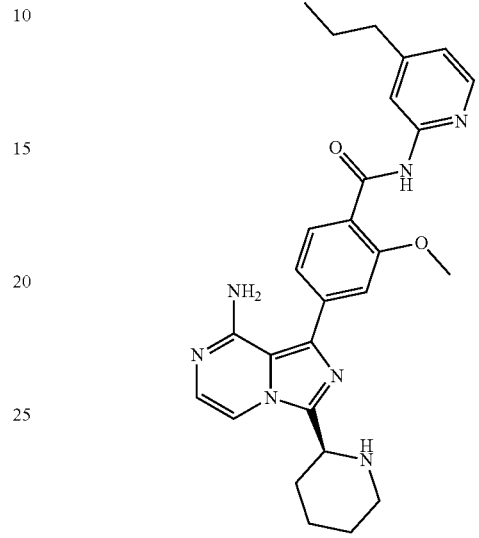

(S)-4-(8-Amino-3-(piperidin-2-yl)imidazo[1,5-a]pyrazin-1-yl)-2-methoxy-N-(4-propylpyridin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with 2-methoxy-N-(4-propylpyridin-2-yl)-4-(4,4,5,5-tetramethyl-1,3,2-dioxaborolan-2-yl)benzamide (Intermediate 40) and deprotection, in an analogous manner as described for intermediate 2, afforded the title compound (74.5 mg, 75%).

Example 27

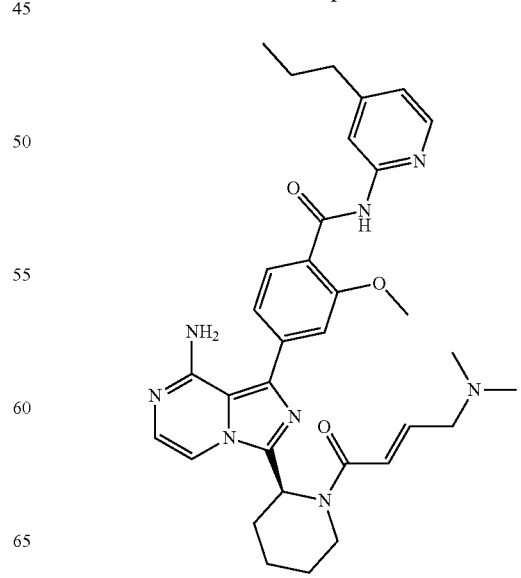

(S,E)-4-(8-Amino-3-(1-(4-(dimethylamino)but-2-enoyl)piperidin-2-yl)imidazo[1,5-a]pyrazin-1-yl)-2-methoxy-N-(4-propylpyridin-2-yl)benzamide This compound was prepared, in an analogous manner as described in Example 2, from (S)-4-(8-amino-3-(piperidin-2-yl)imidazo[1,5-a]pyrazin-1-yl)-2-methoxy-N-(4-propylpyridin-2-yl)benzamide (intermediate 41) and (E)-4-(dimethylamino)but-2-enoic acid, to afford the title compound (13.1 mg, 38.4%). Data: UPLC(C) R$_t$: 1.86 min; m/z 597.4 (M+H)$^+$.

Intermediate 42

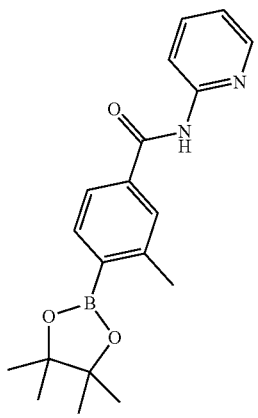 [SMILES: Cc1cc(C(=O)Nc2ccccn2)ccc1B1OC(C)(C)C(C)(C)O1]

3-Methyl-N-(pyridin-2-yl)-4-(4,4,5,5-tetramethyl-1,3,2-dioxaborolan-2-yl)benzamide This compound was prepared, in an analogous manner as described in Intermediate 14, starting from commercially available 4-bromo-3-methylbenzoic acid and 2-aminopyridine, to afford the title compound (2.5 g, 71.3%).

Intermediate 43

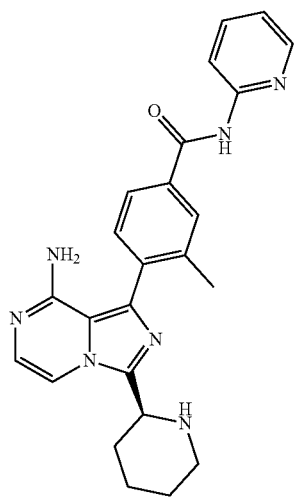 [SMILES: Cc1cc(C(=O)Nc2ccccn2)ccc1-c1nc([C@@H]2CCCCN2)n2ccnc(N)c12]

4-(8-Amino-3-((S)-piperidin-2-yl)imidazo[1,5-a]pyrazin-1-yl)-3-methyl-N-(pyridin-2-yl)benzamide This intermediate was prepared, in an analogous manner as described for intermediate 1, from (S)-1-(benzyloxycarbonyl)piperidine-2-carboxylic acid to obtain (S)-benzyl 2-(8-amino-1-bromoimidazo[1,5-a]pyrazin-3-yl)piperidine-1-carboxylate. Subsequent reaction with 3-methyl-N-(pyridin-2-yl)-4-(4,4,5,5-tetramethyl-1,3,2-dioxaborolan-2-yl)benzamide (Intermediate 42) and deprotection, in an analogous manner as described for intermediate 2, afforded the title compound (150 mg, 71.7%).

Example 28

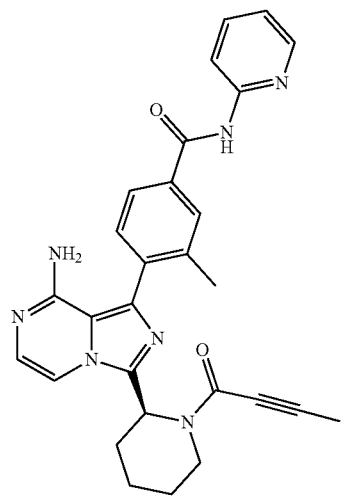 [SMILES: CC#CC(=O)N1CCCC[C@H]1c1nc(-c2ccc(C(=O)Nc3ccccn3)cc2C)c2c(N)nccn12]

4-(8-Amino-3-((S)-1-but-2-ynoylpiperidin-2-yl)imidazo[1,5-a]pyrazin-1-yl)-3-methyl-N-(pyridin-2-yl)benzamide This compound was prepared, in an analogous manner as described in Example 2, from 4-(8-amino-3-((S)-piperidin-2-yl)imidazo[1,5-a]pyrazin-1-yl)-3-methyl-N-(pyridin-2-yl)benzamide (intermediate 43) and 2-butynoic acid, to afford the title compound (13.7 mg, 59.1%). Data: UPLC(C) R$_t$: 2.28 min; m/z 494.3 (M+H)$^+$.

Intermediate 44

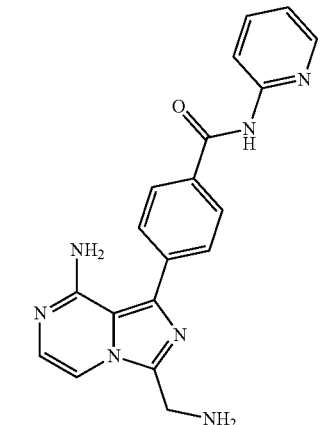

4-(8-Amino-3-(aminomethyl)imidazo[1,5-a]pyrazin-1-yl)-N-(pyridin-2-yl)benzamide This intermediate was prepared, in an analogous manner as described for intermediate 1, from Z-Gly-OH to obtain benzyl (8-amino-1-bromoimidazo[1,5-a]pyrazin-3-yl)methylcarbamate. Subsequent reaction with commercially available 4-(pyridin-2-yl-aminocarbonyl)benzeneboronic acid, in an analogous manner as described for intermediate 2, afforded the title compound (261 mg, 81%).

Example 29

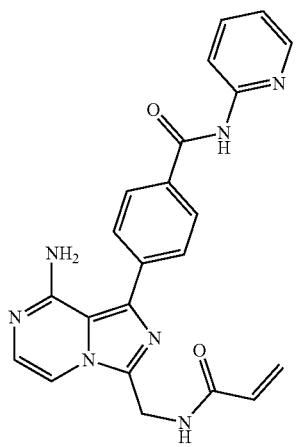 [SMILES: C=CC(=O)NCc1nc(-c2ccc(C(=O)Nc3ccccn3)cc2)c2c(N)nccn12]

4-(3-(Acrylamidomethyl)-8-aminoimidazo[1,5-a]pyrazin-1-yl)-N-(pyridin-2-yl)benzamide This compound was prepared, in an analogous manner as described in Example 1, from 4-(8-amino-3-(aminomethyl)imidazo[1,5-a]pyrazin-1-yl)-N-(pyridin-2-yl)benzamide (intermediate 44) and acryloylchloride, to afford the title compound (1.7 mg, 4%). Data: UPLC(C) $R_t$: 1.22 min; m/z 414.2 (M+H)$^+$.

Intermediate 45

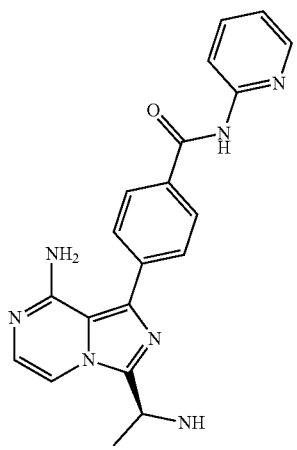 [SMILES: C[C@H](N)c1nc(-c2ccc(C(=O)Nc3ccccn3)cc2)c2c(N)nccn12]

(S)-4-(8-Amino-3-(1-aminoethyl)imidazo[1,5-a]pyrazin-1-yl)-N-(pyridin-2-yl)benzamide This intermediate was prepared, in an analogous manner as described for intermediate 1, from Z-Ala-OH to obtain benzyl (S)-benzyl 1-(8-amino-1-bromoimidazo[1,5-a]pyrazin-3-yl)ethylcarbamate. Subsequent reaction with commercially available 4-(pyridin-2-yl-aminocarbonyl)benzeneboronic acid and deprotection with 33% HBr/HOAc, in an analogous manner as described for intermediate 2, afforded the title compound (133.6 mg, 80%).

Example 30

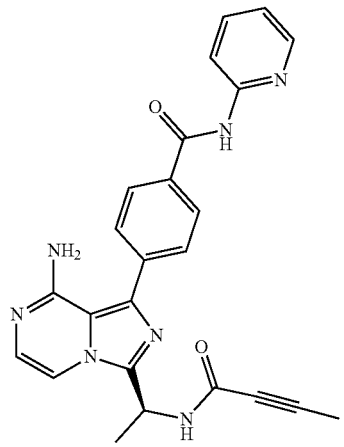 [SMILES: CC#CC(=O)N[C@@H](C)c1nc(-c2ccc(C(=O)Nc3ccccn3)cc2)c2c(N)nccn12]

(S)-4-(8-Amino-3-(1-but-2-ynamidoethyl)imidazo[1,5-a]pyrazin-1-yl)-N-(pyridin-2-yl)benzamide This compound was prepared, in an analogous manner as described in Example 2, from (S)-4-(8-amino-3-(1-aminoethyl)imidazo[1,5-a]pyrazin-1-yl)-N-(pyridin-2-yl)benzamide (intermediate 45) and 2-butynoic acid, to afford the title compound (9.5 mg, 26.9%). Data: UPLC(C) $R_t$: 1.38 min; m/z 440.3 (M+H)$^+$.

Example 31

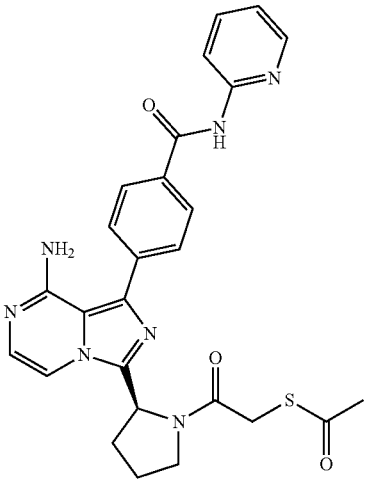 [SMILES: CC(=O)SCC(=O)N1CCC[C@H]1c1nc(-c2ccc(C(=O)Nc3ccccn3)cc2)c2c(N)nccn12]

(S)—S-2-(2-(8-Amino-1-(4-(pyridin-2-ylcarbamoyl)phenyl)imidazo[1,5-a]pyrazin-3-yl)pyrrolidin-1-yl)-2-oxoethyl ethanethioate This compound was prepared, in an analogous manner as described in Example 1, from the compound described in intermediate 2b and 2,5-dioxopyrrolidin-1-yl 2-(acetylthio) acetate, to afford the title compound (12.3 mg, 31.8%). Data: UPLC (C) R$_t$: 1.51 min; m/z 516.3 (M+H)$^+$.

Example 32

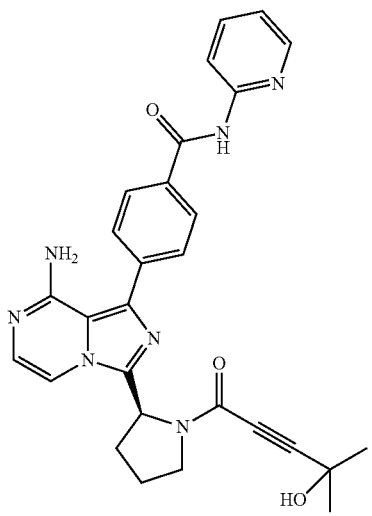 [SMILES: CC(C)(O)C#CC(=O)N1CCC[C@H]1c1nc(-c2ccc(C(=O)Nc3ccccn3)cc2)c2c(N)nccn12]

(S)-4-(8-Amino-3-(1-(4-hydroxy-4-methylpent-2-ynoyl)pyrrolidin-2-yl)imidazo[1,5-a]pyrazin-1-yl)-N-(pyridin-2-yl)benzamide This compound was prepared, in an analogous manner as described in Example 2, from the compound described in intermediate 2b and 4-hydroxy-4-methylpent-2-ynoic acid, to afford the title compound (8.0 mg, 25.1%). Data: UPLC (C) R$_t$: 1.53 min; m/z 510.3 (M+H)$^+$.

Example 33

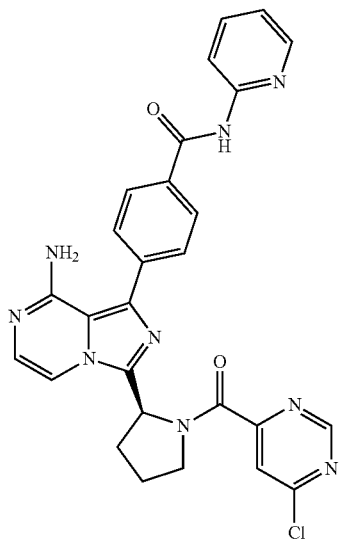 [SMILES: Nc1nccn2c([C@@H]3CCCN3C(=O)c3cc(Cl)ncn3)nc(-c3ccc(C(=O)Nc4ccccn4)cc3)c12]

(S)-4-(8-Amino-3-(1-(6-chloropyrimidine-4-carbonyl)pyrrolidin-2-yl)imidazo[1,5-a]pyrazin-1-yl)-N-(pyridin-2-yl)benzamide This compound was prepared, in an analogous manner as described in Example 2, from the compound described in intermediate 2b and 6-chloropyrimidine-4-carboxylic acid, to afford the title compound (2.5 mg, 6.2%). Data: UPLC (C) R$_t$: 1.64 min; m/z 540.3 (M+H)$^+$.

Example 34

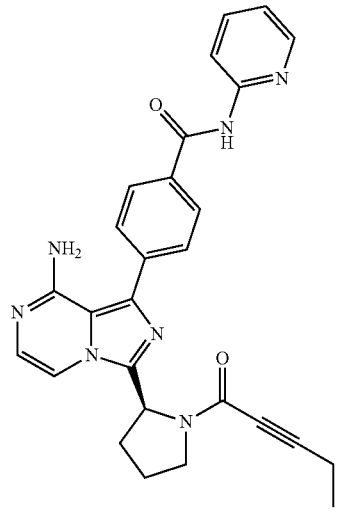 [SMILES: CCC#CC(=O)N1CCC[C@H]1c1nc(-c2ccc(C(=O)Nc3ccccn3)cc2)c2c(N)nccn12]

(S)-4-(8-Amino-3-(1-pent-2-ynoylpyrrolidin-2-yl)imidazo[1,5-a]pyrazin-1-yl)-N-(pyridin-2-yl)benzamide This compound was prepared, in an analogous manner as described in Example 2, from the compound described in intermediate 2b and pent-2-ynoic acid, to afford the title compound (7.4 mg, 24.7%). Data: UPLC (C) R$_t$: 1.73 min; m/z 480.3 (M+H)$^+$.

Example 35

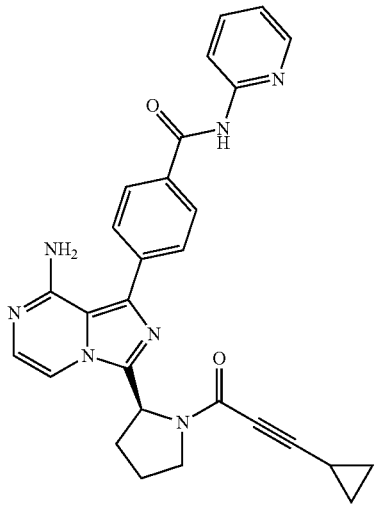 [SMILES: Nc1nccn2c([C@@H]3CCCN3C(=O)C#CC3CC3)nc(-c3ccc(C(=O)Nc4ccccn4)cc3)c12]

(S)-4-(8-Amino-3-(1-(3-cyclopropylpropioloyl)pyr-rolidin-2-yl)imidazo[1,5-a]pyrazin-1-yl)-N-(pyridin-2-yl)benzamide This compound was prepared, in an analogous manner as described in Example 2, from the compound described in intermediate 2b and 3-cyclopropylpropiolic acid, to afford the title compound (8 mg, 26%). Data: UPLC (C) $R_t$: 1.73 min; m/z 492.3 (M+H)$^+$.

Example 36

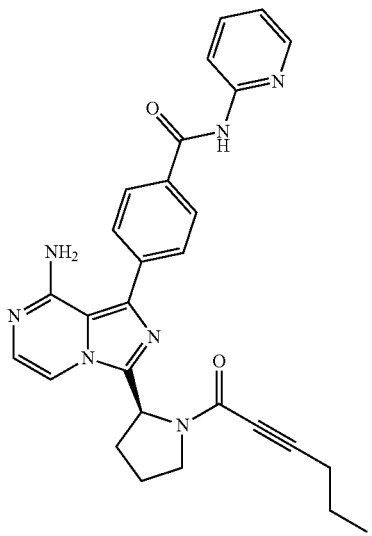 [SMILES: CCCC#CC(=O)N1CCC[C@H]1c1nc(-c2ccc(C(=O)Nc3ccccn3)cc2)c2c(N)nccn12]

(S)-4-(8-Amino-3-(1-hex-2-ynoylpyrrolidin-2-yl)imidazo[1,5-a]pyrazin-1-yl)-N-(pyridin-2-yl)benzamide This compound was prepared, in an analogous manner as described in Example 2, from the compound described in intermediate 2b and hex-2-ynoic acid, to afford the title compound (8.1 mg, 26.2%). Data: UPLC (C) $R_t$: 1.94 min; m/z 494.3 (M+H)$^+$.

Intermediate 46

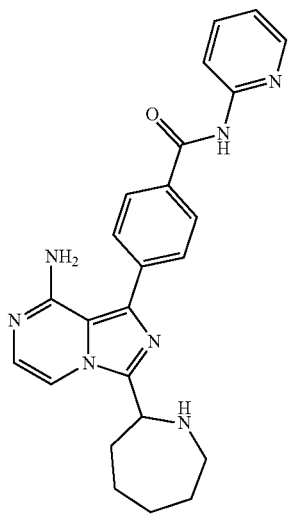 [SMILES: Nc1nccn2c(C3CCCCCN3)nc(-c3ccc(C(=O)Nc4ccccn4)cc3)c12]

4-(8-Amino-3-(azepan-2-yl)imidazo[1,5-a]pyrazin-1-yl)-N-(pyridin-2-yl)benzamide This intermediate was prepared, in an analogous manner as described for intermediate 1, from 1-(benzyloxycarbonyl)azepane-2-carboxylic acid to obtain benzyl 2-(8-amino-1-bromoimidazo[1,5-a]pyrazin-3-yl)azepane-1-carboxylate. Subsequent reaction with commercially available 4-(pyridin-2-yl-aminocarbonyl)benzeneboronic acid, in an analogous manner as described for intermediate 2, afforded the title compound (436 mg, quantitative, crude).

Example 37

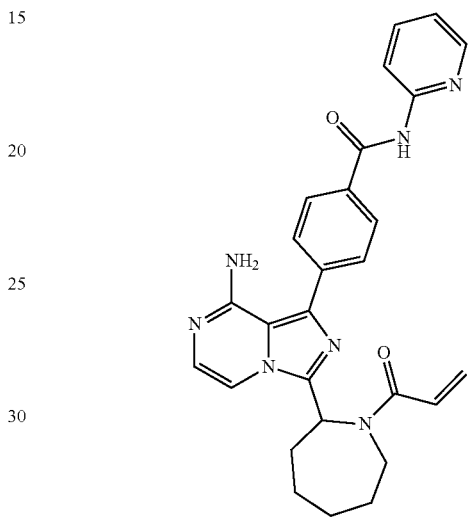

4-(3-(1-Acryloylazepan-2-yl)-8-aminoimidazo[1,5-a]pyrazin-1-yl)-N-(pyridin-2-yl)benzamide This compound was prepared, in an analogous manner as described in Example 1, from 4-(8-amino-3-(azepan-2-yl)imidazo[1,5-a]pyrazin-1-yl)-N-(pyridin-2-yl)benzamide (intermediate 46) and acryloylchloride, to afford the title compound (11 mg, 32.6%). Data: UPLC(C) $R_t$: 1.88 min; m/z 482.3 (M+H)$^+$.

Intermediate 47

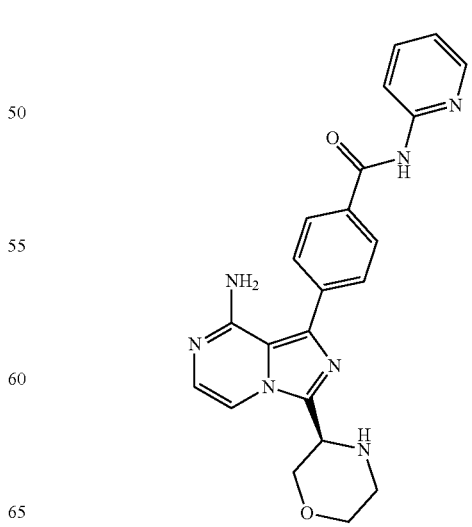

(R)-4-(8-Amino-3-(morpholin-3-yl)imidazo[1,5-a]pyrazin-1-yl)-N-(pyridin-2-yl)benzamide This intermediate was prepared, in an analogous manner as described for intermediate 1, from (S)-4-(benzyloxycarbonyl)morpholine-3-carboxylic acid to obtain (R)-benzyl 3-(8-amino-1-bromoimidazo[1,5-a]pyrazin-3-yl)morpholine-4-carboxylate. Subsequent reaction with commercially available 4-(pyridin-2-yl-aminocarbonyl)benzeneboronic acid, in an analogous manner as described for intermediate 2, and subsequent deprotection using TFA at 60° C., afforded the title compound (62 mg, 69.5%).

Example 38

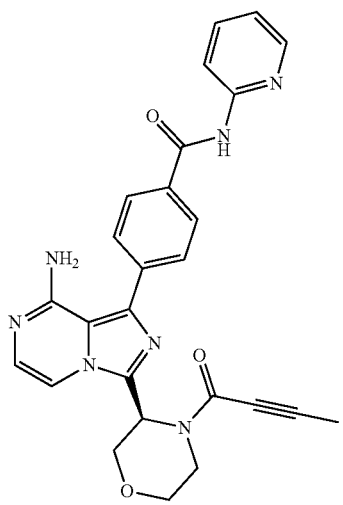 [SMILES: CC#CC(=O)N1CCOC[C@H]1c1nc(-c2ccc(C(=O)Nc3ccccn3)cc2)c2c(N)nccn12]

(R)-4-(8-Amino-3-(4-but-2-ynoylmorpholin-3-yl)imidazo[1,5-a]pyrazin-1-yl)-N-(pyridin-2-yl)benzamide This compound was prepared, in an analogous manner as described in Example 2, from (R)-4-(8-amino-3-(morpholin-3-yl)imidazo[1,5-a]pyrazin-1-yl)-N-(pyridin-2-yl)benzamide (intermediate 47) and 2-butynoic acid, to afford the title compound (4.9 mg, 14.1%). Data: UPLC(C) $R_t$: 1.38 min; m/z 482.3 $(M+H)^+$.

Intermediate 48

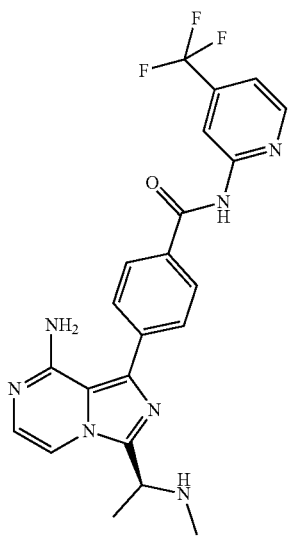 [SMILES: CN[C@@H](C)c1nc(-c2ccc(C(=O)Nc3cc(C(F)(F)F)ccn3)cc2)c2c(N)nccn12]

(S)-4-(8-Amino-3-(1-(methylamino)ethyl)imidazo[1,5-a]pyrazin-1-yl)-N-(4-(trifluoromethyl)pyridin-2-yl)benzamide This intermediate was prepared, in an analogous manner as described for intermediate 1, from (S)-2-((benzyloxycarbonyl)(methyl)amino)propanoic acid to obtain (S)-benzyl 1-(8-amino-1-bromoimidazo[1,5-a]pyrazin-3-yl)ethyl (methyl)carbamate. Subsequent reaction with 4-(4,4,5,5-Tetramethyl-1,3,2-dioxaborolan-2-yl)-N-(4-(trifluoromethyl)pyridin-2-yl)benzamide (Intermediate 10), in an analogous manner as described for intermediate 2, afforded the title compound (71 mg, 64.7%).

Example 39

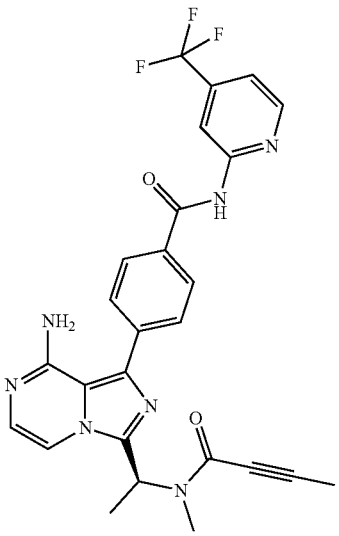 [SMILES: CC#CC(=O)N(C)[C@@H](C)c1nc(-c2ccc(C(=O)Nc3cc(C(F)(F)F)ccn3)cc2)c2c(N)nccn12]

(S)-4-(8-amino-3-(1-(N-methylbut-2-ynamido)ethyl)imidazo[1,5-a]pyrazin-1-yl)-N-(4-(trifluoromethyl)pyridin-2-yl)benzamide This compound was prepared, in an analogous manner as described in Example 2, from (S)-4-(8-amino-3-(1-(methylamino)ethyl)imidazo[1,5-a]pyrazin-1-yl)-N-(4-(trifluoromethyl)pyridin-2-yl)benzamide (intermediate 48) and 2-butynoic acid, to afford the title compound (11.5 mg, 33.4%). Data: UPLC(C) $R_t$: 2.54 min; m/z 522.2 $(M+H)^+$.

Intermediate 49

4-(Dimethylamino)but-2-ynoic acid n-BuLi in hexane (2.5M, 24.06 mmol, 9.62 mL) was slowly added to a solution of N,N-dimethylprop-2-yn-1-amine (24.06 mmol, 2.59 mL, 2 g) in dry THF (10 mL) at −78° C. The mixture was stirred for 1 h at −78° C., then crushed $CO_2$ (241 mmol, 10.59 g) was added in one portion and the reaction mixture was stirred for an additional 10 min. The resulting solution was poured into water and washed with ethyl acetate. The aqueous layer was evaporated in vacuo to give the crude amino acid. This was dissolved in methanol, and the insoluble salts were removed via filtration. The filtrate was evaporated to give 3.25 g of 4-(dimethylamino)but-2-ynoic acid (106%).

Example 40

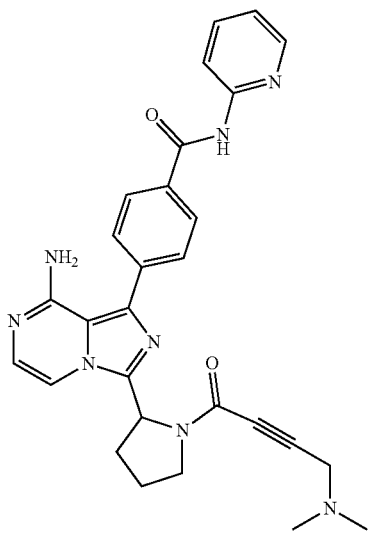 [SMILES: CN(C)CC#CC(=O)N1CCCC1c1nc(-c2ccc(C(=O)Nc3ccccn3)cc2)c2c(N)nccn12]

(S)-4-(8-Amino-3-(1-(4-(dimethylamino)but-2-ynoyl)pyrrolidin-2-yl)imidazo[1,5-a]pyrazin-1-yl)-N-(pyridin-2-yl)benzamide This compound was prepared, in an analogous manner as described in Example 2, from the compound described in intermediate 2b and 4-(dimethylamino)but-2-ynoic acid (Intermediate 49), to afford the title compound (5.6 mg, 12%). Data: UPLC (C) $R_t$: 0.97 min; m/z 509.3 (M+H)$^+$.

Intermediate 50

4-Methoxybut-2-ynoic acid n-BuLi in hexane (2.5M, 28.5 mmol, 11.41 mL) was slowly added to a solution of 3-methoxyprop-1-yne (28.5 mmol, 2.41 mL, 2 g) in dry THF (10 mL) at −78° C. The mixture was stirred for 1 h at −78° C., then crushed CO$_2$ (285 mmol, 12.56 g) was added in one portion and the reaction mixture was stirred for an additional 10 min. The resulting solution was poured into water and washed with ethyl acetate. The aqueous layer was evaporated in vacuo to give the crude amino acid. This was dissolved in methanol, and the insoluble salts were removed via filtration. The filtrate was evaporated to give 3.35 g of 4-methoxybut-2-ynoic acid (103%).

Example 41

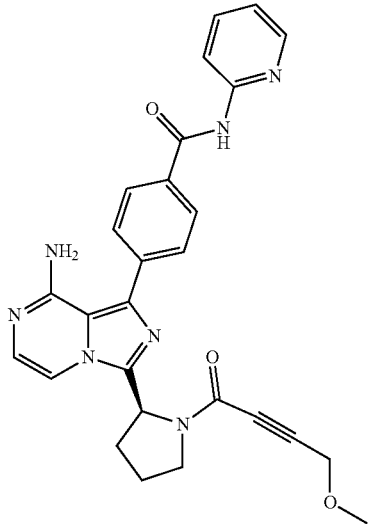 [SMILES: COCC#CC(=O)N1CCC[C@H]1c1nc(-c2ccc(C(=O)Nc3ccccn3)cc2)c2c(N)nccn12]

(S)-4-(8-Amino-3-(1-(4-methoxybut-2-ynoyl)pyrrolidin-2-yl)imidazo[1,5-a]pyrazin-1-yl)-N-(pyridin-2-yl)benzamide This compound was prepared, in an analogous manner as described in Example 2, from the compound described in intermediate 2b and 4-methoxybut-2-ynoic acid (Intermediate 50), to afford the title compound (9.1 mg, 24.7%). Data: UPLC (C) $R_t$: 1.44 min; m/z 496.2 (M+H)$^+$.

The following Examples were synthesized following the methods described for example 1-41.

| Example | Structure | Name | (M + H)+ m/z | UPLC (C) Rt |
|---|---|---|---|---|
| 42 | ![structure] | (S)-4-(3-(1-acryloylpyrrolidin-2-yl)-8-aminoimidazo[1,5-a]pyrazin-1-yl)-N-(4-fluoropyridin-2-yl)benzamide | 472.3 | 2.25 min |

| Example | Structure | Name | (M + H)+ m/z | UPLC (C) Rt |
|---|---|---|---|---|
| 43 | 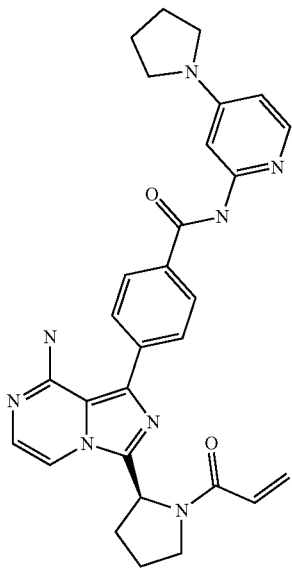 [SMILES: C=CC(=O)N1CCC[C@H]1c1nc(-c2ccc(C(=O)Nc3cc(N4CCCC4)ccn3)cc2)c2c(N)nccn12] | (S)-4-(3-(1-acryloylpyrrolidin-2-yl)-8-aminoimidazo[1,5-a]pyrazin-1-yl)-N-(4-(pyrrolidin-1-yl)pyridin-2-yl)benzamide | 523.3 | 1.72 min |
| 44 | 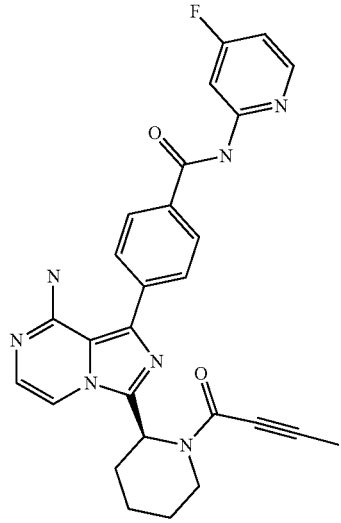 [SMILES: CC#CC(=O)N1CCCC[C@H]1c1nc(-c2ccc(C(=O)Nc3cc(F)ccn3)cc2)c2c(N)nccn12] | (S)-4-(8-amino-3-(1-but-2-ynoylpiperidin-2-yl)imidazo[1,5-a]pyrazin-1-yl)-N-(4-fluoropyridin-2-yl)benzamide | 498.3 | 2.47 min |

-continued

| Example | Structure | Name | (M + H)+ m/z | UPLC (C) Rt |
|---|---|---|---|---|
| 45 | 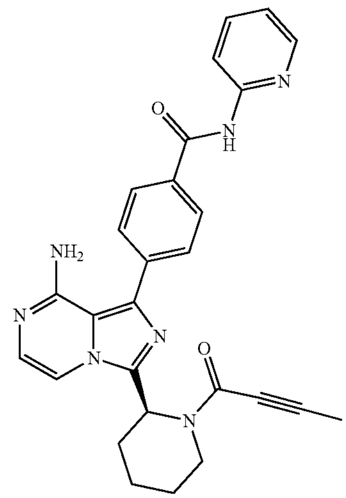 [SMILES: CC#CC(=O)N1CCCC[C@H]1c1nc(-c2ccc(C(=O)Nc3ccccn3)cc2)c2c(N)nccn12] | (S)-4-(8-amino-3-(1-but-2-ynoylpiperidin-2-yl)imidazo[1,5-a]pyrazin-1-yl)-N-(pyridin-2-yl)benzamide | 480.3 | 2.26 min LCMS (B) |
| 46 | 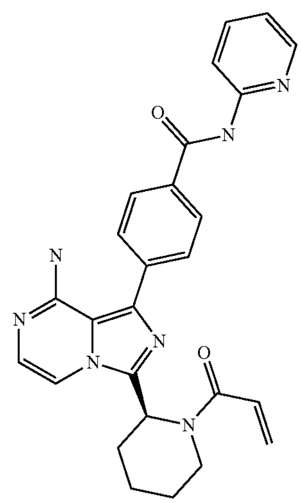 [SMILES: C=CC(=O)N1CCCC[C@H]1c1nc(-c2ccc(C(=O)Nc3ccccn3)cc2)c2c(N)nccn12] | (S)-4-(3-(1-acryloylpiperidin-2-yl)-8-aminoimidazo[1,5-a]pyrazin-1-yl)-N-(pyridin-2-yl)benzamide | 468.3 | 2.49 min |
| 47 | 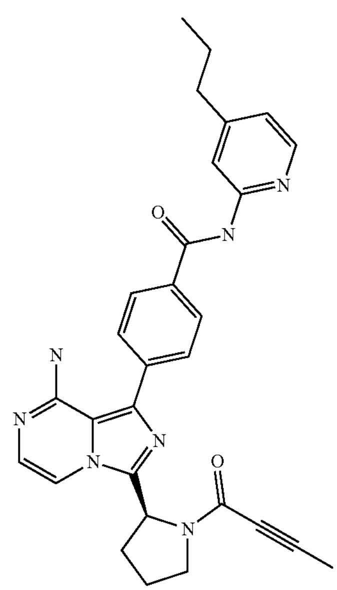 [SMILES: CC#CC(=O)N1CCC[C@H]1c1nc(-c2ccc(C(=O)Nc3cc(CCC)ccn3)cc2)c2c(N)nccn12] | (S)-4-(8-amino-3-(1-but-2-ynoylpyrrolidin-2-yl)imidazo[1,5-a]pyrazin-1-yl)-N-(4-propylpyridin-2-yl)benzamide | 508.3 | 2.00 min |

| Example | Structure | Name | (M + H)+ m/z | UPLC (C) Rt |
|---------|-----------|------|--------------|-------------|
| 48 | 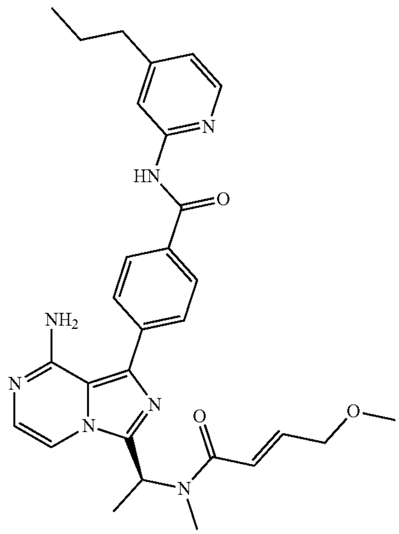 [SMILES: CCCc1ccnc(NC(=O)c2ccc(-c3nc([C@H](C)N(C)C(=O)/C=C/COC)n4ccnc(N)c34)cc2)c1] | (S,E)-4-(8-amino-3-(1-(4-methoxy-N-methylbut-2-enamido)ethyl)imidazo[1,5-a]pyrazin-1-yl)-N-(4-propylpyridin-2-yl)benzamide | 528.3 | 1.89 min |
| 49 | 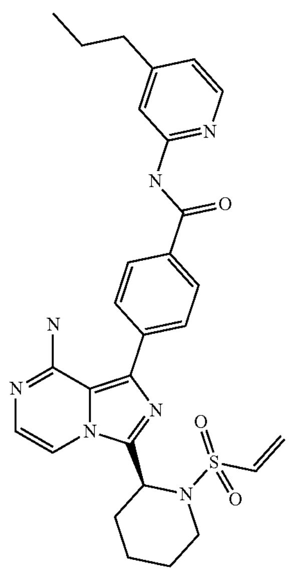 [SMILES: C=CS(=O)(=O)N1CCCC[C@H]1c1nc(-c2ccc(C(=O)Nc3cc(CCC)ccn3)cc2)c2c(N)nccn12] | (S)-4-(8-amino-3-(1-(vinylsulfonyl)piperidin-2-yl)imidazo[1,5-a]pyrazin-1-yl)-N-(4-propylpyridin-2-yl)benzamide | 546.3 | 2.15 min |
| 50 | 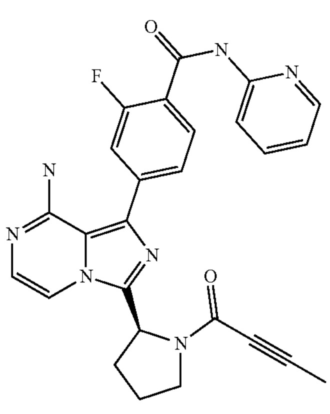 [SMILES: CC#CC(=O)N1CCC[C@H]1c1nc(-c2ccc(C(=O)Nc3ccccn3)c(F)c2)c2c(N)nccn12] | (S)-4-(8-amino-3-(1-but-2-ynoylpyrrolidin-2-yl)imidazo[1,5-a]pyrazin-1-yl)-2-fluoro-N-(pyridin-2-yl)benzamide | 484.3 | 1.84 min |

| Example | Structure | Name | (M + H)+ m/z | UPLC (C) Rt |
|---|---|---|---|---|
| 51 | 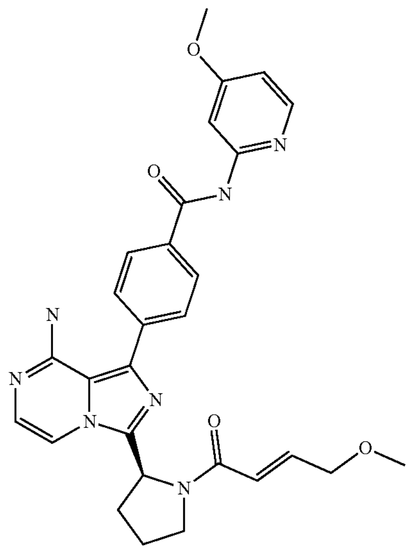 [SMILES: COC/C=C/C(=O)N1CCC[C@H]1c1nc(-c2ccc(C(=O)Nc3cc(OC)ccn3)cc2)c2c(N)nccn12] | (S,E)-4-(8-amino-3-(1-(4-methoxybut-2-enoyl)pyrrolidin-2-yl)imidazo[1,5-a]pyrazin-1-yl)-N-(4-methoxypyridin-2-yl)benzamide | 528.4 | 1.60 min |
| 52 | 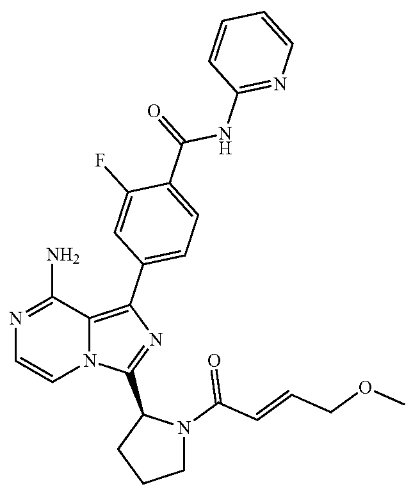 [SMILES: COC/C=C/C(=O)N1CCC[C@H]1c1nc(-c2ccc(C(=O)Nc3ccccn3)c(F)c2)c2c(N)nccn12] | (S,E)-4-(8-amino-3-(1-(4-methoxybut-2-enoyl)pyrrolidin-2-yl)imidazo[1,5-a]pyrazin-1-yl)-2-fluoro-N-(4-methoxypyridin-2-yl)benzamide | 516.3 | 1.79 min |
| 53 | 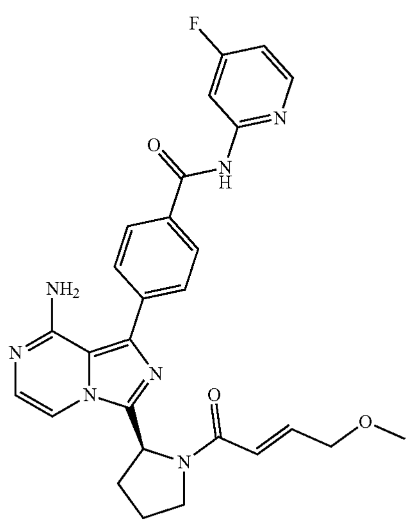 [SMILES: COC/C=C/C(=O)N1CCC[C@H]1c1nc(-c2ccc(C(=O)Nc3cc(F)ccn3)cc2)c2c(N)nccn12] | (S,E)-4-(8-amino-3-(1-(4-methoxybut-2-enoyl)pyrrolidin-2-yl)imidazo[1,5-a]pyrazin-1-yl)-N-(4-fluoropyridin-2-yl)benzamide | 516.3 | 2.31 min |

-continued

| Example | Structure | Name | (M + H)+ m/z | UPLC (C) Rt |
|---|---|---|---|---|
| 54 | 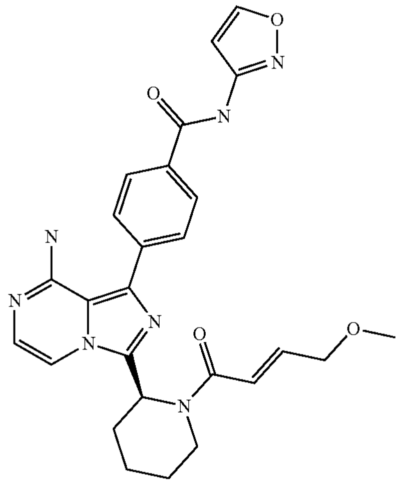 [SMILES: COC/C=C/C(=O)N1CCCC[C@H]1c1nc(-c2ccc(C(=O)Nc3ccon3)cc2)c2c(N)nccn12] | (S,E)-4-(8-amino-3-(1-(4-methoxybut-2-enoyl)piperidin-2-yl)imidazo[1,5-a]pyrazin-1-yl)-N-(isoxazol-3-yl)benzamide | 502.3 | 2.01 min |
| 55 | 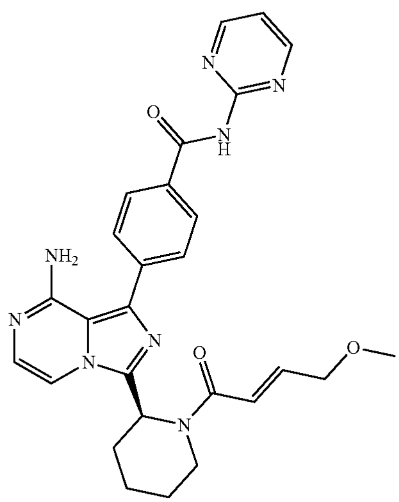 [SMILES: COC/C=C/C(=O)N1CCCC[C@H]1c1nc(-c2ccc(C(=O)Nc3ncccn3)cc2)c2c(N)nccn12] | (S,E)-4-(8-amino-3-(1-(4-methoxybut-2-enoyl)piperidin-2-yl)imidazo[1,5-a]pyrazin-1-yl)-N-(pyrimidin-2-yl)benzamide | 513.3 | 1.79 min |
| 56 | 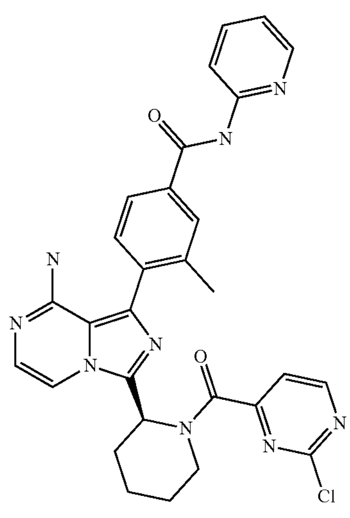 [SMILES: Cc1cc(C(=O)Nc2ccccn2)ccc1-c1nc([C@@H]2CCCCN2C(=O)c2ccnc(Cl)n2)n2ccnc(N)c12] | 4-(8-amino-3-((S)-1-(2-chloropyrimidine-4-carbonyl)piperidin-2-yl)imidazo[1,5-a]pyrazin-1-yl)-3-methyl-N-(pyridin-2-yl)benzamide | 568.3 | 2.23 min |

-continued

| Example | Structure | Name | (M + H)+ m/z | UPLC (C) Rt |
|---|---|---|---|---|
| 57 | 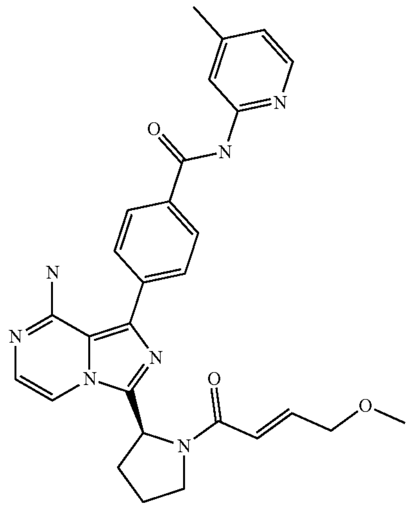 [SMILES: COC/C=C/C(=O)N1CCC[C@H]1c1nc(-c2ccc(C(=O)Nc3cc(C)ccn3)cc2)c2c(N)nccn12] | (S,E)-4-(8-amino-3-(1-(4-methoxybut-2-enoyl)pyrrolidin-2-yl)imidazo[1,5-a]pyrazin-1-yl)-N-(4-methylpyridin-2-yl)benzamide | 512.4 | 1.67 min |
| 58 | 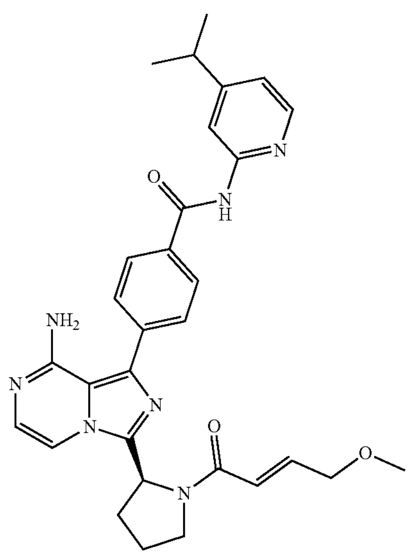 [SMILES: COC/C=C/C(=O)N1CCC[C@H]1c1nc(-c2ccc(C(=O)Nc3cc(C(C)C)ccn3)cc2)c2c(N)nccn12] | (S,E)-4-(8-amino-3-(1-(4-methoxybut-2-enoyl)pyrrolidin-2-yl)imidazo[1,5-a]pyrazin-1-yl)-N-(4-isopropylpyridin-2-yl)benzamide | 540.3 | 1.74 min |
| 59 | 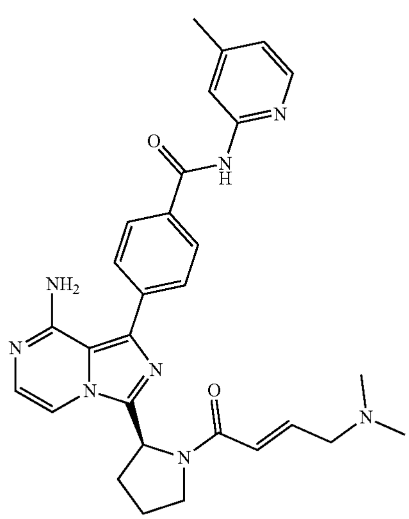 [SMILES: Cc1ccnc(NC(=O)c2ccc(-c3nc([C@@H]4CCCN4C(=O)/C=C/CN(C)C)n4ccnc(N)c34)cc2)c1] | (S,E)-4-(8-amino-3-(1-(4-(dimethylamino)but-2-enoyl)pyrrolidin-2-yl)imidazo[1,5-a]pyrazin-1-yl)-N-(4-methylpyridin-2-yl)benzamide | 525.4 | 1.11 min |

| Example | Structure | Name | (M + H)+ m/z | UPLC (C) Rt |
|---|---|---|---|---|
| 60 | 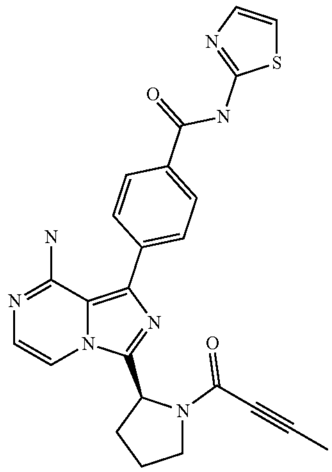 [SMILES: CC#CC(=O)N1CCC[C@H]1c1nc(-c2ccc(C(=O)Nc3nccs3)cc2)c2c(N)nccn12] | (S)-4-(8-amino-3-(1-but-2-ynoylpyrrolidin-2-yl)imidazo[1,5-a]pyrazin-1-yl)-N-(thiazol-2-yl)benzamide | 472.0 | 2.24 min |
| 61 | 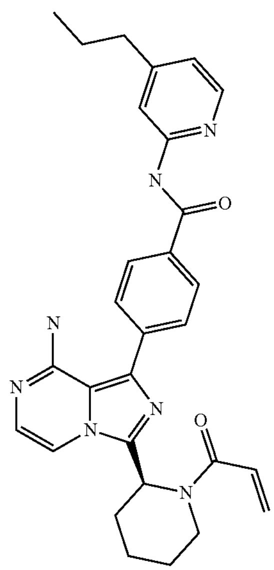 [SMILES: C=CC(=O)N1CCCC[C@H]1c1nc(-c2ccc(C(=O)Nc3cc(CCC)ccn3)cc2)c2c(N)nccn12] | (S)-4-(3-(1-acryloylpiperidin-2-yl)-8-aminoimidazo[1,5-a]pyrazin-1-yl)-N-(4-propylpyridin-2-yl)benzamide | 510.3 | 2.11 min |
| 62 | 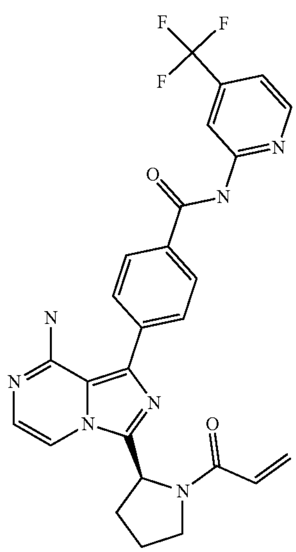 [SMILES: C=CC(=O)N1CCC[C@H]1c1nc(-c2ccc(C(=O)Nc3cc(C(F)(F)F)ccn3)cc2)c2c(N)nccn12] | (S)-4-(3-(1-acryloylpyrrolidin-2-yl)-8-aminoimidazo[1,5-a]pyrazin-1-yl)-N-(4-(trifluoromethyl)pyridin-2-yl)benzamide | 522.0 | 2.37 min |

| Example | Structure | Name | (M + H)+ m/z | UPLC (C) Rt |
|---|---|---|---|---|
| 63 | 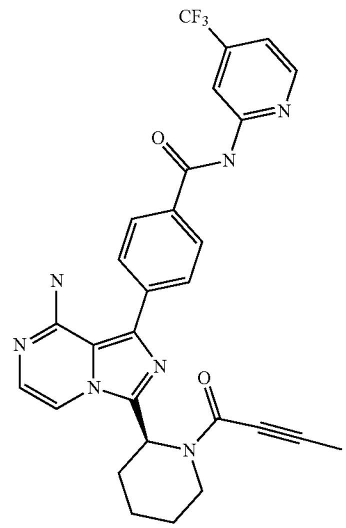 [SMILES: CC#CC(=O)N1CCCC[C@H]1c1nc(-c2ccc(C(=O)Nc3cc(C(F)(F)F)ccn3)cc2)c2c(N)nccn12] | (S)-4-(8-amino-3-(1-but-2-ynoylpiperidin-2-yl)imidazo[1,5-a]pyrazin-1-yl)-N-(4-(trifluoromethyl)pyridin-2-yl)benzamide | 548.3 | 1.09 min UPLC (B) |
| 64 | 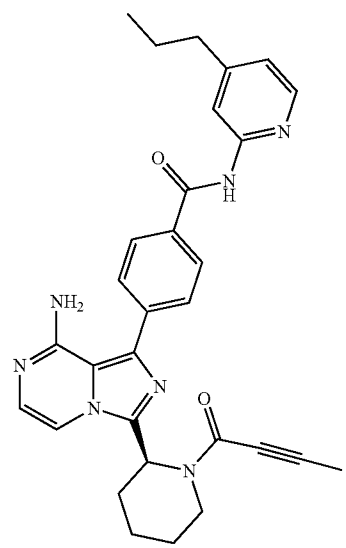 [SMILES: CC#CC(=O)N1CCCC[C@H]1c1nc(-c2ccc(C(=O)Nc3cc(CCC)ccn3)cc2)c2c(N)nccn12] | (S)-4-(8-amino-3-(1-but-2-ynoylpiperidin-2-yl)imidazo[1,5-a]pyrazin-1-yl)-N-(4-propylpyridin-2-yl)benzamide | 522.3 | 2.29 min |
| 65 | 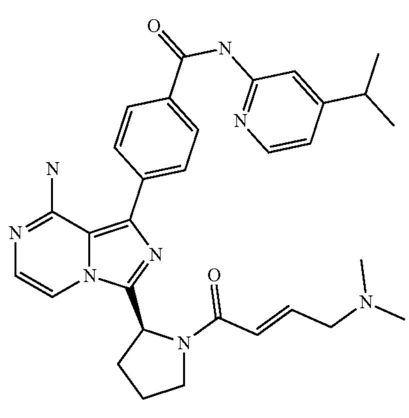 [SMILES: CC(C)c1ccnc(NC(=O)c2ccc(-c3nc([C@@H]4CCCN4C(=O)/C=C/CN(C)C)n4ccnc(N)c34)cc2)c1] | (S,E)-4-(8-amino-3-(1-(4-(dimethylamino)but-2-enoyl)pyrrolidin-2-yl)imidazo[1,5-a]pyrazin-1-yl)-N-(4-isopropylpyridin-2-yl)benzamide | 553.3 | 1.31 min |

-continued

| Example | Structure | Name | (M + H)+ m/z | UPLC (C) Rt |
|---|---|---|---|---|
| 66 | 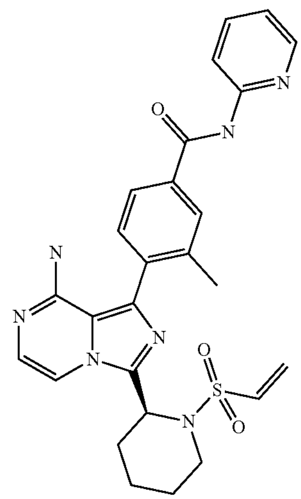 [SMILES: C=CS(=O)(=O)N1CCCC[C@H]1c1nc(-c2ccc(C(=O)Nc3ccccn3)cc2C)c2c(N)nccn12] | 4-(8-amino-3-((S)-1-(vinylsulfonyl)piperidin-2-yl)imidazo[1,5-a]pyrazin-1-yl)-3-methyl-N-(pyridin-2-yl)benzamide | 518.3 | 2.20 min |
| 67 | 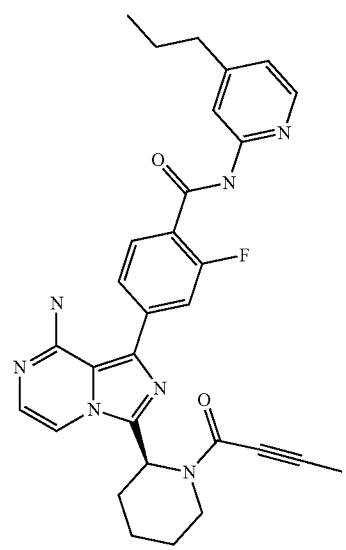 [SMILES: CC#CC(=O)N1CCCC[C@H]1c1nc(-c2ccc(C(=O)Nc3cc(CCC)ccn3)c(F)c2)c2c(N)nccn12] | (S)-4-(8-amino-3-(1-but-2-ynoylpiperidin-2-yl)imidazo[1,5-a]pyrazin-1-yl)-2-fluoro-N-(4-propylpyridin-2-yl)benzamide | 540.3 | 2.56 min |
| 68 | 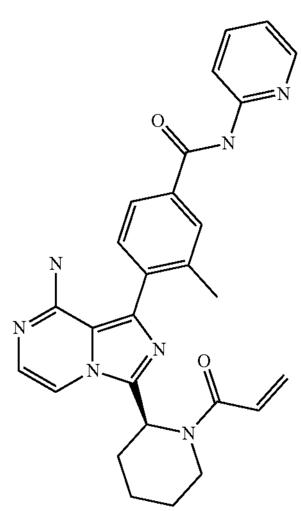 [SMILES: C=CC(=O)N1CCCC[C@H]1c1nc(-c2ccc(C(=O)Nc3ccccn3)cc2C)c2c(N)nccn12] | 4-(3-((S)-1-acryloylpiperidin-2-yl)-8-aminoimidazo[1,5-a]pyrazin-1-yl)-3-methyl-N-(pyridin-2-yl)benzamide | 482.2 | 1.98 min |

-continued

| Example | Structure | Name | (M + H)+ m/z | UPLC (C) Rt |
|---|---|---|---|---|
| 69 | 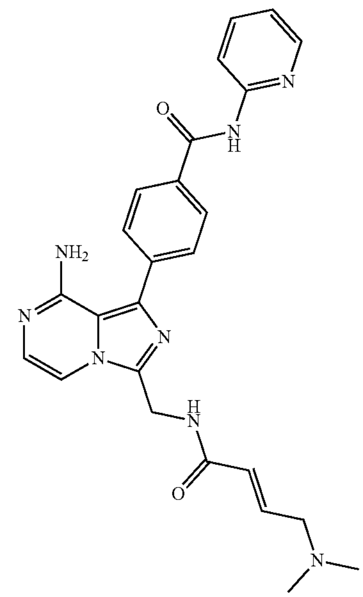 [SMILES: CN(C)C/C=C/C(=O)NCc1nc(-c2ccc(C(=O)Nc3ccccn3)cc2)c2c(N)nccn12] | (E)-4-(8-amino-3-((4-(dimethyl amino)but-2-enamido)methyl)imidazo[1,5-a]pyrazin-1-yl)-N-(pyridin-2-yl)benzamide | 471.2 | 1.16 min |
| 70 | 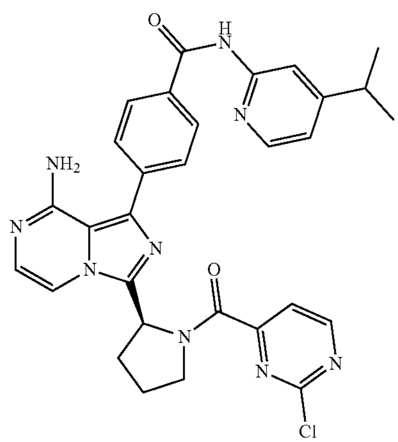 [SMILES: CC(C)c1ccnc(NC(=O)c2ccc(-c3nc([C@@H]4CCCN4C(=O)c4ccnc(Cl)n4)n4ccnc(N)c34)cc2)c1] | (S)-4-(8-amino-3-(1-(2-chloro pyrimidine-4-carbonyl)pyrrolidin-2-yl)imidazo[1,5-a]pyrazin-1-yl)-N-(4-isopropylpyridin-2-yl)benzamide | 582.2 | 1.89 min |
| 71 | 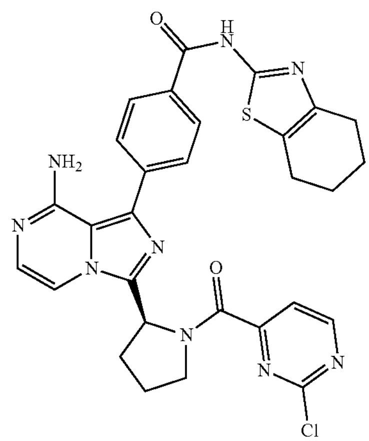 [SMILES: Nc1nccn2c([C@@H]3CCCN3C(=O)c3ccnc(Cl)n3)nc(-c3ccc(C(=O)Nc4nc5c(s4)CCCC5)cc3)c12] | (S)-4-(8-amino-3-(1-(2-chloro pyrimidine-4-carbonyl)pyrrolidin-2-yl)imidazo[1,5-a]pyrazin-1-yl)-N-(4,5,6,7-tetrahydro-benzo[d]thiazol-2-yl)benzamide | 600.2 | 2.49 min |

-continued

| Example | Structure | Name | (M + H)+ m/z | UPLC (C) Rt |
|---|---|---|---|---|
| 72 | 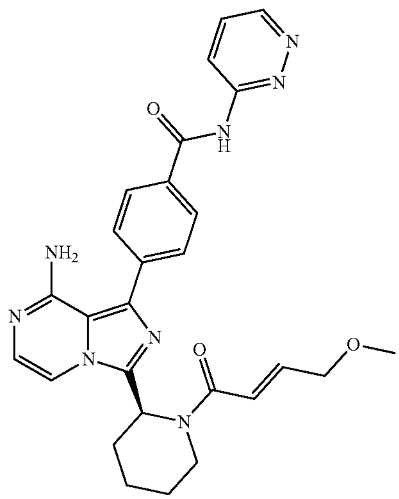 [SMILES: COC/C=C/C(=O)N1CCCC[C@H]1c1nc(-c2ccc(C(=O)Nc3cccnn3)cc2)c2c(N)nccn12] | (S,E)-4-(8-amino-3-(1-(4-methoxybut-2-enoyl)piperidin-2-yl)imidazo[1,5-a]pyrazin-1-yl)-N-(pyridazin-3-yl)benzamide | 513.3 | 1.84 min |
| 73 | 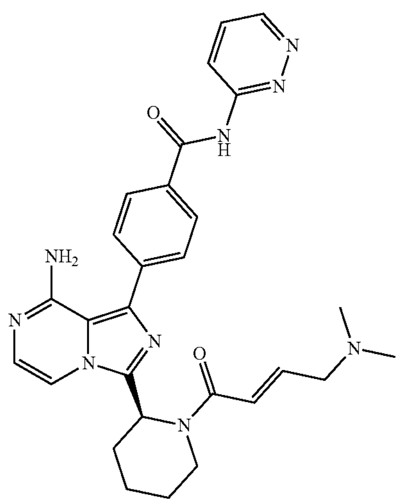 [SMILES: CN(C)C/C=C/C(=O)N1CCCC[C@H]1c1nc(-c2ccc(C(=O)Nc3cccnn3)cc2)c2c(N)nccn12] | (S,E)-4-(8-amino-3-(1-(4-(dimethylamino)but-2-enoyl)piperidin-2-yl)imidazo[1,5-a]pyrazin-1-yl)-N-(pyridazin-3-yl)benzamide | 526.4 | 1.26 min |
| 74 | 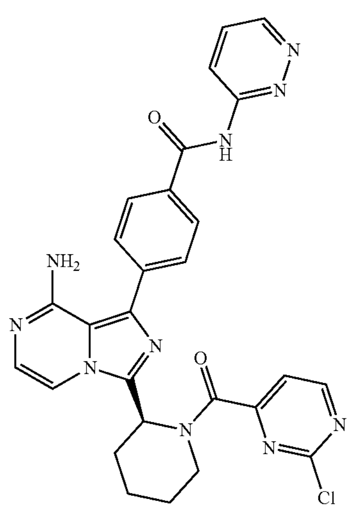 [SMILES: Nc1nccn2c([C@@H]3CCCCN3C(=O)c3ccnc(Cl)n3)nc(-c3ccc(C(=O)Nc4cccnn4)cc3)c12] | (S)-4-(8-amino-3-(1-(2-chloropyrimidine-4-carbonyl)piperidin-2-yl)imidazo[1,5-a]pyrazin-1-yl)-N-(pyridazin-3-yl)benzamide | 555.3 | 1.96 min |

| Example | Structure | Name | (M + H)+ m/z | UPLC (C) Rt |
|---|---|---|---|---|
| 75 | 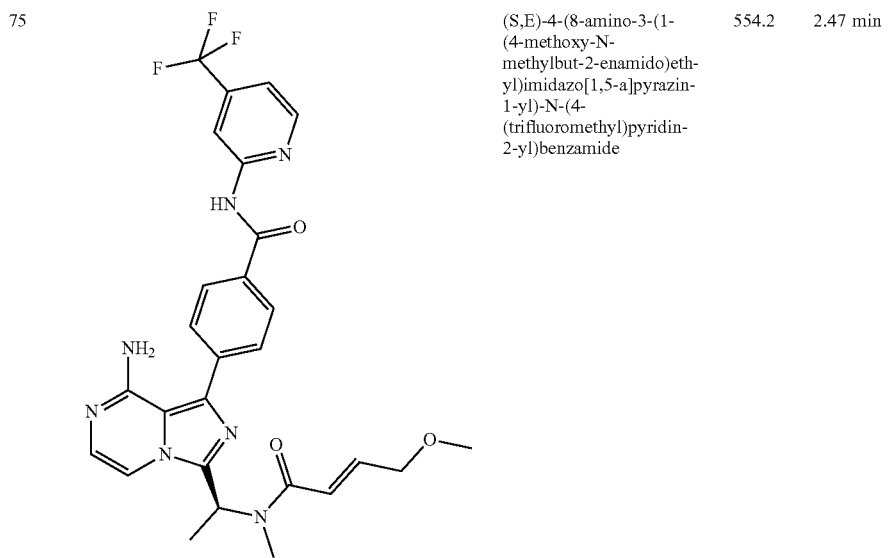 | (S,E)-4-(8-amino-3-(1-(4-methoxy-N-methylbut-2-enamido)ethyl)imidazo[1,5-a]pyrazin-1-yl)-N-(4-(trifluoromethyl)pyridin-2-yl)benzamide | 554.2 | 2.47 min |
| 76 | 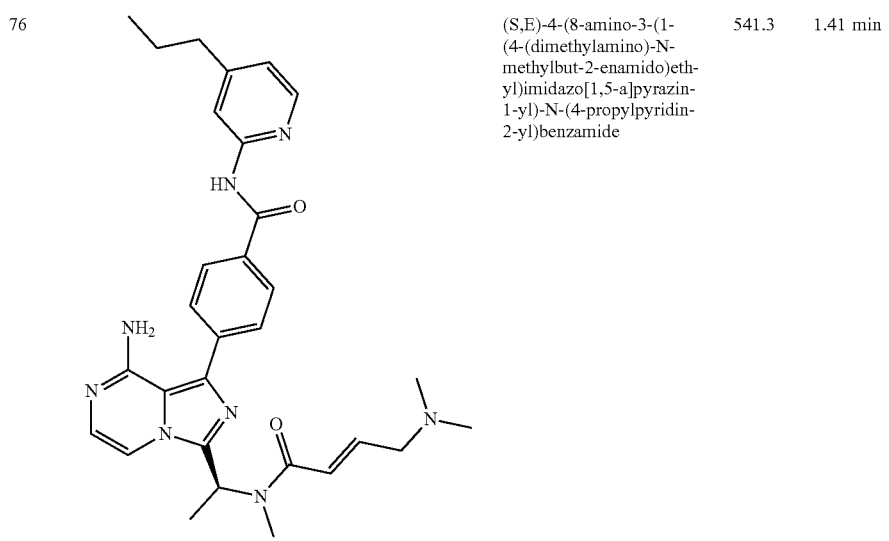 | (S,E)-4-(8-amino-3-(1-(4-(dimethylamino)-N-methylbut-2-enamido)ethyl)imidazo[1,5-a]pyrazin-1-yl)-N-(4-propylpyridin-2-yl)benzamide | 541.3 | 1.41 min |

| Example | Structure | Name | (M + H)+ m/z | UPLC (C) Rt |
|---|---|---|---|---|
| 77 | 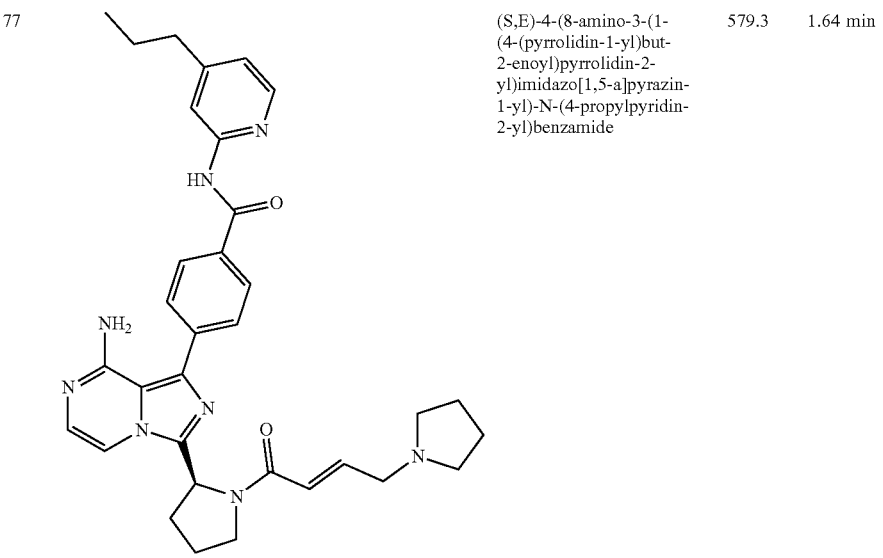 | (S,E)-4-(8-amino-3-(1-(4-(pyrrolidin-1-yl)but-2-enoyl)pyrrolidin-2-yl)imidazo[1,5-a]pyrazin-1-yl)-N-(4-propylpyridin-2-yl)benzamide | 579.3 | 1.64 min |
| 78 | 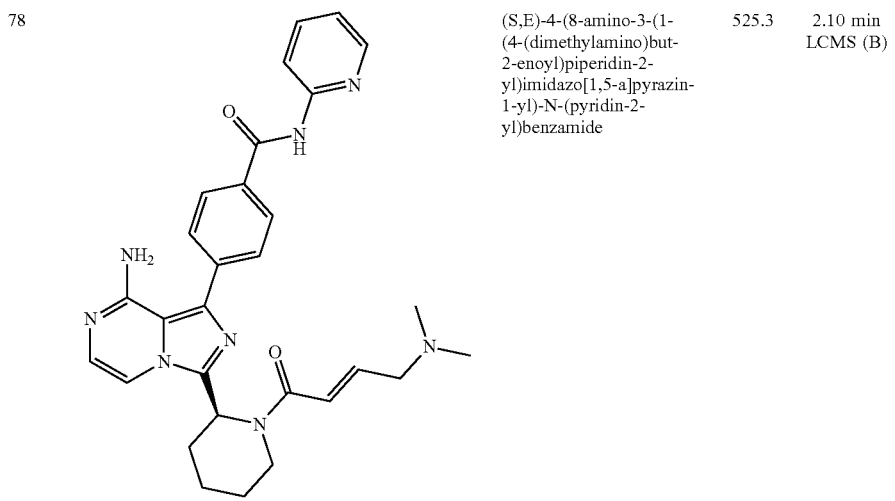 | (S,E)-4-(8-amino-3-(1-(4-(dimethylamino)but-2-enoyl)piperidin-2-yl)imidazo[1,5-a]pyrazin-1-yl)-N-(pyridin-2-yl)benzamide | 525.3 | 2.10 min LCMS (B) |

-continued
| Example | Structure | Name | (M + H)+ m/z | UPLC (C) Rt |
|---|---|---|---|---|
| 79 | 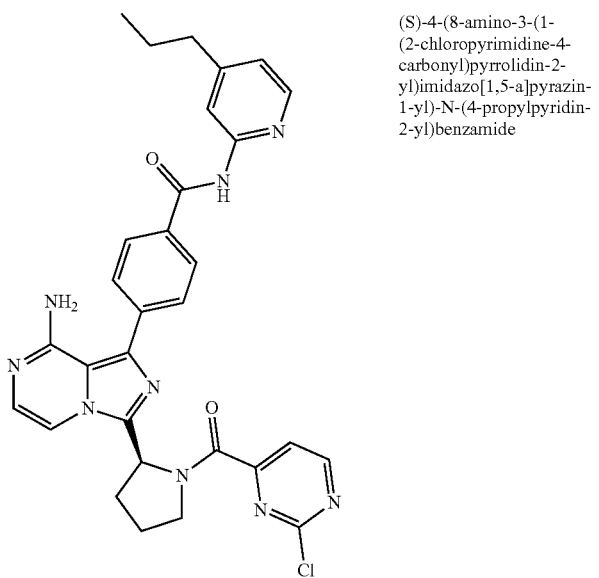 | (S)-4-(8-amino-3-(1-(2-chloropyrimidine-4-carbonyl)pyrrolidin-2-yl)imidazo[1,5-a]pyrazin-1-yl)-N-(4-propylpyridin-2-yl)benzamide | 582.3 | 1.95 min |
| 80 | 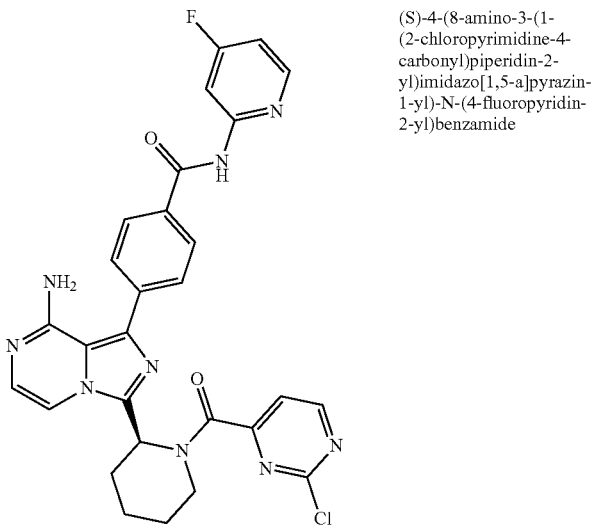 | (S)-4-(8-amino-3-(1-(2-chloropyrimidine-4-carbonyl)piperidin-2-yl)imidazo[1,5-a]pyrazin-1-yl)-N-(4-fluoropyridin-2-yl)benzamide | 572.3 | 2.45 min |

-continued

| Example | Structure | Name | (M + H)+ m/z | UPLC (C) Rt |
|---|---|---|---|---|
| 81 | 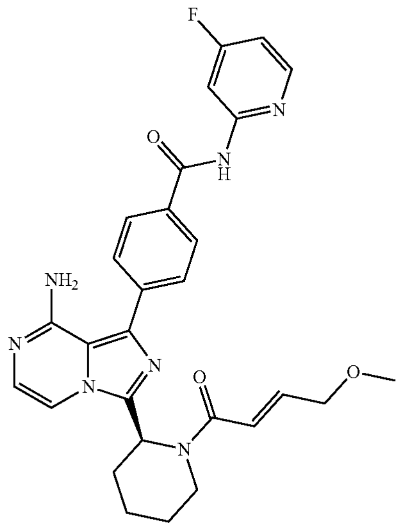 [SMILES: COC/C=C/C(=O)N1CCCC[C@H]1c1nc(-c2ccc(C(=O)Nc3cc(F)ccn3)cc2)c2c(N)nccn12] | (S,E)-4-(8-amino-3-(1-(4-methoxybut-2-enoyl)piperidin-2-yl)imidazo[1,5-a]pyrazin-1-yl)-N-(4-fluoropyridin-2-yl)benzamide | 530.3 | 2.38 min |
| 82 | 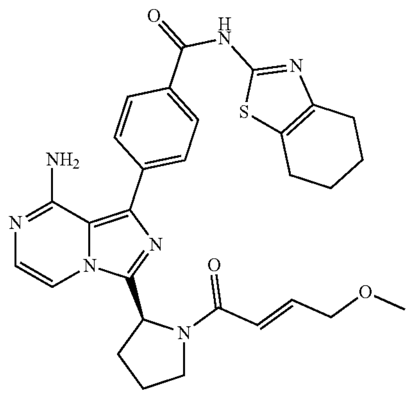 [SMILES: COC/C=C/C(=O)N1CCC[C@H]1c1nc(-c2ccc(C(=O)Nc3nc4c(s3)CCCC4)cc2)c2c(N)nccn12] | (S,E)-4-(8-amino-3-(1-(4-methoxybut-2-enoyl)pyrrolidin-2-yl)imidazo[1,5-a]pyrazin-1-yl)-N-(4,5,6,7-tetrahydrobenzo[d]thiazol-2-yl)benzamide | 558.3 | 2.33 min |
| 83 | 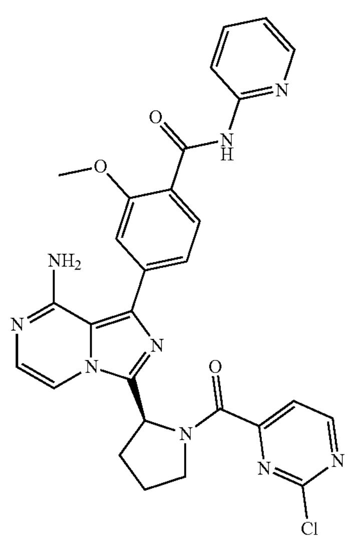 [SMILES: COc1cc(-c2nc([C@@H]3CCCN3C(=O)c3ccnc(Cl)n3)n3ccnc(N)c23)ccc1C(=O)Nc1ccccn1] | (S)-4-(8-amino-3-(1-(2-chloropyrimidine-4-carbonyl)pyrrolidin-2-yl)imidazo[1,5-a]pyrazin-1-yl)-2-methoxy-N-(pyridin-2-yl)benzamide | 570.3 | 2.01 min |

-continued

| Example | Structure | Name | (M + H)+ m/z | UPLC (C) Rt |
|---|---|---|---|---|
| 84 | 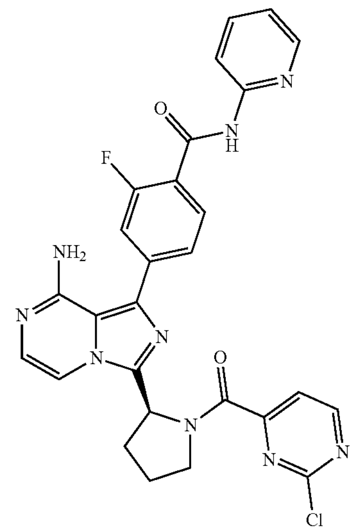 [SMILES: Nc1nccn2c([C@@H]3CCCN3C(=O)c3ccnc(Cl)n3)nc(-c3ccc(C(=O)Nc4ccccn4)c(F)c3)c12] | (S)-4-(8-amino-3-(1-(2-chloropyrimidine-4-carbonyl)pyrrolidin-2-yl)imidazo[1,5-a]pyrazin-1-yl)-2-fluoro-N-(pyridin-2-yl)benzamide | 558.2 | 1.95 min |
| 85 | 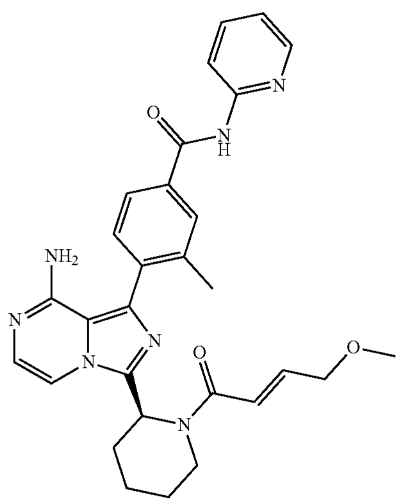 [SMILES: COC/C=C/C(=O)N1CCCC[C@H]1c1nc(-c2ccc(C(=O)Nc3ccccn3)cc2C)c2c(N)nccn12] | 4-(8-amino-3-((S)-1-((E)-4-methoxybut-2-enoyl)piperidin-2-yl)imidazo[1,5-a]pyrazin-1-yl)-3-methyl-N-(pyridin-2-yl)benzamide | 526.3 | 2.12 min |
| 86 | 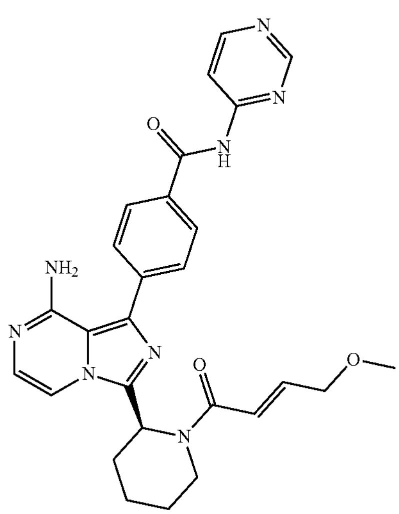 [SMILES: COC/C=C/C(=O)N1CCCC[C@H]1c1nc(-c2ccc(C(=O)Nc3ccncn3)cc2)c2c(N)nccn12] | (S,E)-4-(8-amino-3-(1-(4-methoxybut-2-enoyl)piperidin-2-yl)imidazo[1,5-a]pyrazin-1-yl)-N-(pyrimidin-4-yl)benzamide | 513.3 | 1.83 min |

-continued

| Example | Structure | Name | (M + H)+ m/z | UPLC (C) Rt |
|---|---|---|---|---|
| 87 | 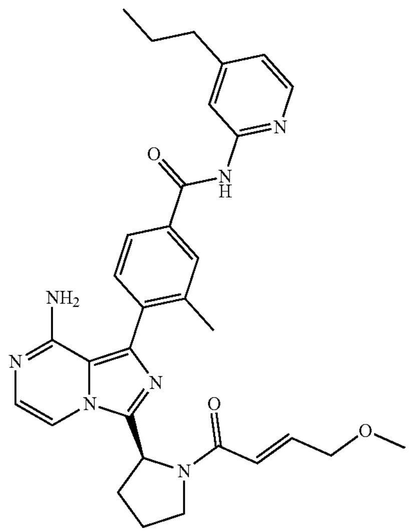 [SMILES: CCCc1ccnc(NC(=O)c2ccc(-c3nc([C@@H]4CCCN4C(=O)/C=C/COC)n4ccnc(N)c34)c(C)c2)c1] | 4-(8-amino-3-((S)-1-((E)-4-methoxybut-2-enoyl)pyrrolidin-2-yl)imidazo[1,5-a]pyrazin-1-yl)-3-methyl-N-(4-propylpyridin-2-yl)benzamide | 554.4 | 1.86 min |
| 88 | 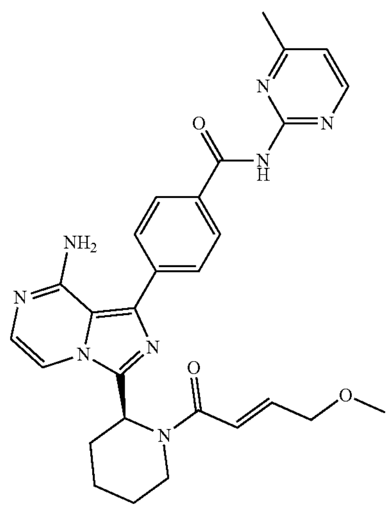 [SMILES: COC/C=C/C(=O)N1CCCC[C@H]1c1nc(-c2ccc(C(=O)Nc3nccc(C)n3)cc2)c2c(N)nccn12] | (S,E)-4-(8-amino-3-(1-(4-methoxybut-2-enoyl)piperidin-2-yl)imidazo[1,5-a]pyrazin-1-yl)-N-(4-methylpyrimidin-2-yl)benzamide | 527.3 | 1.88 min |
| 89 | 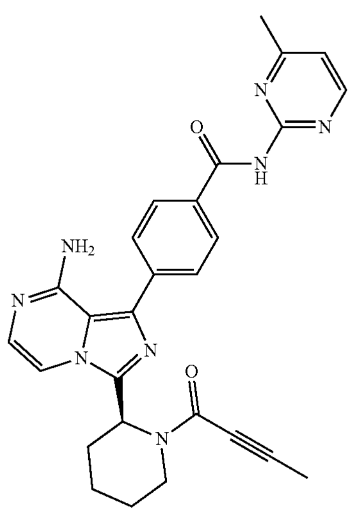 [SMILES: CC#CC(=O)N1CCCC[C@H]1c1nc(-c2ccc(C(=O)Nc3nccc(C)n3)cc2)c2c(N)nccn12] | (S)-4-(8-amino-3-(1-but-2-ynoylpiperidin-2-yl)imidazo[1,5-a]pyrazin-1-yl)-N-(4-methylpyrimidin-2-yl)benzamide | 495.3 | 1.97 min |

-continued

| Example | Structure | Name | (M + H)+ m/z | UPLC (C) Rt |
|---|---|---|---|---|
| 90 | 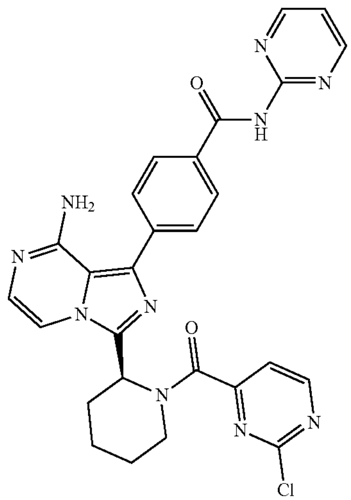 [SMILES: Nc1nccn2c([C@@H]3CCCCN3C(=O)c3ccnc(Cl)n3)nc(-c3ccc(C(=O)Nc4ncccn4)cc3)c12] | (S)-4-(8-amino-3-(1-(2-chloropyrimidine-4-carbonyl)piperidin-2-yl)imidazo[1,5-a]pyrazin-1-yl)-N-(pyrimidin-2-yl)benzamide | 555.3 | 1.91 min |
| 91 | 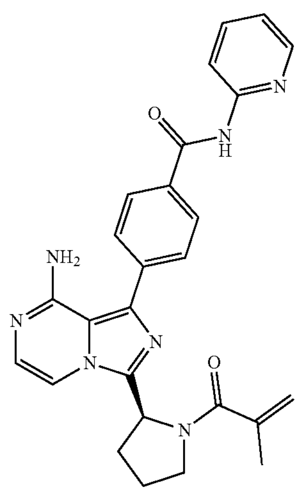 [SMILES: C=C(C)C(=O)N1CCC[C@H]1c1nc(-c2ccc(C(=O)Nc3ccccn3)cc2)c2c(N)nccn12] | (S)-4-(8-amino-3-(1-methacryloylpyrrolidin-2-yl)imidazo[1,5-a]pyrazin-1-yl)-N-(pyridin-2-yl)benzamide | 468.4 | 1.61 min |
| 92 | 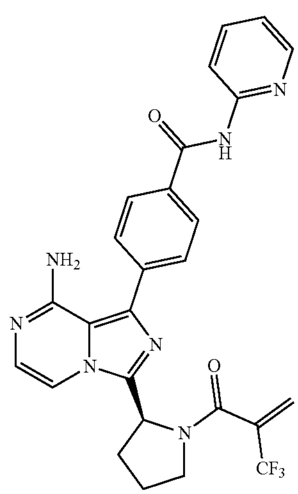 [SMILES: C=C(C(=O)N1CCC[C@H]1c1nc(-c2ccc(C(=O)Nc3ccccn3)cc2)c2c(N)nccn12)C(F)(F)F] | (S)-4-(8-amino-3-(1-(2-(trifluoromethyl)acryloyl)pyrrolidin-2-yl)imidazo[1,5-a]pyrazin-1-yl)-N-(pyridin-2-yl)benzamide | 522.3 | 1.99 min |

-continued

| Example | Structure | Name | (M + H)+ m/z | UPLC (C) Rt |
|---|---|---|---|---|
| 93 | 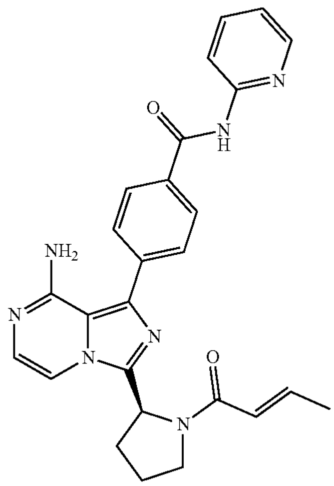 [SMILES: C/C=C/C(=O)N1CCC[C@H]1c1nc(-c2ccc(C(=O)Nc3ccccn3)cc2)c2c(N)nccn12] | (S,E)-4-(8-amino-3-(1-but-2-enoylpyrrolidin-2-yl)imidazo[1,5-a]pyrazin-1-yl)-N-(pyridin-2-yl)benzamide | 468.4 | 1.59 min |
| 94 | 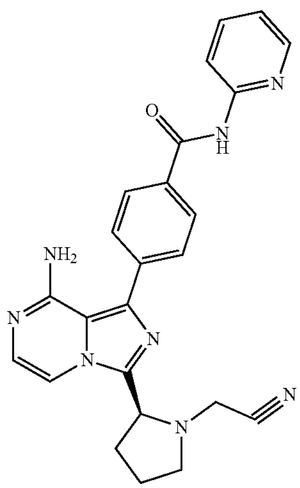 [SMILES: N#CCN1CCC[C@H]1c1nc(-c2ccc(C(=O)Nc3ccccn3)cc2)c2c(N)nccn12] | (S)-4-(8-amino-3-(1-(cyanomethyl)pyrrolidin-2-yl)imidazo[1,5-a]pyrazin-1-yl)-N-(pyridin-2-yl)benzamide | 439.3 | 1.55 min |
| 95 | 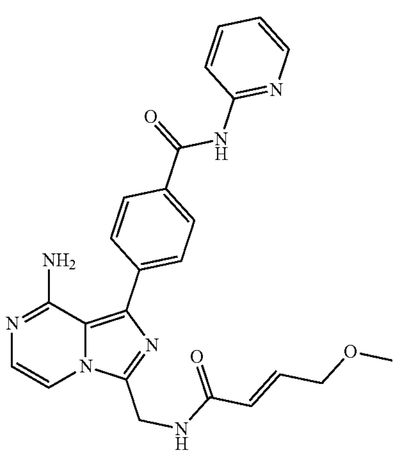 [SMILES: COC/C=C/C(=O)NCc1nc(-c2ccc(C(=O)Nc3ccccn3)cc2)c2c(N)nccn12] | (E)-4-(8-amino-3-((4-methoxybut-2-enamido)methyl)imidazo[1,5-a]pyrazin-1-yl)-N-(pyridin-2-yl)benzamide | 458.2 | 1.35 min |

-continued
| Example | Structure | Name | (M + H)+ m/z | UPLC (C) Rt |
|---|---|---|---|---|
| 96 | 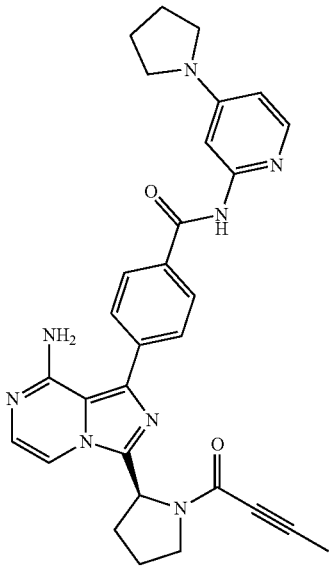 [SMILES: CC#CC(=O)N1CCC[C@H]1c1nc(-c2ccc(C(=O)Nc3cc(N4CCCC4)ccn3)cc2)c2c(N)nccn12] | (S)-4-(8-amino-3-(1-but-2-ynoylpyrrolidin-2-yl)imidazo[1,5-a]pyrazin-1-yl)-N-(4-(pyrrolidin-1-yl)pyridin-2-yl)benzamide | 535.3 | 2.27 min LCMS (B) |
| 97 | 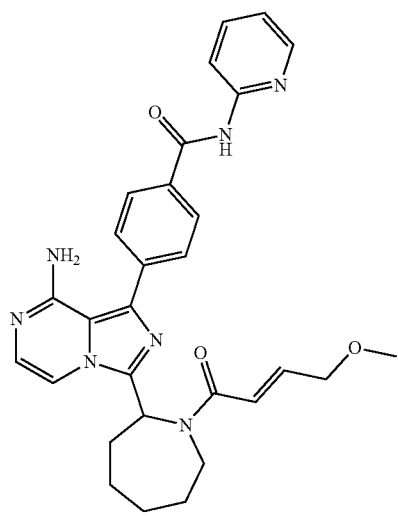 [SMILES: COC/C=C/C(=O)N1CCCCCC1c1nc(-c2ccc(C(=O)Nc3ccccn3)cc2)c2c(N)nccn12] | (E)-4-(8-amino-3-(1-(4-methoxybut-2-enoyl)azepan-2-yl)imidazo[1,5-a]pyrazin-1-yl)-N-(pyridin-2-yl)benzamide | 526.3 | 1.97 min |

-continued

| Example | Structure | Name | (M + H)+ m/z | UPLC (C) Rt |
|---|---|---|---|---|
| 98 | 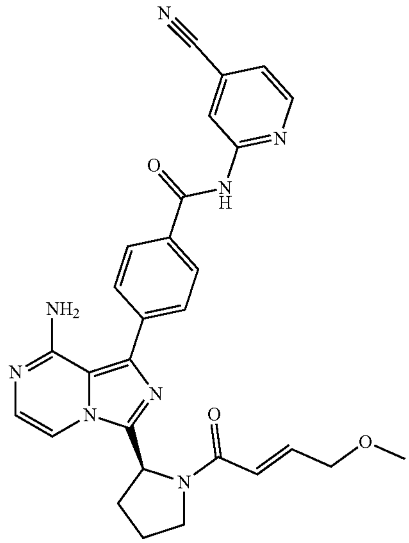 [SMILES: COC/C=C/C(=O)N1CCC[C@H]1c1nc(-c2ccc(C(=O)Nc3cc(C#N)ccn3)cc2)c2c(N)nccn12] | (S,E)-4-(8-amino-3-(1-(4-methoxybut-2-enoyl)pyrrolidin-2-yl)imidazo[1,5-a]pyrazin-1-yl)-N-(4-cyanopyridin-2-yl)benzamide | 523.3 | 2.12 min |
| 99 | 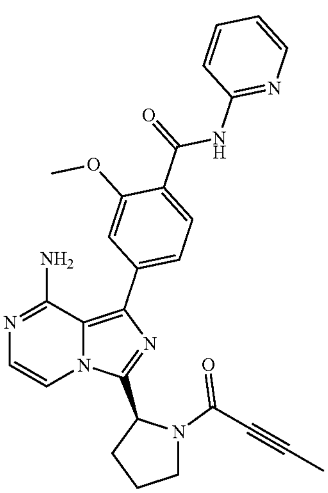 [SMILES: CC#CC(=O)N1CCC[C@H]1c1nc(-c2ccc(C(=O)Nc3ccccn3)c(OC)c2)c2c(N)nccn12] | (S)-4-(8-amino-3-(1-but-2-ynoylpyrrolidin-2-yl)imidazo[1,5-a]pyrazin-1-yl)-2-methoxy-N-(pyridin-2-yl)benzamide | 496.3 | 1.87 min |
| 100 | 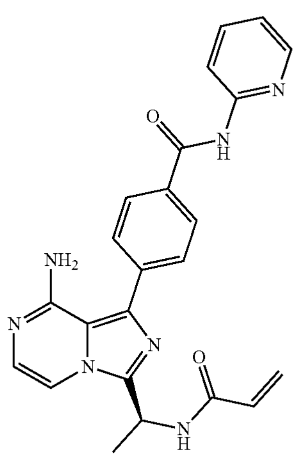 [SMILES: C=CC(=O)N[C@@H](C)c1nc(-c2ccc(C(=O)Nc3ccccn3)cc2)c2c(N)nccn12] | (S)-4-(3-(1-acrylamido-ethyl)-8-amino-imidazo[1,5-a]pyrazin-1-yl)-N-(pyridin-2-yl)benzamide | 428.3 | 1.15 min |

| Example | Structure | Name | (M + H)+ m/z | UPLC (C) Rt |
| --- | --- | --- | --- | --- |
| 101 | 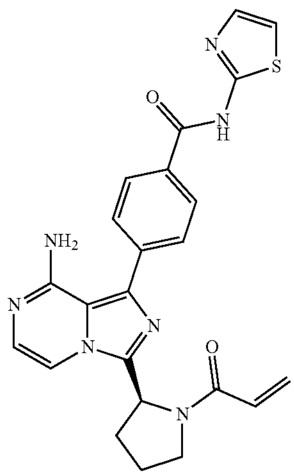 [SMILES: C=CC(=O)N1CCC[C@H]1c1nc(-c2ccc(C(=O)Nc3nccs3)cc2)c2c(N)nccn12] | (S)-4-(3-(1-acryloylpyrrolidin-2-yl)-8-amino-imidazo[1,5-a]pyrazin-1-yl)-N-(thiazol-2-yl)benzamide | 460.2 | 2.03 min |
| 102 | 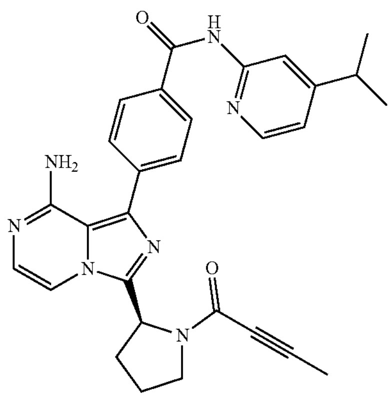 [SMILES: CC#CC(=O)N1CCC[C@H]1c1nc(-c2ccc(C(=O)Nc3cc(C(C)C)ccn3)cc2)c2c(N)nccn12] | (S)-4-(8-amino-3-(1-but-2-ynoylpyrrolidin-2-yl)imidazo[1,5-a]pyrazin-1-yl)-N-(4-isopropylpyridin-2-yl)benzamide | 507.8 | 1.82 min |
| 103 | 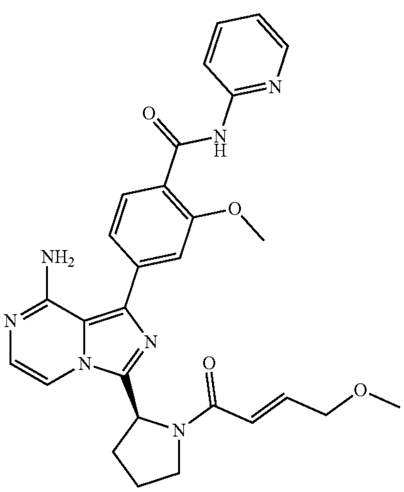 [SMILES: COC/C=C/C(=O)N1CCC[C@H]1c1nc(-c2ccc(C(=O)Nc3ccccn3)c(OC)c2)c2c(N)nccn12] | (S,E)-4-(8-amino-3-(1-(4-methoxybut-2-enoyl)pyrrolidin-2-yl)imidazo[1,5-a]pyrazin-1-yl)-2-methoxy-N-(pyridin-2-yl)benzamide | 528.3 | 1.84 min |

-continued

| Example | Structure | Name | (M + H)+ m/z | UPLC (C) Rt |
|---|---|---|---|---|
| 104 | 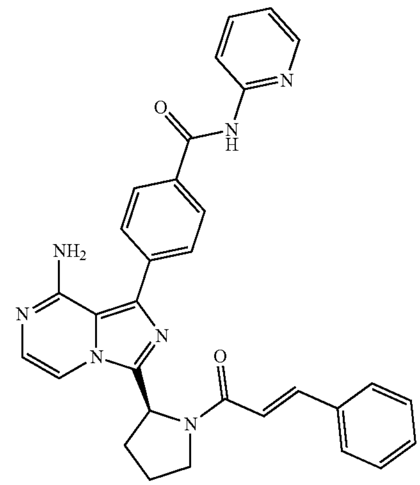 [SMILES: Nc1nccn2c([C@@H]3CCCN3C(=O)/C=C/c3ccccc3)nc(-c3ccc(C(=O)Nc4ccccn4)cc3)c12] | (S,E)-4-(8-amino-3-(1-cinnamoylpyrrolidin-2-yl)imidazo[1,5-a]pyrazin-1-yl)-N-(pyridin-2-yl)benzamide | 530.4 | 2.09 min |
| 105 | 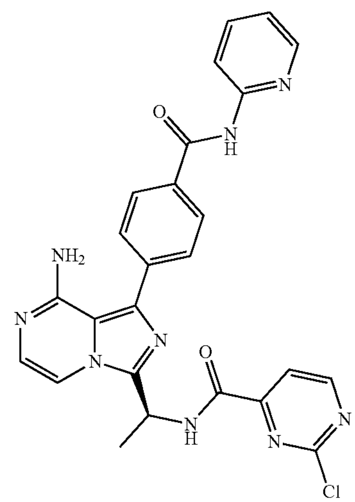 [SMILES: C[C@H](NC(=O)c1ccnc(Cl)n1)c1nc(-c2ccc(C(=O)Nc3ccccn3)cc2)c2c(N)nccn12] | (S)-N-(1-(8-amino-1-(4-(pyridin-2-ylcarbamoyl)phenyl)imidazo[1,5-a]pyrazin-3-yl)ethyl)-2-chloropyrimidine-4-carboxamide | 514.3 | 1.56 min |
| 106 | 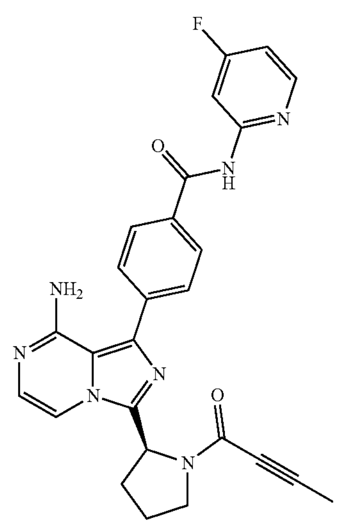 [SMILES: CC#CC(=O)N1CCC[C@H]1c1nc(-c2ccc(C(=O)Nc3cc(F)ccn3)cc2)c2c(N)nccn12] | (S)-4-(8-amino-3-(1-but-2-ynoylpyrrolidin-2-yl)imidazo[1,5-a]pyrazin-1-yl)-N-(4-fluoropyridin-2-yl)benzamide | 484.2 | 2.38 min |

| Example | Structure | Name | (M + H)+ m/z | UPLC (C) Rt |
|---|---|---|---|---|
| 107 | 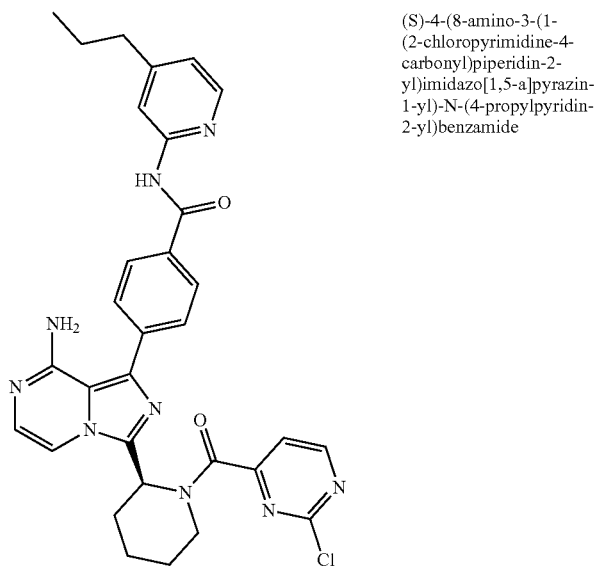 | (S)-4-(8-amino-3-(1-(2-chloropyrimidine-4-carbonyl)piperidin-2-yl)imidazo[1,5-a]pyrazin-1-yl)-N-(4-propylpyridin-2-yl)benzamide | 596.3 | 2.19 min |
| 108 | 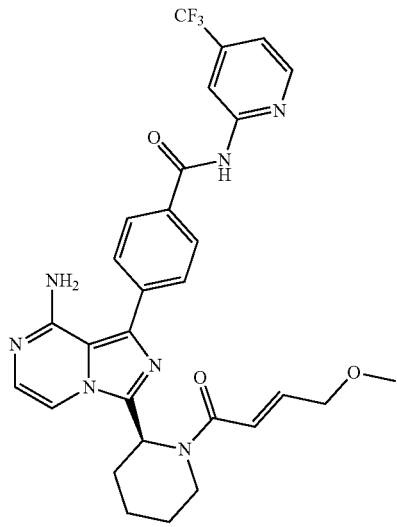 [SMILES: COC/C=C/C(=O)N1CCCC[C@H]1c1nc(-c2ccc(C(=O)Nc3cc(C(F)(F)F)ccn3)cc2)c2c(N)nccn12] | (S,E)-4-(8-amino-3-(1-(4-methoxybut-2-enoyl)piperidin-2-yl)imidazo[1,5-a]pyrazin-1-yl)-N-(4-(trifluoromethyl)pyridin-2-yl)benzamide | 580.3 | 1.03 min UPLC (B) |

| Example | Structure | Name | (M + H)+ m/z | UPLC (C) Rt |
|---|---|---|---|---|
| 109 | 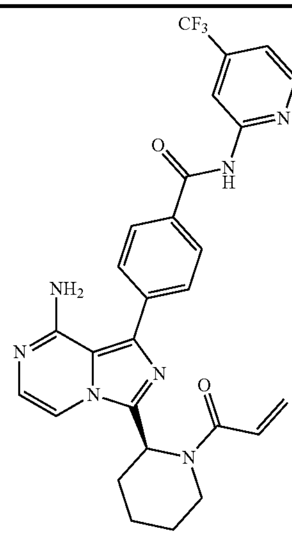 | (S)-4-(3-(1-acryloylpiperidin-2-yl)-8-aminoimidazo[1,5-a]pyrazin-1-yl)-N-(4-(trifluoromethyl)pyridin-2-yl)benzamide | 536.3 | 1.02 min UPLC (B) |
| 110 | 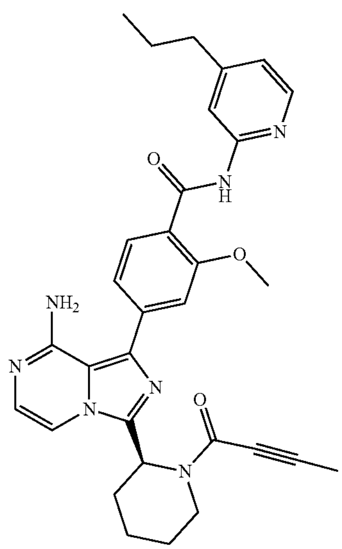 [SMILES: CC#CC(=O)N1CCCC[C@H]1c1nc(-c2ccc(C(=O)Nc3cc(CCC)ccn3)c(OC)c2)c2c(N)nccn12] | (S)-4-(8-amino-3-(1-but-2-ynoylpiperidin-2-yl)imidazo[1,5-a]pyrazin-1-yl)-2-methoxy-N-(4-propylpyridin-2-yl)benzamide | 552.4 | 2.57 min |
| 111 | 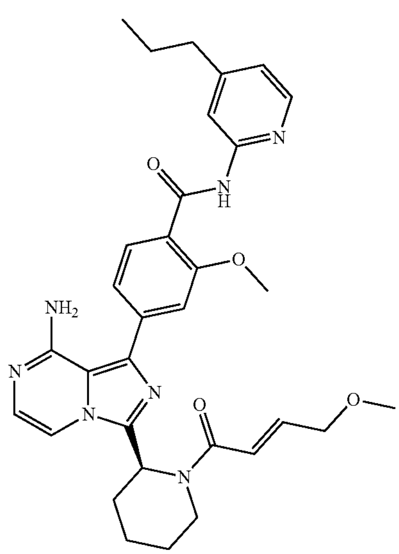 [SMILES: CCCc1ccnc(NC(=O)c2ccc(-c3nc([C@@H]4CCCCN4C(=O)/C=C/COC)n4ccnc(N)c34)cc2OC)c1] | (S,E)-4-(8-amino-3-(1-(4-methoxybut-2-enoyl)piperidin-2-yl)imidazo[1,5-a]pyrazin-1-yl)-2-methoxy-N-(4-propylpyridin-2-yl)benzamide | 584.4 | 2.49 min |

| Example | Structure | Name | (M + H)+ m/z | UPLC (C) Rt |
|---|---|---|---|---|
| 112 | 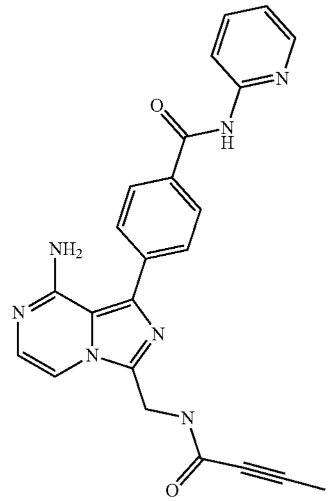 [SMILES: CC#CC(=O)NCc1nc(-c2ccc(C(=O)Nc3ccccn3)cc2)c2c(N)nccn12] | 4-(8-amino-3-(but-2-ynamidomethyl)imidazo[1,5-a]pyrazin-1-yl)-N-(pyridin-2-yl)benzamide | 426.2 | 1.35 min |
| 113 | 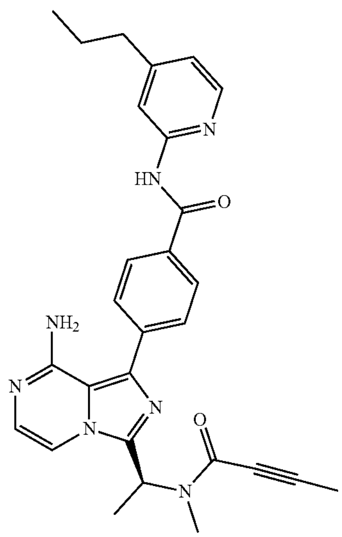 [SMILES: CC#CC(=O)N(C)[C@@H](C)c1nc(-c2ccc(C(=O)Nc3cc(CCC)ccn3)cc2)c2c(N)nccn12] | (S)-4-(8-amino-3-(1-(N-methylbut-2-ynamido)ethyl)imidazo[1,5-a]pyrazin-1-yl)-N-(4-propylpyridin-2-yl)benzamide | 496.3 | 1.94 min |
| 114 | 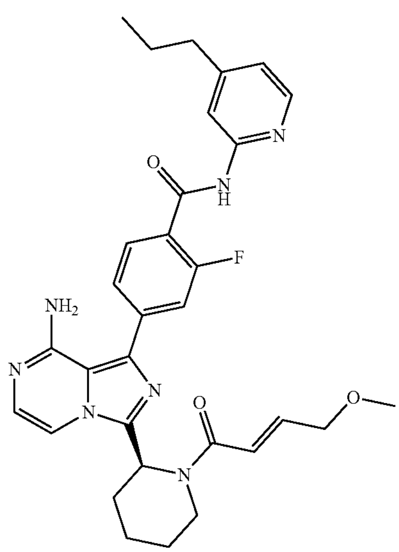 [SMILES: CCCc1ccnc(NC(=O)c2ccc(-c3nc([C@@H]4CCCCN4C(=O)/C=C/COC)n4ccnc(N)c34)cc2F)c1] | (S,E)-4-(8-amino-3-(1-(4-methoxybut-2-enoyl)piperidin-2-yl)imidazo[1,5-a]pyrazin-1-yl)-2-fluoro-N-(4-propylpyridin-2-yl)benzamide | 572.4 | 2.48 min |

-continued
| Example | Structure | Name | (M + H)+ m/z | UPLC (C) Rt |
|---|---|---|---|---|
| 115 | 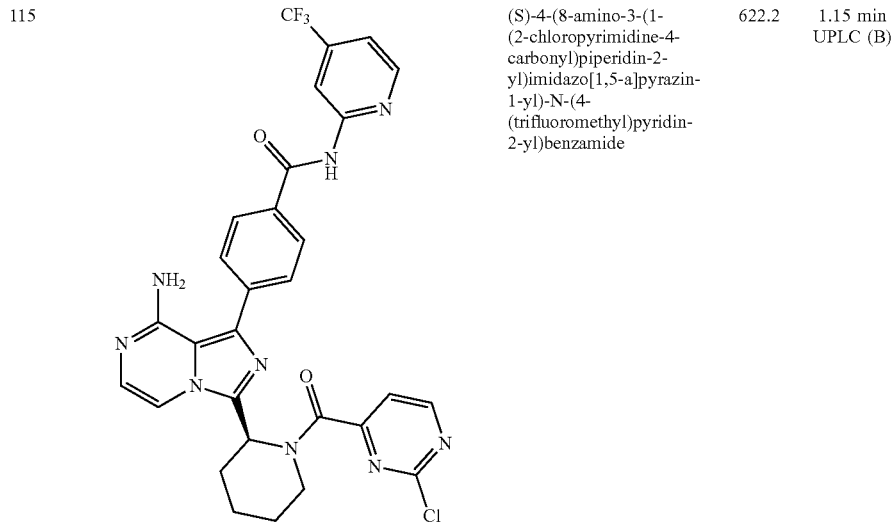 | (S)-4-(8-amino-3-(1-(2-chloropyrimidine-4-carbonyl)piperidin-2-yl)imidazo[1,5-a]pyrazin-1-yl)-N-(4-(trifluoromethyl)pyridin-2-yl)benzamide | 622.2 | 1.15 min UPLC (B) |
| 116 | 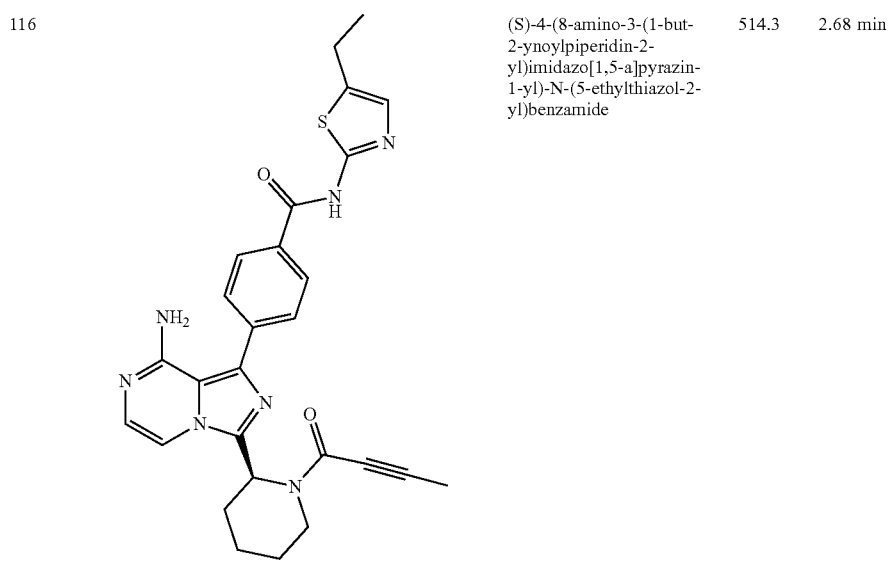 | (S)-4-(8-amino-3-(1-but-2-ynoylpiperidin-2-yl)imidazo[1,5-a]pyrazin-1-yl)-N-(5-ethylthiazol-2-yl)benzamide | 514.3 | 2.68 min |

-continued

| Example | Structure | Name | (M + H)+ m/z | UPLC (C) Rt |
|---|---|---|---|---|
| 117 | 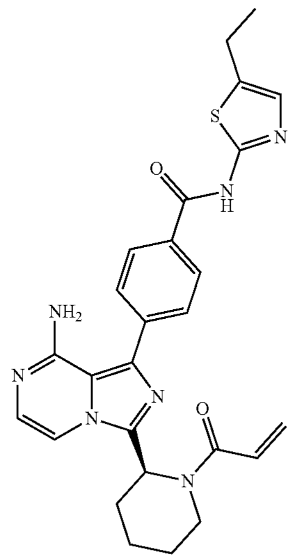 [SMILES: C=CC(=O)N1CCCC[C@H]1c1nc(-c2ccc(C(=O)Nc3ncc(CC)s3)cc2)c2c(N)nccn12] | (S)-4-(3-(1-acryloylpiperidin-2-yl)-8-aminoimidazo[1,5-a]pyrazin-1-yl)-N-(5-ethylthiazol-2-yl)benzamide | 502.3 | 2.53 min |
| 118 | 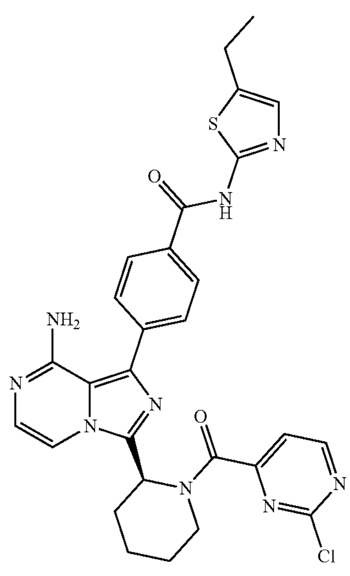 [SMILES: CCc1cnc(NC(=O)c2ccc(-c3nc([C@@H]4CCCCN4C(=O)c4ccnc(Cl)n4)n4ccnc(N)c34)cc2)s1] | (S)-4-(8-amino-3-(1-(2-chloropyrimidine-4-carbonyl)piperidin-2-yl)imidazo[1,5-a]pyrazin-1-yl)-N-(5-ethylthiazol-2-yl)benzamide | 588.3 | 2.71 min |

-continued
| Example | Structure | Name | (M + H)+ m/z | UPLC (C) Rt |
|---|---|---|---|---|
| 119 | 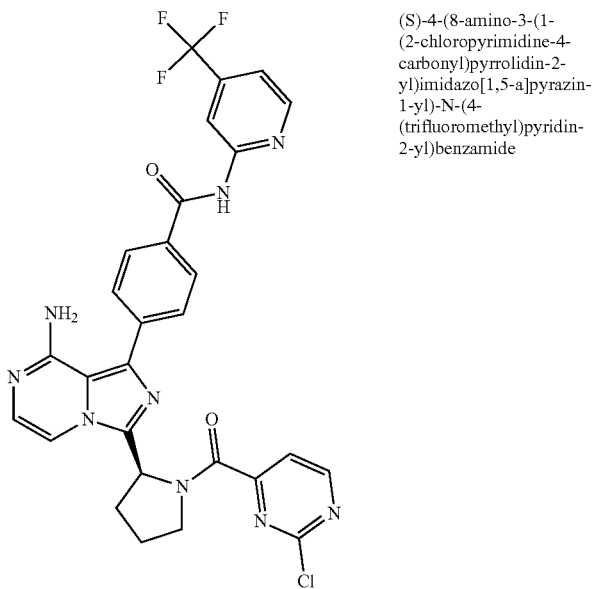 | (S)-4-(8-amino-3-(1-(2-chloropyrimidine-4-carbonyl)pyrrolidin-2-yl)imidazo[1,5-a]pyrazin-1-yl)-N-(4-(trifluoromethyl)pyridin-2-yl)benzamide | 608.2 | 2.68 min |
| 120 | 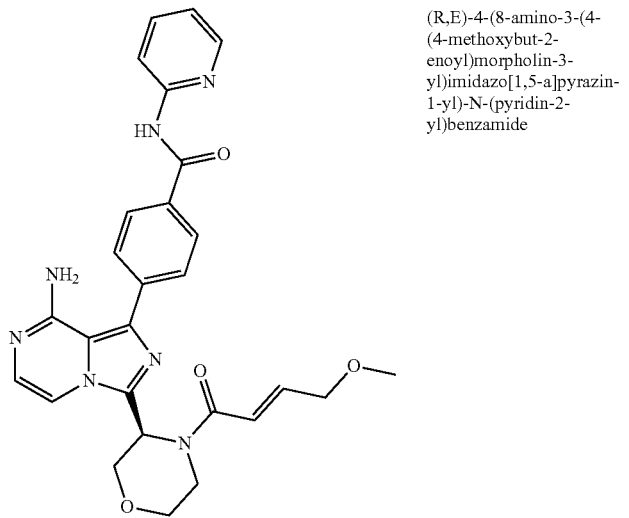 | (R,E)-4-(8-amino-3-(4-(4-methoxybut-2-enoyl)morpholin-3-yl)imidazo[1,5-a]pyrazin-1-yl)-N-(pyridin-2-yl)benzamide | 514.3 | 1.34 min |

| Example | Structure | Name | (M + H)+ m/z | UPLC (C) Rt |
|---|---|---|---|---|
| 121 | 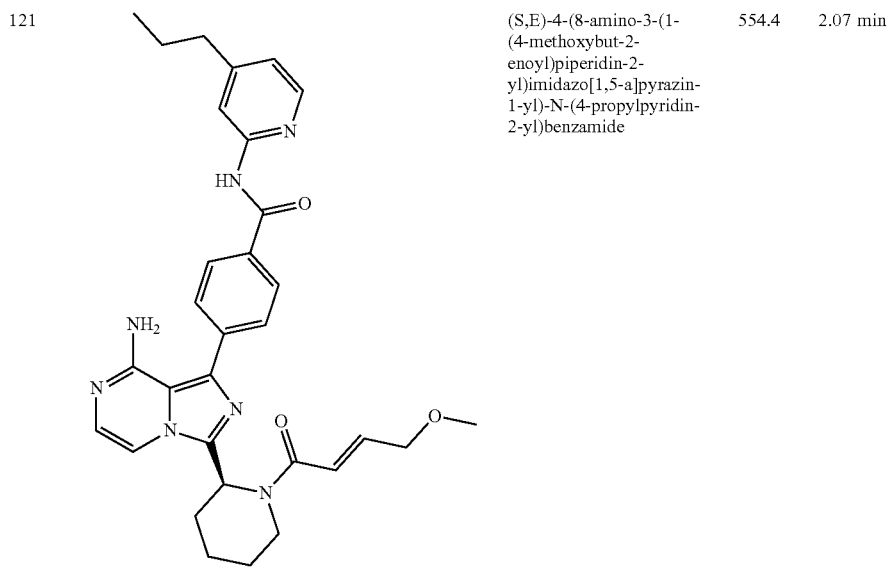 | (S,E)-4-(8-amino-3-(1-(4-methoxybut-2-enoyl)piperidin-2-yl)imidazo[1,5-a]pyrazin-1-yl)-N-(4-propylpyridin-2-yl)benzamide | 554.4 | 2.07 min |
| 122 | 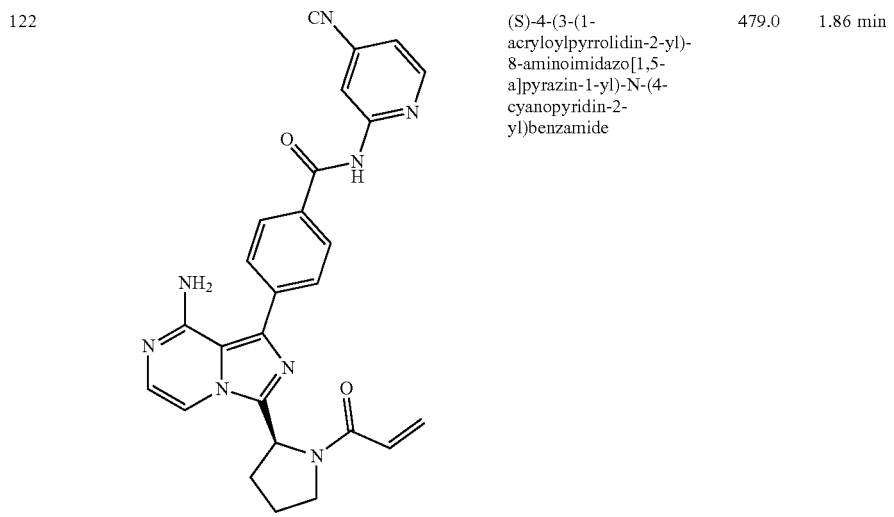 | (S)-4-(3-(1-acryloylpyrrolidin-2-yl)-8-aminoimidazo[1,5-a]pyrazin-1-yl)-N-(4-cyanopyridin-2-yl)benzamide | 479.0 | 1.86 min |

| Example | Structure | Name | (M + H)+ m/z | UPLC (C) Rt |
|---|---|---|---|---|
| 123 | 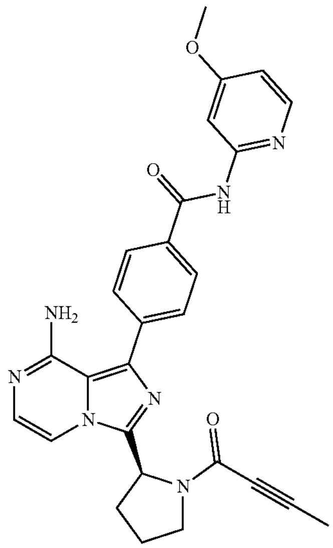 [SMILES: CC#CC(=O)N1CCC[C@H]1c1nc(-c2ccc(C(=O)Nc3cc(OC)ccn3)cc2)c2c(N)nccn12] | (S)-4-(8-amino-3-(1-but-2-ynoylpyrrolidin-2-yl)imidazo[1,5-a]pyrazin-1-yl)-N-(4-methoxypyridin-2-yl)benzamide | 496.3 | 1.50 min |
| 124 | 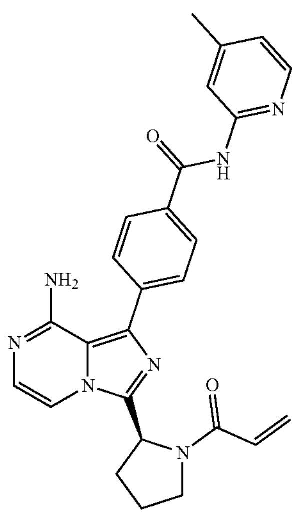 [SMILES: C=CC(=O)N1CCC[C@H]1c1nc(-c2ccc(C(=O)Nc3cc(C)ccn3)cc2)c2c(N)nccn12] | (S)-4-(3-(1-acryloylpyrrolidin-2-yl)-8-aminoimidazo[1,5-a]pyrazin-1-yl)-N-(4-methylpyridin-2-yl)benzamide | 468.1 | 1.37 min |
| 125 | 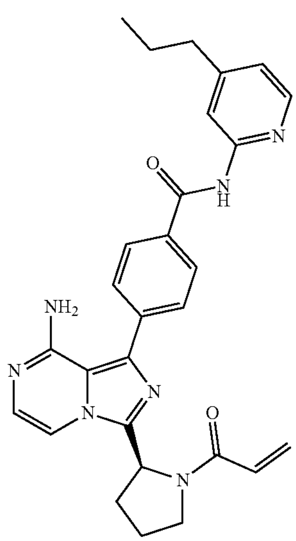 [SMILES: C=CC(=O)N1CCC[C@H]1c1nc(-c2ccc(C(=O)Nc3cc(CCC)ccn3)cc2)c2c(N)nccn12] | (S)-4-(3-(1-acryloylpyrrolidin-2-yl)-8-aminoimidazo[1,5-a]pyrazin-1-yl)-N-(4-propylpyridin-2-yl)benzamide | 496.1 | 1.76 min |

-continued

| Example | Structure | Name | (M + H)+ m/z | UPLC (C) Rt |
|---|---|---|---|---|
| 126 | 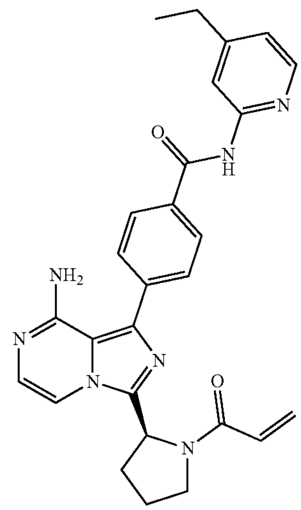 [SMILES: C=CC(=O)N1CCC[C@H]1c1nc(-c2ccc(C(=O)Nc3cc(CC)ccn3)cc2)c2c(N)nccn12] | (S)-4-(3-(1-acryloylpyrrolidin-2-yl)-8-aminoimidazo[1,5-a]pyrazin-1-yl)-N-(4-ethylpyridin-2-yl)benzamide | 482.1 | 1.53 min |
| 127 | 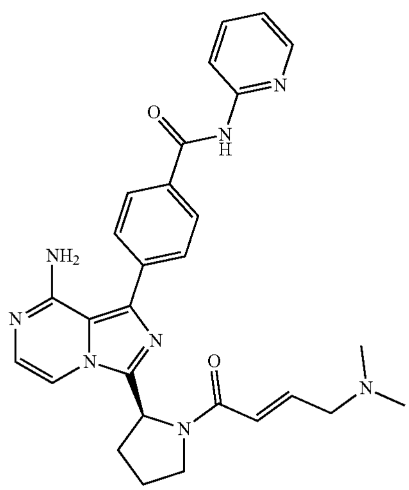 [SMILES: CN(C)C/C=C/C(=O)N1CCC[C@H]1c1nc(-c2ccc(C(=O)Nc3ccccn3)cc2)c2c(N)nccn12] | (S,E)-4-(8-amino-3-(1-(4-(dimethylamino)but-2-enoyl)pyrrolidin-2-yl)imidazo[1,5-a]pyrazin-1-yl)-N-(pyridin-2-yl)benzamide | 511.0 | 1.29 min |
| 128 | 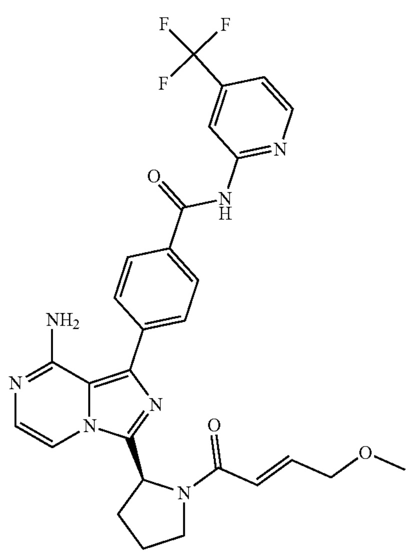 [SMILES: COC/C=C/C(=O)N1CCC[C@H]1c1nc(-c2ccc(C(=O)Nc3cc(C(F)(F)F)ccn3)cc2)c2c(N)nccn12] | (S,E)-4-(8-amino-3-(1-(4-methoxybut-2-enoyl)pyrrolidin-2-yl)imidazo[1,5-a]pyrazin-1-yl)-N-(4-(trifluoromethyl)pyridin-2-yl)benzamide | 566.3 | 2.73 min |

| Example | Structure | Name | (M + H)+ m/z | UPLC (C) Rt |
|---|---|---|---|---|
| 129 | 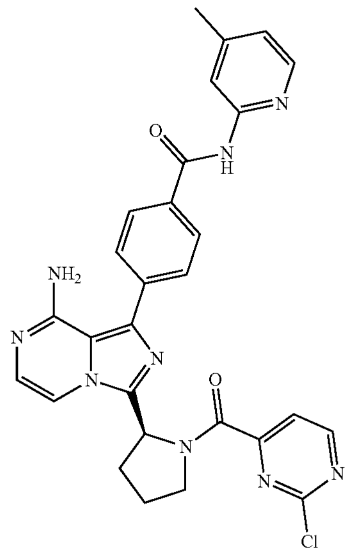 [SMILES: Cc1ccnc(NC(=O)c2ccc(-c3nc([C@@H]4CCCN4C(=O)c4ccnc(Cl)n4)n4ccnc(N)c34)cc2)c1] | (S)-4-(8-amino-3-(1-(2-chloropyrimidine-4-carbonyl)pyrrolidin-2-yl)imidazo[1,5-a]pyrazin-1-yl)-N-(4-methylpyridin-2-yl)benzamide | 554.2 | 1.38 min |
| 130 | 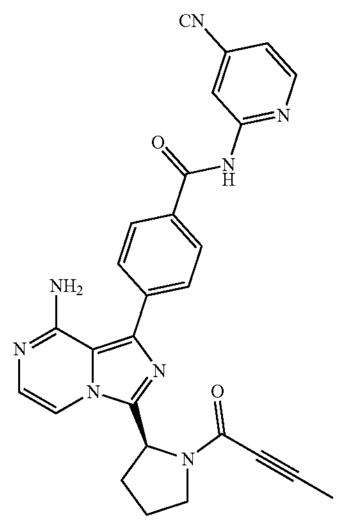 | (S)-4-(8-amino-3-(1-but-2-ynoylpyrrolidin-2-yl)imidazo[1,5-a]pyrazin-1-yl)-N-(4-cyanopyridin-2-yl)benzamide | 491.2 | 2.20 min |
| 131 | 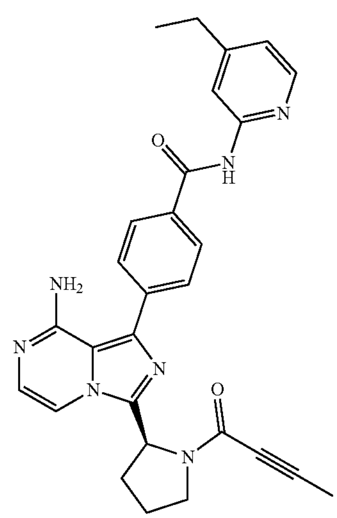 [SMILES: CC#CC(=O)N1CCC[C@H]1c1nc(-c2ccc(C(=O)Nc3cc(CC)ccn3)cc2)c2c(N)nccn12] | (S)-4-(8-amino-3-(1-but-2-ynoylpyrrolidin-2-yl)imidazo[1,5-a]pyrazin-1-yl)-N-(4-ethylpyridin-2-yl)benzamide | 494.3 | 1.65 min |

| Example | Structure | Name | (M + H)+ m/z | UPLC (C) Rt |
|---|---|---|---|---|
| 132 | 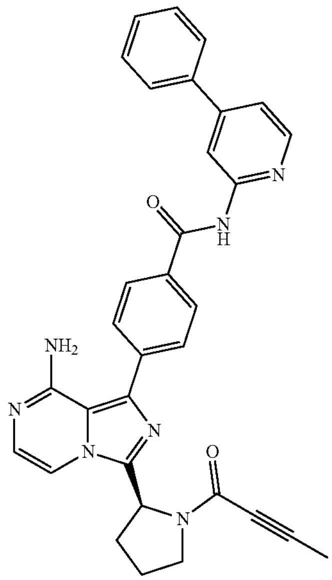 [SMILES: CC#CC(=O)N1CCC[C@H]1c1nc(-c2ccc(C(=O)Nc3cc(-c4ccccc4)ccn3)cc2)c2c(N)nccn12] | (S)-4-(8-amino-3-(1-but-2-ynoylpyrrolidin-2-yl)imidazo[1,5-a]pyrazin-1-yl)-N-(4-phenylpyridin-2-yl)benzamide | 542.3 | 2.57 min |
| 133 | 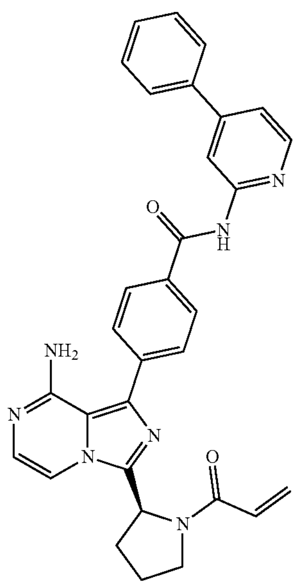 [SMILES: C=CC(=O)N1CCC[C@H]1c1nc(-c2ccc(C(=O)Nc3cc(-c4ccccc4)ccn3)cc2)c2c(N)nccn12] | (S)-4-(3-(1-acryloyl-pyrrolidin-2-yl)-8-aminoimidazo[1,5-a]pyrazin-1-yl)-N-(4-phenylpyridin-2-yl)benzamide | 530.3 | 2.38 min |

Example 134

Assay Methods

Btk Enzyme Activity

Btk enzyme activity is measured using the IMAP (immobilized metal ion affinity-based fluorescence polarization) assay as outlined below.

Btk enzyme (His-Btk (Millipore catalog #14-552), is diluted to 0.4 U/mL in KR buffer (10 mM Tris-HCl, 10 mM MgCl$_2$, 0.01% Tween-20, 0.05% NaN$_3$, 1 mM DTT, 2 mM MnCl$_2$, pH 7.2).

Serial dilution log 10 from 2 mM to 63.2 nM of test compounds are made in 100% DMSO. The dilutions in DMSO are then diluted 50-fold in KR-buffer. Final compound concentration range in the assay from 10 µM to 0.316 nM.

5 µL/well of test compound in KR buffer (final DMSO concentration in the assay is 1%) is mixed with 5 µl/well of 0.4 U/mL Btk enzyme (final concentration in the assay is 0.1 U/mL). Test compounds and Btk enzyme are pre-incubated 60 minutes at room temperature, before adding 5 µL/well of 200 nM Fluorescin labeled substrate peptide (Blk/Lyntide substrate, e.g. #R7188/#R7233, Molecular Devices) in KR-buffer. Final peptide substrate concentration in assay is 50 nM. The kinase assay is started by adding 5 µL/well of 20 µM ATP in KR-buffer (final ATP concentration is 5 µM ATP, Km ATP in Btk IMAP assay). Following incubation for 2 h at room temperature the enzyme reaction is stopped by adding 40 µL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $EC_{50}$ values are determined by curve fitting of the experimental results using Activity Base.

All examples have an EC50 of 10 µM or lower.

TABLE 1

EC50 Btk activity values

| EC50 | Example |
|---|---|
| ≥1 µM | 91, |
| ≥100 nM | 52, 53, 54, 55, 68, 72, 74, 85, 86, 87, 88, 90, 92, 93, |
| <1 µM | 94, 104 |
| ≥10 nM | 2, 4, 5, 7, 11, 24, 40, 41, 50, 51, 56, 57, 58, 59, 60, |
| <100 nM | 69, 70, 71, 73, 80, 81, 82, 83, 84, 89, 95, 96, 97, 98, 99, 103, 105, 106, 112, 113, 114, 119 |
| <10 nM | 1, 3, 6, 8, 9, 10, 12, 13, 14, 15, 16, 17, 18, 19, 20, 21, 22, 23, 25, 26, 27, 28, 29, 30, 31, 32, 33, 34, 35, 36, 37, 38, 39, 42, 43, 44, 45, 46, 47, 48, 49, 61, 62, 63, 64, 65, 66, 67, 75, 76, 77, 78, 79, 100, 101, 102, 107, 108, 109, 110, 111, 115, 116, 117, 118, 120, 121, 122, 123, 124, 125, 126, 127, 128, 129, 130, 131, 132, 133 |

Lck Enzyme Activity

Lck enzyme activity is measured using the IMAP (immobilized metal ion affinity-based fluorescence polarization) assay as outlined below.

Lck enzyme (Millipore catalog #14-442), is diluted to 0.4 U/mL in KR buffer (10 mM Tris-HCl, 10 mM MgCl2, 0.01% Tween-20, 0.05% NaN$_3$, 1 mM DTT, 2 mM MnCl$_2$, pH 7.2).

Serial dilution log 10 from 2 mM to 63.2 nM of test compounds are made in 100% DMSO. The dilutions in DMSO are then diluted 50-fold in KR-buffer of which 5 µl is used in the assay, leading to a final compound concentration range in the assay from 10 µM to 0.316 nM.

5 µL/well of test compound in KR buffer (final DMSO concentration in the assay is 1%) is mixed with 5 µl/well of 0.4 U/mL Lck enzyme (final concentration in the assay is 0.1 U/mL). Test compounds and Lck enzyme are pre-incubated 60 minutes at room temperature, before adding 5 µL/well of 400 nM Fluorescin labeled substrate peptide (p34cdc2 substrate peptide, e.g. #R7157/#R7172, Molecular Devices) in KR-buffer. Final peptide substrate concentration in assay is 100 nM. The kinase assay is started by adding 5 µL/well of 24 µM ATP in KR-buffer (final ATP concentration is 6 µM ATP, Km ATP in Lck IMAP assay). Following incubation for 2 h at room temperature the enzyme reaction is stopped by adding 40 µL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $EC_{50}$ values are determined by curve fitting of the experimental results using Activity Base.

TABLE 2

EC50 Lck activity values

| EC50 | Example |
|---|---|
| ≥1 µM | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 63, 65, 66, 67, 68, 69, 70, 71, 72, 73, 74, 75, 77, 78, 79, 80, 81, 82, 83, 84, 85, 86, 87, 88, 89, 90, 91, 92, 93, 94, 95, 96, 97, 98, 99, 100, 101, 102, 103, 105, 106, 107, 108, 109, 110, 111, 112, 113, 114, 115, 116, 117, 118, 119, 120, 121, 123, 127, 128, 129, 130, 131 |
| ≥100 nM <1 µM | 60, 62, 64, 76, 104, 122, 124, 125, 126, 132, 133 |

Src Enzyme Activity

Src enzyme activity is measured using the IMAP (immobilized metal ion affinity-based fluorescence polarization) assay as outlined below.

Src enzyme (Millipore catalog #14-326), is diluted to 0.8 U/mL in KR buffer (10 mM Tris-HCl, 10 mM MgCl$_2$, 0.01% Tween-20, 0.05% NaN$_3$, 1 mM DTT, 2 mM MnCl$_2$, pH 7.2).

Serial dilution log 10 from 2 mM to 63.2 nM of test compounds are made in 100% DMSO. The dilutions in DMSO are then diluted 50-fold in KR-buffer of which 5 µl is used in the assay, leading to a final compound concentration range in the assay from 10 µM to 0.316 nM.

5 µL/well of test compound in KR buffer (final DMSO concentration in the assay is 1%) is mixed with 5 µl/well of 0.8 U/mL Src enzyme (final concentration in the assay is 0.2 U/mL). Test compounds and Src enzyme are pre-incubated 60 minutes at room temperature, before adding 5 µL/well of 400 nM Fluorescin labeled substrate peptide (p34cdc2 substrate peptide, e.g. #R7157/#R7172, Molecular Devices) in KR-buffer. Final peptide substrate concentration in assay is 100 nM. The kinase assay is started by adding 5 µL/well of 16 µM ATP in KR-buffer (final ATP concentration is 4 µM ATP, Km ATP in Src IMAP assay). Following incubation for 2 h at room temperature the enzyme reaction is stopped by adding 40 µL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $EC_{50}$ values are determined by curve fitting of the experimental results using Activity Base.

TABLE 3

EC50 Src activity values

| EC50 | Example |
|---|---|
| ≥1 µM | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133 |

FynT Enzyme Activity

FynT enzyme activity is measured using the IMAP (immobilized metal ion affinity-based fluorescence polarization) assay as outlined below.

FynT enzyme (Biomol catalog #SE-287), is diluted to 0.5 µg/mL in KR buffer (10 mM Tris-HCl, 10 mM $MgCl_2$, 0.01% Tween-20, 0.05% $NaN_3$, 1 mM DTT, 2 mM $MnCl_2$, pH 7.2).

Serial dilution log 10 from 2 mM to 63.2 nM of test compounds are made in 100% DMSO. The dilutions in DMSO are then diluted 50-fold in KR-buffer of which 5 µl is used in the assay, leading to a final compound concentration range in the assay from 10 µM to 0.316 nM.

5 µL/well of test compound in KR buffer (final DMSO concentration in the assay is 1%) is mixed with 5 µl/well of 0.5 µg/mL FynT enzyme (final concentration in the assay is 125 ng/mL). Test compounds and FynT enzyme are pre-incubated 60 minutes at room temperature, before adding 5 µL/well of 400 nM Fluorescin labeled substrate peptide (p34cdc2 substrate peptide, e.g. #R7157/#R7172, Molecular Devices) in KR-buffer. Final peptide substrate concentration in assay is 100 nM. The kinase assay is started by adding 5 µL/well of 0.8 µM ATP in KR-buffer (final ATP concentration is 0.2 µM ATP, Km ATP in FynT IMAP assay). Following incubation for 2 h at room temperature the enzyme reaction is stopped by adding 40 µL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $EC_{50}$ values are determined by curve fitting of the experimental results using Activity Base.

TABLE 4

| EC50 FynT activity values | |
|---|---|
| EC50 | Example |
| ≥1 µM | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133 |

Lyn Enzyme Activity

Lyn enzyme activity is measured using the IMAP (immobilized metal ion affinity-based fluorescence polarization) assay as outlined below.

Lyn enzyme (Millipore catalog #14-510), is diluted to 250 mU/mL in KR buffer (10 mM Tris-HCl, 10 mM $MgCl_2$, 0.01% Tween-20, 0.05% $NaN_3$, 1 mM DTT, 2 mM $MnCl_2$, pH 7.2).

Serial dilution log 10 from 2 mM to 63.2 nM of test compounds are made in 100% DMSO. The dilutions in DMSO are then diluted 50-fold in KR-buffer of which 5 µl is used in the assay, leading to a final compound concentration range in the assay from 10 µM to 0.316 nM.

5 µL/well of test compound in KR buffer (final DMSO concentration in the assay is 1%) is mixed with 5 µl/well of 250 mU/mL Lyn enzyme (final concentration in the assay is 62.5 mU/mL). Test compounds and Lyn enzyme are pre-incubated 60 minutes at room temperature, before adding 5 µL/well of 400 nM Fluorescin labeled substrate peptide (Blk/Lyntide substrate, e.g. #R7188/#R7233, Molecular Devices) in KR-buffer. Final peptide substrate concentration in assay is 100 nM. The kinase assay is started by adding 5 µL/well of 8 µM ATP in KR-buffer (final ATP concentration is 2 µM ATP, Km ATP in Lyn IMAP assay). Following incubation for 2 h at room temperature the enzyme reaction is stopped by adding 40 µL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. $EC_{50}$ values are determined by curve fitting of the experimental results using Activity Base.

TABLE 5

| EC50 Lyn activity values | |
|---|---|
| EC50 | Example |
| ≥1 µM | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 127, 128, 129, 130, 131, 132 |
| ≥100 nM <1 µM | 60, 124, 125, 126, 133 |

The invention claimed is:

1. A method of treating chronic lymphocytic leukemia in a human subject, the method comprising administering to the human subject a compound that is
(S)-4-(8-amino-3-(1-but-2-ynoylpyrrolidin-2-yl)imidazo[1,5-a]pyrazin-1-yl)-N-(pyridin-2-yl)benzamide, having the structure:

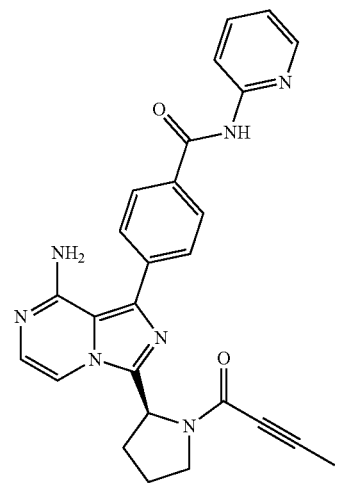 [SMILES: CC#CC(=O)N1CCC[C@H]1c1nc(-c2ccc(C(=O)Nc3ccccn3)cc2)c2c(N)nccn12]

or a pharmaceutically acceptable salt thereof.

2. The method of claim 1, wherein the compound is present in a pharmaceutical composition.

3. The method of claim 2, wherein the pharmaceutical composition comprises one or more pharmaceutically acceptable auxiliaries.

4. The method of claim 2, wherein the pharmaceutical composition is administered to the human subject by oral administration.

5. The method of claim 3, wherein the pharmaceutical composition is administered to the human subject by oral administration.

6. The method of claim 4, wherein the pharmaceutical composition is a tablet.

7. The method of claim 5, wherein the pharmaceutical composition is a tablet.

8. The method of claim 4, wherein the pharmaceutical composition is a capsule.

9. The method of claim 5, wherein the pharmaceutical composition is a capsule.

10. The method of claim 4, wherein the pharmaceutical composition is a suspension.

11. The method of claim 5, wherein the pharmaceutical composition is a suspension.

12. The method of claim 1, wherein the compound is administered to the human subject in an amount of 0.0001-25 mg per kg body weight.

13. The method of claim 1, wherein (S)-4-(8-amino-3-(1-but-2-ynoylpyrrolidin-2-yl)imidazo[1,5-a]pyrazin-1-yl)-N-(pyridin-2-yl)benzamide is administered to the human subject.

14. The method of claim 1, wherein a pharmaceutically acceptable salt of (S)-4-(8-amino-3-(1-but-2-ynoylpyrrolidin-2-yl)imidazo[1,5-a]pyrazin-1-yl)-N-(pyridin-2-yl)benzamide is administered to the human subject.

* * * * *